US012366915B2

(12) United States Patent
Arbel et al.

(10) Patent No.: US 12,366,915 B2
(45) Date of Patent: Jul. 22, 2025

(54) ANNOTATION DATA COLLECTION USING GAZE-BASED TRACKING

(71) Applicant: Agilent Technologies, Inc., Santa Clara, CA (US)

(72) Inventors: Elad Arbel, Santa Clara, CA (US); Itay Remer, Santa Clara, CA (US); Amir Ben-Dor, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 161 days.

(21) Appl. No.: 18/018,109

(22) PCT Filed: Jul. 20, 2021

(86) PCT No.: PCT/IB2021/056548
§ 371 (c)(1),
(2) Date: Jan. 26, 2023

(87) PCT Pub. No.: WO2022/023881
PCT Pub. Date: Feb. 3, 2022

(65) Prior Publication Data
US 2023/0266819 A1 Aug. 24, 2023

Related U.S. Application Data

(60) Provisional application No. 63/057,105, filed on Jul. 27, 2020.

(51) Int. Cl.
*G06T 11/00* (2006.01)
*G06F 3/01* (2006.01)
(Continued)

(52) U.S. Cl.
CPC .......... *G06F 3/013* (2013.01); *G06F 3/04845* (2013.01); *G06F 3/0485* (2013.01);
(Continued)

(58) Field of Classification Search
CPC .... G06F 3/013; G06F 3/04845; G06F 3/0485; G06F 3/04842; G06F 2203/04806;
(Continued)

(56) References Cited

U.S. PATENT DOCUMENTS

2017/0270346 A1* 9/2017 Ascierto ................ G06V 20/69
2018/0268737 A1* 9/2018 Garnavi ................ G06N 3/084
(Continued)

FOREIGN PATENT DOCUMENTS

CN         110441901        11/2019
WO    WO 2022/023881        2/2022

OTHER PUBLICATIONS

International Preliminary Report on Patentability Feb. 9, 2023 From the International Bureau of WIPO Re. Application No. PCT/IB2021/056548. (9 Pages).
(Continued)

*Primary Examiner* — Howard D Brown, Jr.
(74) *Attorney, Agent, or Firm* — ArentFox Schiff LLP

(57) ABSTRACT

There is provided a computer implemented method of automatically creating a training dataset comprising a plurality of records, wherein a record includes: an image of a sample of an object, an indication of monitored manipulations by a user of a presentation of the sample, and a ground truth indication of a monitored gaze of the user viewing the sample on a display or via an optical device mapped to pixels of the image of the sample, wherein the monitored gaze comprises at least one location of the sample the user is viewing and an amount of time spent viewing the at least one location.

18 Claims, 17 Drawing Sheets

(51) Int. Cl.
  *G06F 3/04845* (2022.01)
  *G06F 3/0485* (2022.01)
  *G06T 3/40* (2006.01)
  *G06T 5/50* (2006.01)
  *G06T 7/30* (2017.01)
  *G06V 10/70* (2022.01)

(52) U.S. Cl.
  CPC .................. *G06T 3/40* (2013.01); *G06T 5/50* (2013.01); *G06T 7/30* (2017.01); *G06V 10/70* (2022.01); *G06T 2207/10048* (2013.01); *G06T 2207/10056* (2013.01); *G06T 2207/20081* (2013.01); *G06T 2207/20221* (2013.01); *G06T 2207/30024* (2013.01)

(58) Field of Classification Search
  CPC .... G06T 3/40; G06T 5/50; G06T 7/30; G06T 2207/10048; G06T 2207/10056; G06T 2207/20081; G06T 2207/20221; G06T 2207/30024; G06V 10/70; G06V 2201/03; G06V 10/764; G06V 10/774; G06V 20/69; G06V 40/18; G06N 3/045; G06N 3/08; G06N 20/00; G16H 15/00; G16H 30/20; G16H 40/63; G16H 40/67
  See application file for complete search history.

(56) References Cited

U.S. PATENT DOCUMENTS

2019/0113732 A1* 4/2019 Barral ................ G02B 27/0093
2020/0211233 A1* 7/2020 Siegel ..................... G06F 3/013

OTHER PUBLICATIONS

International Search Report and the Written Opinion Dated Oct. 28, 2021 From the International Searching Authority Re. Application No. PCT/IB2021/056548 (14 Pages).

* cited by examiner

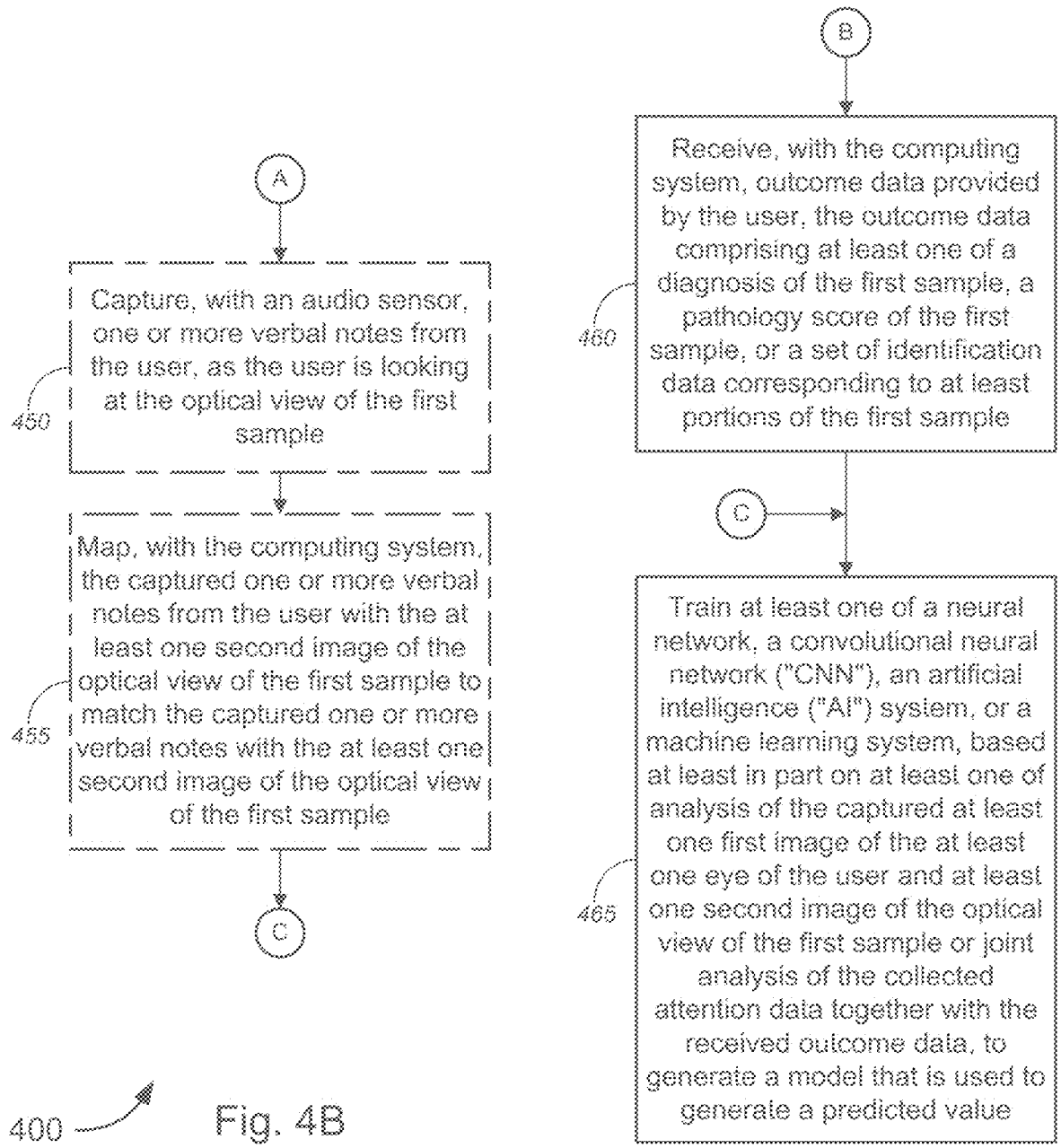

ANNOTATION DATA COLLECTION USING GAZE-BASED TRACKING

RELATED APPLICATIONS

This application is a National Phase PCT Patent Application No. PCT/IB2021/056548 having International filing date of Jul. 20, 2021, which claims the benefit of priority under 35 USC § 119 (e) of U.S. Provisional Patent Application No. 63/057,105 filed on Jul. 27, 2020. The contents of the above applications are all incorporated by reference as if fully set forth herein in their entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, and apparatuses for implementing annotation data collection, and, more particularly, to methods, systems, and apparatuses for implementing annotation data collection using gaze-based tracking, in some cases, for training an artificial intelligence ("AI") system (which might include, without limitation, at least one of a neural network, a convolutional neural network ("CNN"), a learning algorithm-based system, or a machine learning system, and/or the like).

SUMMARY

According to a first aspect, a computer implemented method comprises automatically creating a training dataset comprising a plurality of records, wherein a record includes: an image of a sample of an object, an indication of monitored manipulations by a user of a presentation of the sample, and a ground truth indication of a monitored gaze of the user viewing the sample on a display or via an optical device mapped to pixels of the image of the sample, wherein the monitored gaze comprises at least one location of the sample the user is viewing and an amount of time spent viewing the at least one location.

In a further implementation form of the first aspect, the samples of objects are selected from a group consisting of: biological samples, live cell culture in a microwell plate, slide of pathological tissue sample for generating a pathological report, a 3D radiology image, and a manufactured microarray for identification of manufacturing defects therein.

In a further implementation form of the first aspect, further comprising training a machine learning model on the training dataset for generating an outcome of a target predicted gaze in response to an input of a target image of a target sample of a target object.

In a further implementation form of the first aspect, the ground truth indication of monitored gaze comprises an aggregated amount of time the monitored gaze is mapped to each specific pixel of the image over a viewing time interval.

In a further implementation form of the first aspect, the ground truth indication of monitored gaze comprises at least one of: (i) a heat map corresponding to the image of the sample, wherein a respective intensity of respective pixels of the heat map correlates with the aggregated amount of time the monitored gaze is mapped to each respective pixel, wherein pixels of the heat map are normalized to pixels indicating different actual sizes of the sample at a plurality of zoom levels defined by the monitored manipulations and/or to pixels located at different portions of the sample that are non-simultaneously visible on a display obtained by panning operations of the monitored manipulations and (ii) an overlay on the image of the sample, wherein features of the overlay corresponding to a spread of the gaze and/or indicate the aggregated amount of time.

In a further implementation form of the first aspect, the ground truth indication of the monitored gaze comprises an ordered time sequence that dynamically maps adaptions of the monitored gaze of different fields of view being observed to different specific pixels over a viewing time interval.

In a further implementation form of the first aspect, the ground truth indication of monitored gaze is depicted as at least one of: (i) a directed line overlaid on pixels of the image of the sample indicating dynamic adaptation of the monitored gaze, and (ii) presenting the ordered time sequence with an indication of amount of time spent at each field of view.

In a further implementation form of the first aspect, the record of the training dataset further comprises ground truth indications of manipulations by the user performed to adjust the field of view of the sample, mapped to the ground truth indications of monitored gaze and to the pixels of the image.

In a further implementation form of the first aspect, the sample is viewed as a magnification thereof, wherein the user manipulations being associated with the mapping of the monitored gaze to specific pixels of the image are selected from a group comprising: zoom in, zoom out, pan left, pan right, pan up, pan down, adjustment of light, adjustment of focus, and adjustment of scaling of the image.

In a further implementation form of the first aspect, the sample is viewed via a microscope, wherein monitoring gaze comprises obtaining gaze data from at least one first camera following pupils of the user while the user is viewing the sample under the microscope, wherein the image of the sample being manipulated is captured by a second camera while the user is viewing the sample under the microscope, further comprising obtaining a scanned image of the sample, and registering the scanned image of the sample with the image of the sample captured by the second camera, wherein mapping comprises mapping the monitored gaze to pixels of the scanned image using the registration to the image captured by the second camera.

In a further implementation form of the first aspect, the monitored gaze is represented as a weak annotation, and the record of the training dataset further comprises at least one of the following additional ground truth labels of the image of the sample: when the sample comprises a sample of tissue of a subject: a pathology report created by the user viewing the sample, a pathological diagnosis created by the user viewing the sample, a sample score indicating a pathological evaluation for the sample created by the user viewing the sample, at least one clinical parameter of the subject whose sample is depicted in the sample, history parameter of the subject, and outcome of treatment administered to the subject, when the sample comprises a manufactured microarray: a user provided indication of at least one manufacturing defect, an indication of pass/fail quality assurance test, when the sample comprises a live cell culture: cells growth rate, cells density, cells homogeneity, and cells heterogeneity, and one or more other user provided data items.

In a further implementation form of the first aspect, further comprising training a machine learning model on the training dataset for generating an outcome of: when the sample comprises the sample of tissue of a subject: a target predicted pathology report and/or pathological diagnosis and/or sample score in response to an input of a target image of a target biological sample of pathological tissue of a target individual and a target gaze of a target user, and when the sample comprises the manufactured microarray: a target manufacturing defect and/or indication of pass/fail quality check, in response to an input of a target image of a target manufactured microarray, when the sample comprises a live cell culture: target cells growth rate, target cells density, target cells homogeneity, and target cells heterogeneity.

According to a second aspect, a computer implemented method for assisting visual analysis of a sample of an object, comprises: feeding a target image of the sample of the object into a machine learning model trained on a training dataset comprising a plurality of records, wherein a record includes: an image of a sample of an object, an indication of monitored manipulations by a user of a presentation of the sample, and a ground truth indication of a monitored gaze of the user viewing the sample on a display or via an optical device mapped to pixels of the image of the sample, wherein the monitored gaze comprises at least one location of the sample the user is viewing and an amount of time spent viewing the at least one location, and obtaining as an outcome of the machine learning model, an indication of predicted monitored gaze for pixels of the target image.

In a further implementation form of the second aspect, the outcome comprises a heatmap of a plurality of pixels mapped to pixels of the target image, wherein intensity of pixels of the heatmap correlate to a predicted time for gazing, wherein pixels of the heat map are normalized to pixels indicating different actual sizes of the sample at a plurality of zoom levels defined by the monitored manipulations and/or to pixels located at different portions of the sample that are non-simultaneously visible on a display obtained by panning operations of the monitored manipulations.

In a further implementation form of the second aspect, the outcome comprises a time series indicating dynamic gaze mapped to pixels of the target image over a time interval, and further comprising real time monitoring of a gaze of a user viewing the target image, comparing a difference between the real time monitoring and the time series, and generating an alert when the difference is above a threshold.

In a further implementation form of the second aspect, the record of the training dataset further comprises ground truth indications of manipulations by the user mapped to the ground truth indications of monitored gaze and to the pixels of the image, and wherein the outcome comprises a prediction of manipulation to a presentation of the target image.

In a further implementation form of the second aspect, further comprising real time monitoring of manipulations of a presentation of the sample by a user, comparing a difference between the real time monitoring of manipulation and the prediction of manipulations, and generating an alert when the difference is above a threshold.

According to a third aspect, a computer implemented method for assisting visual analysis of a sample of an object comprises: feeding into a machine learning model, a target image of the sample, and obtaining as an outcome of the machine learning model, a sample score indicating a visual evaluation for the sample, wherein the machine learning model is trained on a training dataset comprising a plurality of records, wherein a record includes an image of a sample of an object, an indication of monitored manipulations by a user of a presentation of the sample, a ground truth indication of a monitored gaze of the user viewing the sample on a display or via an optical device mapped to pixels of the image of the sample, wherein the monitored gaze comprises at least one location of the sample the user is viewing and an amount of time spent viewing the at least one location, and a ground truth indication of a sample visual evaluation score assigned to the sample.

According to a fourth aspect, a component for gaze-tracking for integration with a microscope between an objective lens and an eyepiece, comprises: an optical arrangement that directs a first set of electromagnetic frequencies back-reflected from each eye of a user viewing a sample under a microscope to a respective first camera that generates an indication of tracked gaze of the user, and simultaneously directs a second set of electromagnetic frequencies from the sample under the microscope to a second camera that captures images depicting a field of view the user is viewing.

In a further implementation form of the fourth aspect, the first set of electromagnetic frequencies are infrared (IR) frequencies generated by an IR source, the first camera comprises a near IR camera, the second set of electromagnetic frequencies include the visible light spectrum, the second camera comprises a red-green-blue (RGB) camera, and the optical arrangement includes a beam splitter that directs the first set of electromagnetic frequencies from the IR source to an eyepiece where the eye of the user is located, directs the back-reflected first set from the eye of the user via the eyepiece to the NIR camera, and directs the second set of electromagnetic frequencies from the sample to the second camera and to the eyepiece, wherein the optical arrangement that separates the electromagnetic light waves from a single optical path after reflection from two eyes to two optical paths to two of the first cameras is selected from a group consisting of: polarizers and/or waveplates that direct different polarized light to different paths, and/or using infrared spectral light sources with dichroic mirrors and spectral filters, and/or adding amplitude modulation in different frequencies for each optical path for heterodyne detection.

BACKGROUND

Thousands of stained histopathology slides are being viewed and scored every day in clinical and research labs. Traditionally, slides are scored under microscope, but more recently, slides are scanned and scored on a display screen. Developing digital analysis methods of scanned slides to assist pathologists requires access to a large amount of pathologist annotation to train the algorithm (e.g., identify regions of interest, diagnosis, treatment, etc.), including deep learning, machine learning, or other algorithms, or the like. However, current slide scoring protocols (either under microscope or on screen) do not have explicit annotation requirements, or any non-obtrusive annotation capabilities. As a result, a potentially huge amount of expert annotation (namely, what exact region on the slide guided a pathologist's decision), is not being recorded and is lost. Some conventional techniques tackle this problem by gathering pathologist's region of interests ("ROIs") in the glass slide through mounting a video camera to the microscope that tracks and records the field of view ("FOV") during pathologist's slide examination. This information may later be registered to the whole slide image ("WSI") digital slide and may be used to train a convolutional neural network ("CNN") to diagnosis-relevant or treatment-relevant regions in WSI. Although this method gathers annotations in a nonintrusive manner during a pathologist's routine, it still lacks valuable information about the specific cells or structures that the pathologist was focusing on within the FOVs.

Further, current slides are routinely diagnosed and scored without providing any local information that supports the pathologist decision. On the other hand, collecting detailed spatial annotation that is required for developing AI-based algorithms is expensive and tedious.

Hence, there is a need for more robust and scalable solutions for implementing annotation data collection, and, more particularly, to methods, systems, and apparatuses for implementing annotation data collection using gaze-based tracking, in some cases, for training an AI system.

BRIEF DESCRIPTION OF THE SEVERAL VIEWS OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 4A-4D are flow diagrams illustrating a method for implementing annotation data collection using gaze-based tracking, in accordance with various embodiments.

DETAILED DESCRIPTION

Figure 1:
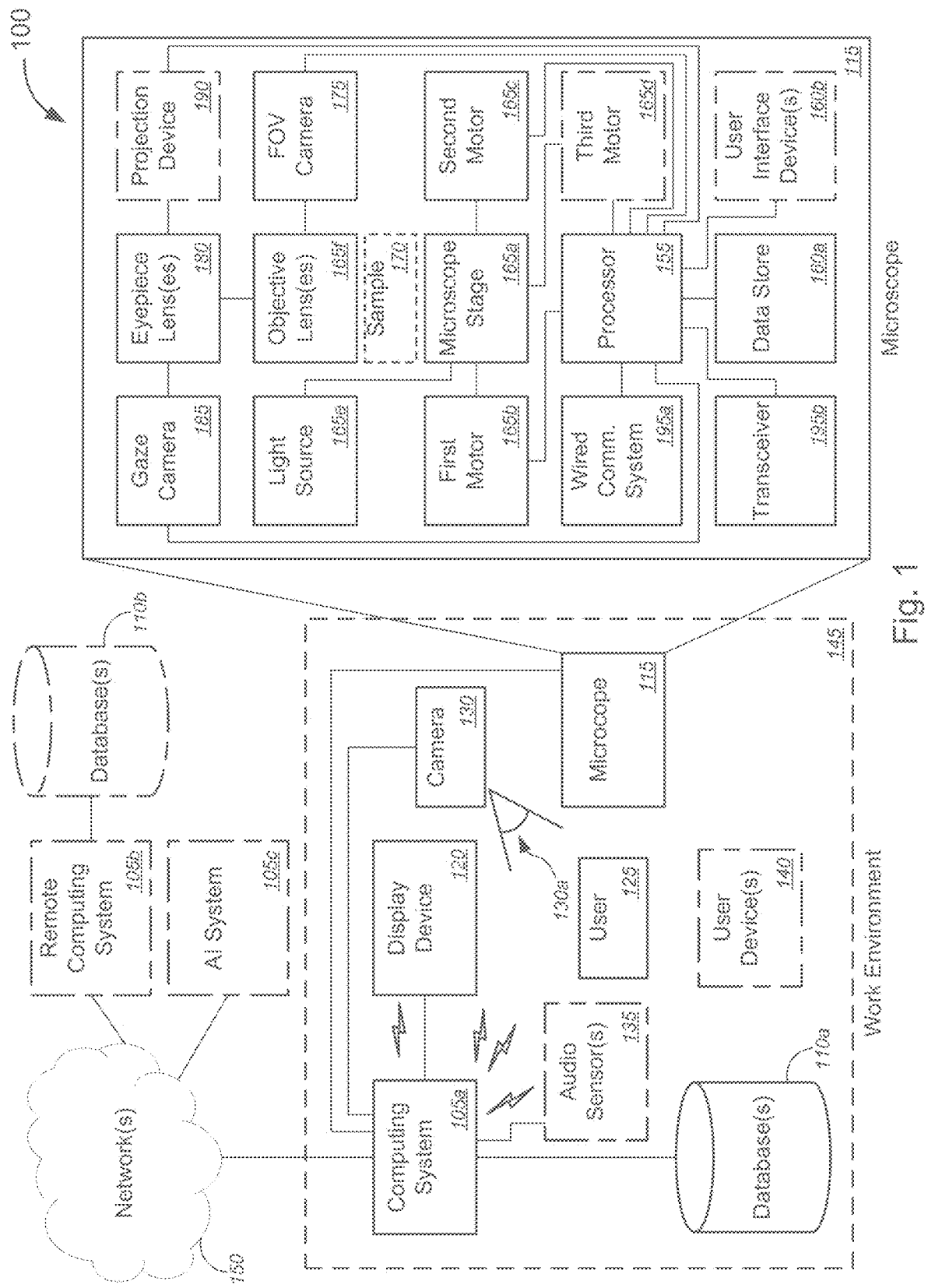
FIG. 1 is a schematic diagram illustrating a system for implementing annotation data collection using gaze-based tracking, in accordance with various embodiments.

An aspect of some embodiments of the present invention relates to systems, methods, a computing device, and/or code instructions (stored on a memory and executable by one or more hardware processors) for automatically creating an annotated training dataset for training a machine learning model. The annotated training dataset includes multiple records, where each record includes an image of a sample of an object, also referred to herein as first sample (e.g., of a slide of pathological tissue, optionally a whole slide image (WSI), or a manufactured object such as a microarray), an indication of monitored gaze (sometimes also referred to herein as attention data) of a respective user obtained during a viewing session of the respective user viewing the sample (e.g., where the user is looking at a current field of view (FOV) seen within a eyepiece of a microscope and/or presented on a display), and optionally an indication of monitored manipulations performed by the respective user for adjusting a presentation of the sample during the viewing session. The monitored gaze represents a ground truth. The monitored gaze may be represented as a weak annotation of the image. The ground truth monitored gaze is mapped to pixels of the image of the respective sample. The monitored gaze include one or more locations (e.g., region) of the sample the user is viewing, and/or an amount of time spent viewing each location. Since a magnification of the sample may be very large and cannot be properly inspected in its entirety on a display, where a FOV represents a portion of the full sample, the user many perform manipulations to select different FOVs and/or adjust the presentation of the FOV in order to visualize the sample, for example, zoom in, zoom out, panning, focus adjustment, light adjustment, and adjustment of scaling of the image. The monitored gaze may be represented, for example, as a heatmap, where pixels of the heat map may indicate an aggregated amount of viewing time during the viewing session that the user gazed at the portion of the sample corresponding to respective pixels of the heatmap. Pixels of the heat map may be normalized to pixels indicating different actual sizes of the sample at different zoom levels defined by the monitored manipulations and/or to pixels located at different portions of the sample that are non-simultaneously visible on a display obtained by panning operations of the monitored manipulations. Records may include additional data. The additional data may be an additional label, which together with the monitored gaze represents the ground truth. Examples of additional data include a visual evaluation score for the sample, which may be an outcome provided by the user reviewing the sample. When the sample is a tissue sample obtained from a subject, the visual evaluation score may be, for example, a clinical score and/or pathological diagnosis, for example, a pathological report. When the sample is a manufactured object, such as a manufactured microarray, the visual evaluation score may be an indication of one or more defects found in the manufactured object.

The samples may be of objects that cannot be viewed by a user in their entirety, for example cannot be presented at a size suitable for visual inspection on a display and/or under a microscope. When the samples are presented at a zoom-in level that is suitable for visual inspection, a portion of the sample is presented on the display and/or depicted under a microscope, while other portions of the sample are not presented. The user performs manipulations to visually examine the rest of the sample, for example, zoom-out, panning, and/or zoom-in on other regions.

Examples of samples of objects include:

Tissue samples, such as of pathological tissue, for example, obtained as a biopsy. Tissue samples may be viewed as prepared slides, such as whole image slides. When such slides are viewed under the microscope and/or on a screen at a zoom-in level that is sufficient for examining details (e.g., single cells, interior of cells, groups of cells), a portion of the image is visible with much of the remaining part of the image being non-visible. The pathologist (or other user) visually examining the sample views the WSI or slide by performing panning operations to view different fields of view at different magnification levels. The pathologist examines the tissue samples, for example, to generate a pathological report, provide a clinical diagnosis, and/or compute a clinical score such as used to determine whether to administer chemotherapy or other therapeutic agents.

Live cell culture, for example, in a microwell plate.

Other biological samples.

Radiological images, for example, three dimensional CT and/or MRI images. A radiologist viewing such 3D images may view single 2D slices at a time, while scrolling back and forth along a z-axis to view higher and lower 2D slices. The radiologist may zoom-in on certain parts of the image. The radiologist may inspect individual organs at a time, repeating the scrolling up and down for the different organs. Multiple organs may be evaluated, for example, when looking for metastatic disease the radiologist may inspect each organs for the presence of tumors. The radiologist examines the 3D images, for example, to generate a radiologist report, provide a clinical diagnosis, and/or compute a clinical score.

Objects may be manufactured objects, for example, microarrays (e.g., glass slide with about 1 million DNA molecules attached in regular pattern), cell cultures, silicon chips, micro-electromechanical system (MEMS) and the like. A user views the manufactured object, or image therefore, as part of a quality assurance process to identify manufacturing defects, and/or indicate whether the manufactured object passes or fails the quality assurance inspection.

Optionally, images of the FOV of the sample depicting what the user is gazing at are captured with the monitored gaze. The images of the FOV may be registered to an image of the sample, such as a WSI obtained by scanning a slide of the sample of tissue, and/or an image of the manufactured object (e.g., hybridized DNA microarray) captured by a camera. When the monitored gaze is mapped to images of the FOV, the registration between the images of the FOV and the image of the sample enables mapping the monitored gaze to the image of the sample. Optionally, indications of the monitored gaze (e.g., heatmaps) that correspond to different FOV (e.g., at different zoom levels) are normalized using data from the manipulations (e.g. zoom-level, panning operations, image scaling) to enable mapping the monitored gaze to the image of the sample. In other words, since the magnified sample is usually very large, the user typically views different fields of view of the sample. Each field of view may represent the portion of the sample that is currently depicted within the viewing lens of the microscope and/or presented on a display. The FOV may be associated with a certain magnification. The same region of the sample may be viewed as different FOVs under different magnifications. Each FOV is mapped to an image of the sample, such as a whole slide image of a sample of pathological tissue on a slide and/or a large image of the manufactured object such as a hybridized DNA microarray. Mappings may be on a pixel level, and/or on a pixel group level, enabling mapping viewing locations (e.g., by tracking pupil movement) of the user to single pixels and/or group of pixels of the FOV and/or the image of the sample (e.g., WSI).

Different machine learning models may be trained on the training dataset, according to the data structure of the records of the training dataset. In one example, the ML model generates an outcome of a target predicted gaze in response to an input of a target image of a target sample. In another example, the ML model generates an outcome of a target predicted manipulation in response to an input of a target image of a target sample and/or monitored gaze. The target predicted gaze and/or manipulations may be used, for example, to train new users (e.g., pathologists) in learning how to examine and/or manipulate new samples, and/or to guide users where to look at new samples, and/or as a form of quality assurance of users viewing new samples to verify that the users looked at and/or manipulated the sample according to standard practice. In yet another example, the ML model generates an outcome of a visual examination, for example, a clinical score, a clinical diagnosis (e.g., for medical images such as pathological slides and/or 3D radiology images), and/or an indication of defects in the manufactured object (e.g., pass/fail quality check, where the defects are located) in response to an input of the target image and/or target gaze and/or target manipulations. In yet another example the ML model generates a combination of the target gaze and visual examination, by generating an indication of where the features that led to the visual examination were found in the sample. For example, which region(s) of the microarray are defective that led to failing of the quality assurance test. For example, which region(s) of the pathological slide were used to compute the clinical score indicating that the patient should be treated with chemotherapy or another therapeutic agent.

The monitored gaze and/or monitored manipulations performed by the user may be collected in the background, without necessarily requiring active user input. The monitored gaze and/or monitored manipulations are collected while the user is viewing the samples based on their standard practice workflow, without interfering with the standard practice workflow and/or without adapting the standard practice workflow.

At least some implementations described herein address the technical problem of creating annotations for images of samples of objects for training machine learning models. Annotation of samples of objects is technically challenging, for several reasons.

First, each sample of the object may include a large number of details for inspection. For example, samples of tissue have a very large number of biological objects, such as cells, blood vessels, and inter-cell objects (e.g., nuclei) depicted therein. In another example, a manufactured microarray has a very large number of DNA molecules clusters, such as about 1 million (or other values). A large number of annotations is required in order to train a machine learning model. Traditionally, the labelling is performed manually. The difficulty is that the person qualified to perform the manual labor is generally a trained domain expert (e.g., pathologist, quality assurance technician), which are in short supply and difficult to find to generate the large number of labelled images. Even when such trained domain experts are identified, the manual labelling is time consuming, since each sample image may contain thousands of features of different types and/or at different states. Some types of features of the objects are difficult to differentiate using the image, which requires even more time to correctly annotate. Moreover, the manual labelling is prone to error, for example, error in differentiating the different types of cellular objects.

Second, each sample requires full visual inspection, with spending additional time inspecting key features. In order to be efficient time wise, the domain experts need to know how much time to spend performing the full visual inspection, and when to spend additional time looking at specific features. As such, capturing the amount of time spent at each location being viewed is collected and used in records for creating the training dataset, as described herein. For some objects, such as tissue samples, each sample is unique, with different structures and/or cells located at different locations and/or having different arrangements. The domain expert has knowledge of how to inspect such samples to gain the visual data needed without missing critical features, for example for generating a pathological report. For objects, such as microarrays, where the arrangement of DNA is regular, the domain expert has knowledge of how to inspect large visual fields with regular patterns to identify abnormalities, for example, to pass/fail a quality assurance inspection. In yet another example, anatomical images (e.g., 3D CT scans, MRI), the heart, the lungs, the stomach, liver, and other organs are almost always located at the same relative locations, since most people have very similar anatomies. However, in most cases, all of the organs need to be visually inspected, to identify clinical features which may be unique to each organ. In some systemic diseases, different organs are affected differently, as part of different pathological manifestations of the same underlying disease. The diagnosis is made by considering the different visual findings.

Third, annotation of the sample requires viewing the sample at different fields of view, which are obtained using different viewing parameters, such as different zoom levels, different amount of light, focus, different image scanning, and/or panning across the sample, in order to get a global and/or local understanding of individual features, and/or interaction between features. For example, for the case of microarrays, visual inspectors use feature extraction to open a quality control image and will look at the image in several magnifications. Additionally, the inspectors will view the images in both standard and log scale. Standard scale is generally used to view the bright features in the top of the image. Log scale is generally used for viewing the dim features at the bottom of the image. Inspectors will pass or fail subjectively based slide based on the type and severity of defects they identify. Examples of anomalies that result in failure include dragger, scratches, empty pockets, merging, nozzle issue, and honeycombs. At least some implementations described herein improve the technology of machine learning, by automatically generating annotations for images of samples (e.g., slides of pathological tissues, 3D radiological images, manufactured objects such as microarrays) for training machine learning models.

Using standard approaches, individual samples of objects (e.g., cells) are manually annotated by a user (e.g., pathologist). The user generates an outcome for the sample, for example, a report (e.g., for tissue samples and/or radiology images), pass/fail for quality assurance for manufactured objects. The outcome is based on features of the sample, which may serve as a ground truth annotation.

In at least some implementations, the improvement is in the monitoring of gaze of a user (e.g., pathologist, radiologist, quality assurance technician) during standard practice working of reading a sample of an object (e.g., of pathological tissue, radiology image, viewing a manufactured object such as a DNA microarray, under a microscope, and/or presented as an image on a display) and optionally monitoring manipulation of the sample by the user (e.g., panning, zoom levels, focus, scaling, light). The monitoring of the gaze and/or monitoring of manipulations of the sample may be performed without necessarily requiring active input from the user, and/or may be performed in the background while the user is performing their work based on standard practice workflow, without necessarily requiring interruption and/or changes to the workflow. The gaze of the user is monitored and mapped to locations (e.g., pixels) of the sample, indicating where the user is looking, and/or the pattern of how the user is looking by considering amount of time spent at each viewed location, for example, first a quick scan of the entire sample, then zoom in to certain regions, zoom out to get a view of a larger tissue structure, then zoom in again, and the like. The image of the sample is annotated with an indication of the monitored gaze and/or the manipulations, for example, creating a heat map where intensity of pixels indicates total aggregated viewing time at locations of the sample corresponding to pixels of the heat map. Pixels of the heat map may be normalized to pixels indicating different actual sizes of the sample at a different of zoom levels defined by the monitored manipulations and/or to pixels located at different portions of the sample that are non-simultaneously visible on a display obtained by panning operations of the monitored manipulations. A weak label in the form of a visual indication (e.g., clinical score, pathological score, pathological report, clinical diagnosis, indication of pass/fail for quality assurance of the object, indication of defects found in the object) may be assigned to the sample based on the outcome manually generated by the user. Other data may be included in the weak label, for example, audio labels generated from audio messages recorded by an audio sensor, for example, recording short verbal notes made by the user while viewing the sample, for example, as described herein.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
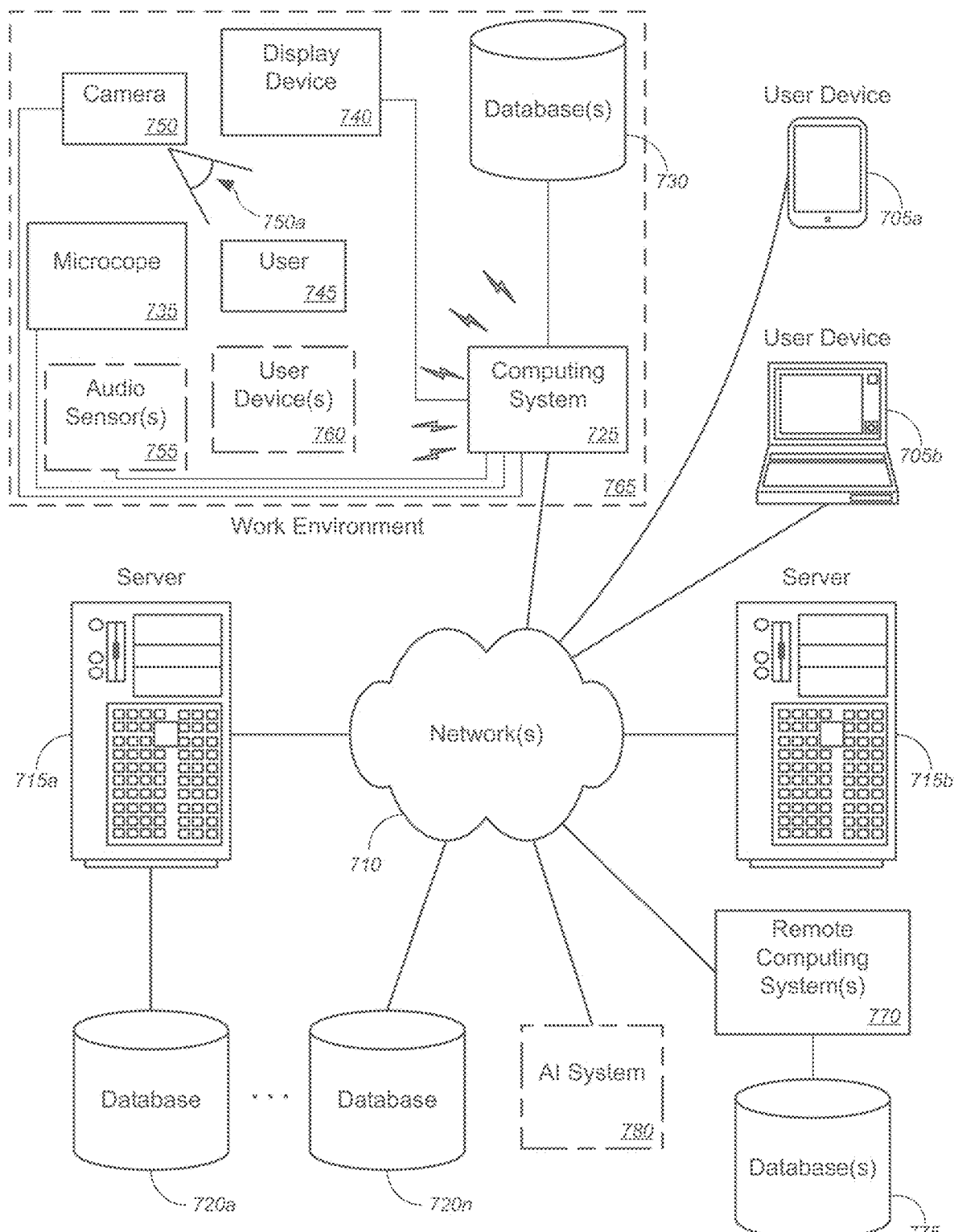
FIG. 7 is a block diagram illustrating a networked system of computers, computing systems, or system hardware architecture, which can be used in accordance with various embodiments.
Figure 8:
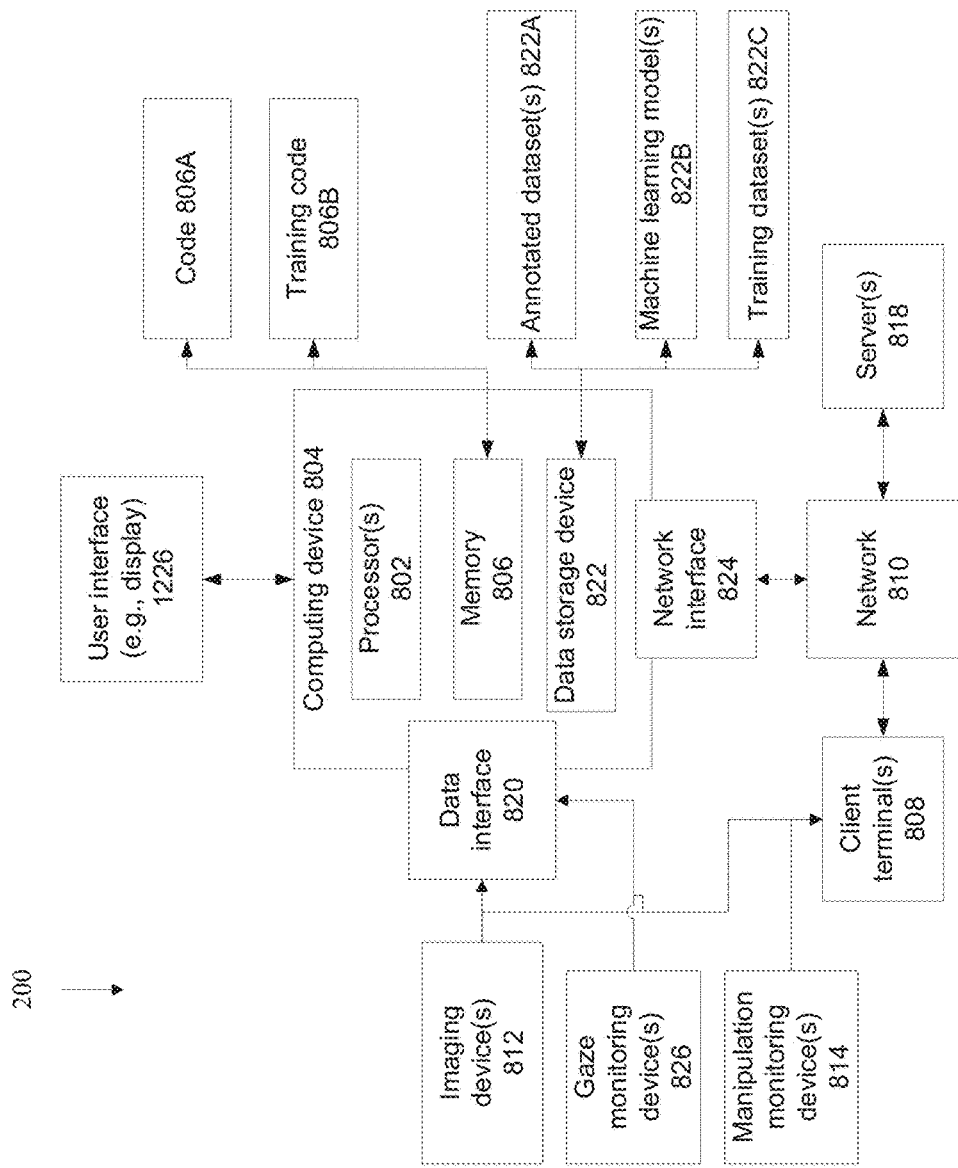
FIG. 8 is block diagram of components of a system for creating a training dataset of images annotated with indications of monitored gaze and/or monitored manipulations, and/or for training a machine learning model(s) on the training dataset, in accordance with various embodiments.

Reference is now made to FIG. 8, which is block diagram of components of a system 800 for creating a training dataset of images annotated with indications of monitored gaze and/or monitored manipulations, and/or for training a machine learning model(s) on the training dataset, in accordance with some embodiments of the present invention. System 800 may be an alternative to, and/or combined with (e.g., using one or more components) the system described with reference to FIGS. 1, 2A-2B, 3A-3D, 6, 7 and 12.

System 800 may implement the acts of the method described with reference to FIGS. 4A-4D, 5A-5D, 9, 10, and 11, optionally by a hardware processor(s) 802 of a computing device 804 executing code instructions 806A and/or 806B stored in a memory 806.

Computing device 804 may be implemented as, for example, a client terminal, a server, a virtual server, a laboratory workstation (e.g., pathology workstation), a quality assurance workstation, a manufacturing workstation, a procedure (e.g., operating) room computer and/or server, a virtual machine, a computing cloud, a mobile device, a desktop computer, a thin client, a Smartphone, a Tablet computer, a laptop computer, a wearable computer, glasses computer, and a watch computer. Computing device 804 may include an advanced visualization workstation that sometimes is implemented as an add-on to a laboratory workstation and/or quality assurance workstation and/or other devices for presenting images of samples of objects to a user (e.g., domain expert).

Different architectures of system 800 based on computing device 804 may be implemented, for example, central server based implementations, and/or localized based implementation.

In an example of a central server based implementation, computing device 804 may include locally stored software that performs one or more of the acts described with reference to FIGS. 4A-4D, 5A-5D, 9, 10, and 11, and/or may act as one or more servers (e.g., network server, web server, a computing cloud, virtual server) that provides services (e.g., one or more of the acts described with reference to FIGS. 4A-4D, 5A-5D, 9, 10, and 11) to one or more client terminals 808 (e.g., remotely located laboratory workstations, remotely located quality assurance workstation, remotely located manufacturing workstation, remote picture archiving and communication system (PACS) server, remote electronic medical record (EMR) server, remote sample image storage server, remotely located pathology computing device, client terminal of a user such as a desktop computer) over a network 810, for example, providing software as a service (SaaS) to the client terminal(s) 808, providing an application for local download to the client terminal(s) 808, as an add-on to a web browser, a tissue sample imaging viewer application, a quality assurance imaging viewing application, and/or providing functions using a remote access session to the client terminals 808, such as through a web browser.

In one implementation, multiple gaze monitoring devices 826 monitor gaze of respective users viewing samples on an imaging device 812 (e.g., microscope and/or display), and optionally multiple manipulation monitoring devices 850 monitor manipulation of the respective sample by the respective user (e.g., pan, zoom in/out, light adjustment, focus adjustment, scale adjustment). Exemplary gaze monitoring devices 826 are described, for example, with reference to 2A-2B, 3A-3D and 12. Images of respective samples are captured (e.g., by the imaging device 812 and/or by another device). The monitored gaze data and/or monitored manipulation data and/or the images of the sample may be provided to respective e client terminals 808. Each of the multiple client terminals 808 provides monitored gaze data and/or monitored manipulation data and/or the images to computing device 804, optionally over a network 810. Computing device may create a respective annotated dataset 822A by annotating the image of the sample with the corresponding ground truth of the monitored gaze data and/or the monitored manipulation data and/or other data (e.g. clinical scores), as described herein. One or more training datasets 822C may be created from annotated dataset(s) 822A, as described herein. One or more machine learning models 822B may be trained on training dataset(s) 822C, as described herein. Training of ML model(s) 822B may be locally performed by computing device 804, and/or remotely by another device (e.g., server) where the trained ML model(s) 822B may be provided to computing device 804 and/or remotely accessed by computing device 804. In another implementation, computing device 804 obtains a respective image of a respective sample from each of multiple client terminals 808, and feeds the respective images into the trained ML model 822B for obtaining a respective outcome, such as a heatmap indicating regions where the user should look. The respective outcomes are provided to the corresponding client terminals 808 for local presentation and/or user (e.g., training, monitoring the user, as described herein).

In a local based implementation, each respective computing device 804 is used by a specific user, for example, a specific pathologist and/or specific quality assurance technician, and/or a group of users in a facility, such as a hospital and/or pathology lab and/or manufacturing facility. Computing device 804 receives the monitored gaze data and/or the monitored manipulation data and/or visual assessment and/or other data (e.g., audio tags) and/or the image of the sample, for example, directly, and/or via an image repository such as server 818 (e.g., PACS server, cloud storage, hard disk). Computing device 804 may locally generate annotated dataset(s) 822A, create training dataset(s) 822C, and/or train ML model(s) 822B, as described herein. Computing device 804 may locally feed the image of the sample into trained ML model(s) 822B to obtain an outcome, which may be locally used (e.g., presented on a display, used to train the user, used to guide the user), as described herein.

Sample images may be locally fed into one or more machine learning model(s) 822B to obtain an outcome. The outcome may be, for example, presented on display 826, locally stored in a data storage device 822 of computing device 804, and/or fed into another application which may be locally stored on data storage device 822. The outcome may be used, for example, to train a user, to monitor a user's work such as for quality assurance, and/or to aid the user, as described herein. Training of machine learning model(s) 822B may be locally performed by each respective computing device 804 based on images of samples and/or gaze data, for example, different pathological labs may each train their own set of machine learning models using their own samples and gaze data from their own pathologists. In another example, different manufacturing facilities may each train their own set of machine learning models using their own samples and gaze data from their own quality assurance technicians. In another example, trained machine learning model(s) 822B are obtained from another device, such as a central server.

Computing device 804 receives images of samples of objects captured by one or more imaging device(s) 812. Exemplary imaging device(s) 812 include: a scanner and a camera. Images of the sample may be presented on a display implementation of imaging device(s) 812. In another example, imaging device 812 is implemented as a microscope, where images of the sample are viewed by the user via the microscope.

Imaging device(s) 812 may create and/or present two dimensional (2D) images of samples of objects, for example, whole sample images, such as an image of a whole slide in the case of tissue samples, and/or an image of a whole microarray in the case of manufactured microarrays being evaluated for manufacturing defects. It is noted that the samples may represent 3D data, where features of the object at different depths are depicted by adjusting the focus.

Sample images captured by imaging machine 812 may be stored in an image repository, such as a server(s) 818, for example, a storage server (e.g., PACS, EHR server, manufacturing and/or quality assurance server), a computing cloud, virtual memory, and a hard disk.

Annotated dataset(s) 822A are created by annotating image(s) of the sample(s) with a ground truth indication of gaze, and/or manipulation data, and/or other data, as described herein.

Training dataset(s) 822C may be created based on annotated dataset(s) 822A, as described herein.

Machine learning model(s) 822B may be trained on training dataset(s) 822C, as described herein.

Computing device 804 may receive the sample images and/or monitored gaze data and/or monitored manipulations and/or other data from imaging device 812 and/or gaze monitoring device 826 and/or manipulation monitoring device(s) 814 using one or more data interfaces 820, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)). Alternatively or additionally, computing device 804 may receive the sample images and/or monitored gaze data and/or monitored manipulations from client terminal(s) 808 and/or server(s) 818.

Hardware processor(s) 802 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 802 may include one or more processors (homogenous or heterogeneous), which may be arranged for parallel processing, as clusters and/or as one or more multi core processing units.

Memory 806 (also referred to herein as a program store, and/or data storage device) stores code instruction for execution by hardware processor(s) 802, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 806 stores code 806A and/or training code 806B that implements one or more acts and/or features of the method described with reference to FIGS. 4A-4D, 5A-5D, 9, 10, and 11.

Computing device 804 may include a data storage device 822 for storing data, for example, annotated dataset(s) 822A of sample images annotated with monitored gaze data and/or monitored manipulation data, machine learning model(s) 822B as described herein and/or training dataset 822C for training machine learning model(s) 822B, as described herein. Data storage device 822 may be implemented as, for example, a memory, a local hard-drive, a removable storage device, an optical disk, a storage device, and/or as a remote server and/or computing cloud (e.g., accessed over network 810). It is noted that execution code portions of the data stored in data storage device 822 may be loaded into memory 806 for execution by processor(s) 802.

Computing device 804 may include data interface 824, optionally a network interface, for connecting to network 810, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 804 may access one or more remote servers 818 using network 810, for example, to download updated versions of machine learning model(s) 822B, code 806A, training code 806B, and/or the training dataset(s) 822C.

Computing device 804 may communicate using network 810 (or another communication channel, such as through a direct link (e.g., cable, wireless) and/or indirect link (e.g., via an intermediary computing device such as a server, and/or via a storage device) with one or more of:

Client terminal(s) 808, for example, when computing device 804 acts as a server providing image analysis services (e.g., SaaS) to remote terminals, as described herein.

Server 818, for example, implemented in association with a PACS and/or electronic medical record and/or manufacturing/quality assurance sever, which may store sample images captured by imaging device 812 and/or gaze monitoring data captured by gaze monitoring device 826 and/or manipulation data captured by manipulation monitoring device 814, for different users.

It is noted that imaging interface 820 and data interface 824 may exist as two independent interfaces (e.g., two network ports), as two virtual interfaces on a common physical interface (e.g., virtual networks on a common network port), and/or integrated into a single interface (e.g., network interface).

Computing device 804 includes or is in communication with a user interface 826 that includes a mechanism designed for a user to enter data (e.g., create report) and/or view data (e.g., view the sample). Exemplary user interfaces 826 include, for example, one or more of, a touchscreen, a microscope, a display, a keyboard, a mouse, and voice activated software using speakers and microphone.

Figure 9:
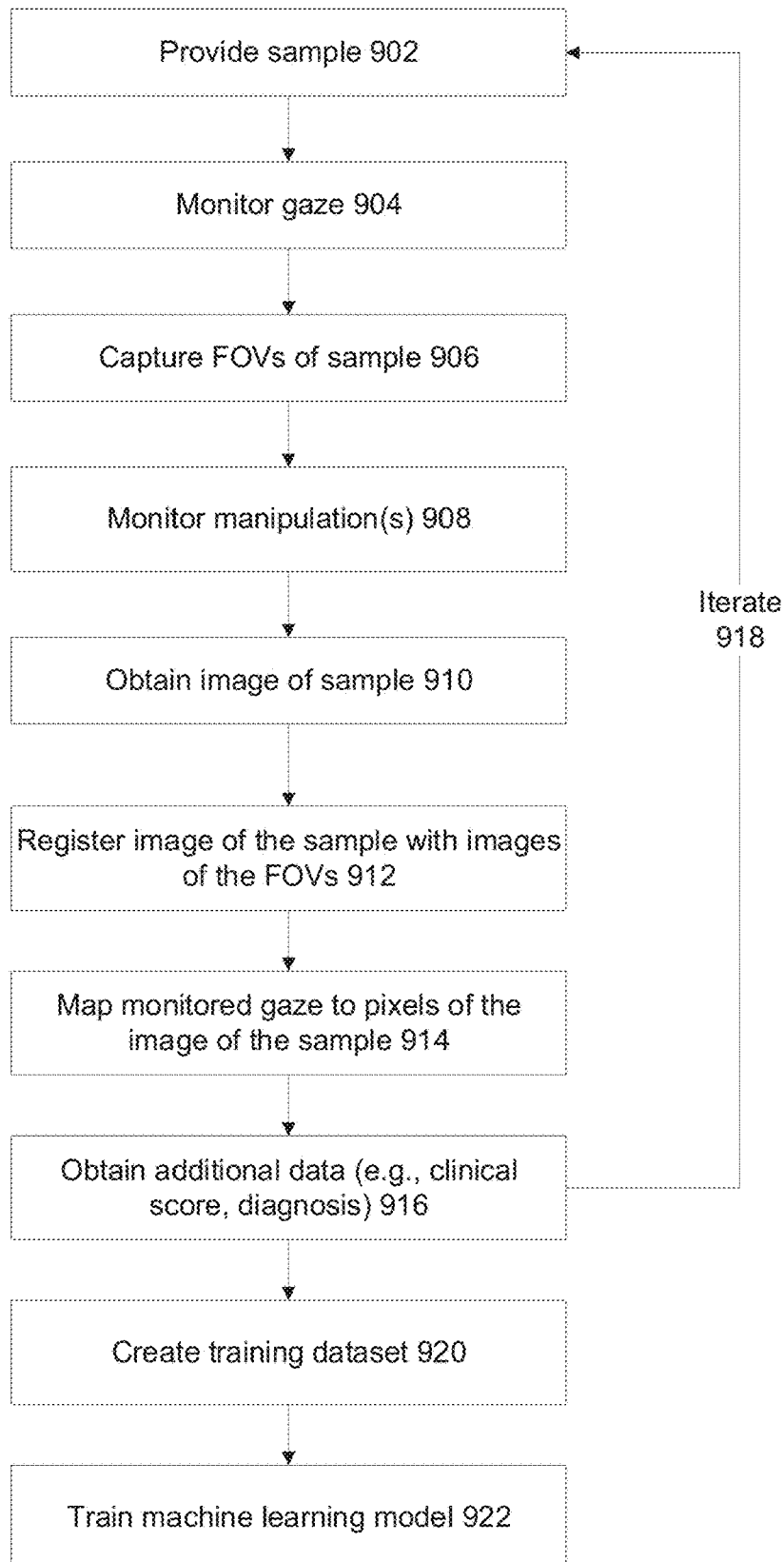
FIG. 9 is a flowchart of a method of automatically creating an annotated training dataset comprising images of samples of objects annotated with monitored gaze, for training of a ML model, in accordance with various embodiments.

Reference is now also made to FIG. 9, which is a flowchart of a method of automatically creating an annotated training dataset comprising images of samples of objects annotated with monitored gaze, for training of a ML model, in accordance with some embodiments of the present invention.

Referring now back to FIG. 9, at 902, a sample of an object is provided. The sample may be, for example, a biological sample, a chemical sample, and/or a manufactured sample, (e.g., electro and/or mechanical components).

Examples of samples include microscope slides of tissues (e.g., created by slicing a frozen section, and/or formalin-fixed paraffin embedded (FFPE) slides) which may be pathological tissue, and live cell cultures. The sample may be contained in other ways, for example, within at least one of a transparent sample cartridge, a vial, a tube, a capsule, a flask, a vessel, a receptacle, a microarray, or a microfluidic chip. The sample of tissue may be obtained intra-operatively, during for example, a biopsy procedure, a FNA procedure, a core biopsy procedure, colonoscopy for removal of colon polyps, surgery for removal of an unknown mass, surgery for removal of a benign cancer, and/or surgery for removal of a malignant cancer, surgery for treatment of the medical condition. Tissue may be obtained from fluid, for example, urine, synovial fluid, blood, and cerebral spinal fluid. Tissue may be in the form of a connected group of cells, for example, a histological slide. Tissue may be in the form of individual or clumps of cells suspended within a fluid, for example, a cytological sample.

In another example, the sample may be a statistically selected sample of manufactured objects, such as microarrays (e.g., of DNA), silicon chips, and/or electrical circuits, which may be selected for quality assurance evaluation, such as to identify manufacturing defects and/or to determine pass/fail.

At 904, gaze of the user viewing the sample is monitored. The sample may be viewed under a microscope and/or other optical device, and/or an image of the sample may be presented on a display which is viewed by the user. The image and/or view may be of arbitrary magnification.

The monitored gaze may be collected without interrupting, slowing, or encumbering the user, for example, as the user is providing the outcome data while viewing and/or analyzing the sample using the microscope and/or by viewing on the display.

The gaze of the user may be monitored by tracking pupil movements of the user as the user is viewing the sample under the microscope and/or presented on a display, for example, using devices described with reference to FIGS. 2A-2B, 3A-3D, and 12. The pupil movements of the user may be tracked by a camera, for example, as described herein.

The pupil movements are mapped to regions within the field of view of the sample that the user is looking at. Pupil movements may be tracked with different resolution levels, indicating different levels of accuracy at what the user is actually looking at, such as in the case of tissues: single cells, or a group of cells in a region, and the like, and/or in the case of manufactured objects: microscopic features such as DNA strands and/or microscopic electro and/or mechanical components. The pupil movements may be mapped to different sized regions, for example, mapped to single pixels of an image of the FOV and/or sample, and/or mapped to groups of pixels, and/or mapped to the FOV as a whole. Broader and/or lower resolution tracking may be used for weak annotating of FOV and/or images of the samples in the training dataset, as described herein. Weak annotation of the FOV and/or images of the samples in the training dataset may be from any gaze coordinates at any resolution.

Optionally, the gaze of the user is tracked as a function of time. An indication of the amount of time the monitored gaze is mapped to each specific region of the sample over a time interval may be determined. The amount of time spent may be defined, for example, as per FOV, per pixel and/or per group of pixels of the image mapped to the FOV of the sample the user is viewing (e.g., as described herein). For example, over the course of a 10 minute viewing session, the user spent 1 minute looking at one FOV, and 5 minutes looking at another FOV. Alternatively or additionally, the monitored gaze is represented and/or includes an ordered time sequence that dynamically maps adaptions of the monitored gaze of different fields of view being observed to different specific pixels over the viewing time interval. For example, the user spent the first minute of the viewing session looking at a first FOV located at about the center of the sample, then spent 5 minutes looking at a second FOV located to the right of the first field of view, then spent another 2 minutes looking back again at the first FOV.

The monitored gaze may be visualized and/or implemented as a data structure, optionally a heat map, that corresponds to the image of the sample. Pixels of the heat map correspond to pixels and/or groups of pixels of the image of the sample. A respective intensity of respective pixels of the heat map correlates with an indication of monitored gaze is mapped to each respective pixel, for example, the pixel intensity values of the heat map represent an aggregated amount of time that the user spent viewing those pixels. The heat map may be presented as an overlay over the image of the sample. The mapping of time to pixel intensity values may be, for example, based on set thresholds (e.g., less than 1 minute, between 1-3 minutes, and >3 minutes), and/or relative amount of time spent (e.g., >50% of total time, 20-50% of total time, and <20% of total time), or other approaches.

The heat map may represent the aggregated amount of time spent at each pixel and/or regions of the FOV. An indication of a time sequence indicating dynamic adaptation of the monitored gaze (i.e., where the user looked as a function of time) may be computed in addition and/or as an alternative to the heat map. The monitored gaze indicating gaze as a function of time may be represented, for example, as a directed line overlaid on pixels of the image of the sample and/or overlaid on the heat map. In another example, the monitored gaze may be represented as the ordered time sequence of each FOV labelled with an indication of amount of time spent at the respective FOV. Each FOV may be mapped to the image of the sample (WSI), for example, shown as a boundary representing the FOV overlaid on the image of the sample.

The monitored gaze may be represented using other data structures, for example, a vector of coordinates within a coordinate system of the FOV indicating where the user is looking. The vector may be a time sequence indicating the locations within the FOV that the user looked at over time. In yet another example, the monitored gaze may be represented using one or more successive overlays, where each overlay includes markings over regions of the FOV where the user is gazing (e.g. color, shape, highlight, outline, shadow, pattern, jet colormap, and the like) and may represent monitored gaze during a small time interval (e.g., second, 10 seconds, 30 seconds, and the like). In yet another example, the monitored gaze may be represented by indicating the amount of time spent gazing at regions of each FOV, where images of the FOVs may be sequentially arranged according to the user's viewing of the FOVs. For example, using outlines (or other markings, such as shading, highlighting, and the like) over the FOV indicating amount of time spent gazing at the region depicted therein. Time may be represented, for example, by metadata, thickness of the outline, and/or color and/or intensity of the markings. Multiple outlines may be presented, where each outline indicates a different gaze. For example, 3 circles are shown on the FOV, where a red circle indicates gaze of 3 minutes, and two blue circles indicate gaze of <30 seconds.

Figure 11:
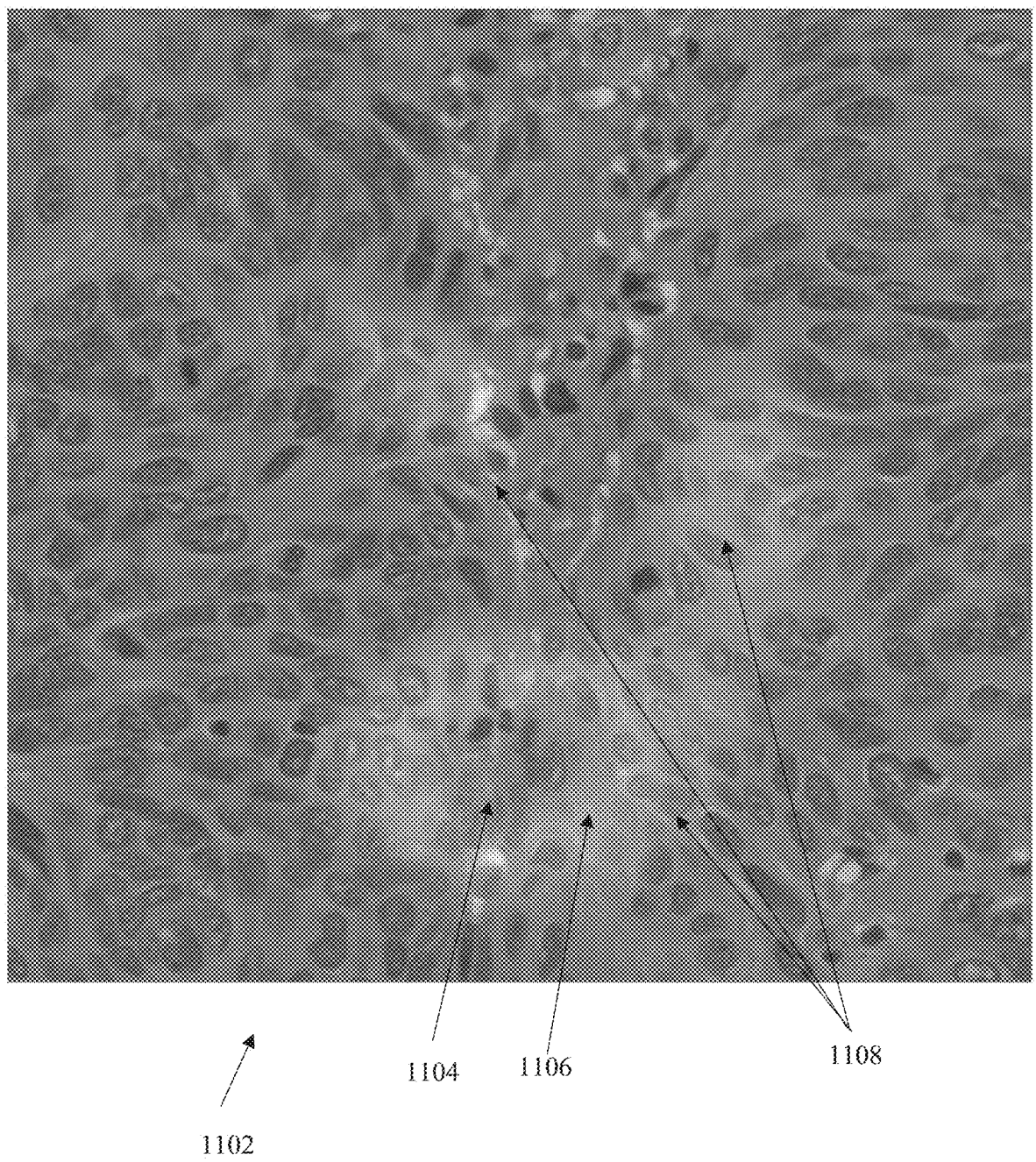
FIG. 11 is a schematic depicting a heat map overlaid on an image of an observed field of view of a sample of an object, in accordance with various embodiments.

Reference is now made to FIG. 11, which is a schematic depicting a heat map (represented as a jet colormap) overlaid on an image 1102 of an observed field of view of a sample of an object, in accordance with some embodiments of the present invention. In the depicted case, the sample is a slide of tissue obtained from a subject. High intensity pixel values 1104 represent regions where the user spent a significant amount of time viewing that region, middle intensity pixel values 1106 represent regions where the user spent a medium amount of time viewing that region, and low intensity pixel values 1108 represent regions where the user spent little amount of time viewing that region. Referring now back to 906 of FIG. 9, the FOV of the sample being viewed by the user is captured. The FOV may be dynamically captured, optionally as a function of time. A time sequence of the FOVs viewed by the user may be generated.

The FOV, when viewed using a microscope, may be captured by a camera that captures images of the sample as seen under a microscope while the user is viewing the sample under the microscope (optionally by a different camera than the one used to track eye movements of the user viewing the sample under the microscope).

When the FOV is presented on a display, the FOV presented on the display may be captured, for example, by performing a screen capture operation.

At 908, manipulation(s) performed by the respective user of a presentation of FOV of the sample may be monitored.

The sample, when magnified, may be very large, and not capable of being simultaneously viewed by a user to enable a proper analysis. As such, the user may manipulate the image of the sample being viewed on a display and/or manipulate the slide and/or the microscope, to generate different FOVs.

Examples of manipulations include: zoom in, zoom out, pan left, pan right, pan up, pan down, adjustment of light, adjustment of scale, and adjustment of focus (e.g., in-focus, out-of-focus) using axial axis (z-axis) scanning. In the case of the sample being a slide of tissue, the slide may be adjusted along the z-axis using a z-axis knob, to view different depths of the tissue under a microscope. In the case of the sample being a 3D image, the 3D image may be sliced into 2D planes, with scrolling forward and backwards done for the 2D planes.

When the image of the sample is presented on a display, the manipulations may be monitored by monitoring user interactions with a user interface associated with a display, for example, icons, a keyboard, a mouse, and a touch screen. When the sample is viewed under a microscope, the manipulations may be monitored, for example, by sensors associated with different components of the microscope, for example, to detect which zoom lens is being used, and/or associated with components that adjust the position of the sample and/or amount of light.

The manipulations may be monitored as a function of time, for example, as a time sequence that indicates which manipulations were performed over the viewing time interval.

The monitored manipulations may be correlated with the monitored gaze, for example, correlated to correspond to the same timeline. For example, at 1 minute from the start of the viewing session, the user switched the zoom from 50× to 100×, and the FOV changes from FOV_1 to FOV_2.

The manipulations (which may be used as ground truth labels) may be represented as an overlay on the image the sample (e.g., obtained as in 910) indicating the aggregated amount of time and/or indicating the sequence. For example, as a heat map corresponding to the image of the sample, where a respective intensity of respective pixels of the heat map correlates with the aggregated amount of time the monitored gaze is mapped to each respective pixel. In another example, one or more boundaries (e.g., circle, square, irregular shape) are overlaid on the image of the sample, where dimensions of each boundary correspond to a spread of the gaze and a marking of each boundary indicates the aggregated amount of time (e.g., thickness and/or color of the boundary).

At 910, an image of the sample may be obtained. The image may be of the whole sample, such as a whole sample image, such as a whole slide image and/or high resolution image of a whole manufactured object. The image of the sample may be obtained, for example, by scanning the slide with a scanner and/or using a high resolution camera. Alternatively or additionally, the image of the sample may be created as a union of images of the FOVs of the sample.

At 912, the image of the sample may be registered with the images of the FOV of the sample. The images of the FOV are captured while the user is viewing the sample under the microscope, and depict what the user is viewing using the microscope. It is noted that when the user is viewing the sample on a display, registration to the image of the sample is not necessarily required since the user is directly viewing FOV of the image of the sample.

Registration may be performed, by a registration process, for example, by matching features of the image of the FOV with images of the sample. The registration may be rigid, and/or non-rigid, such as when the tissue sample might be physically moved during handling.

At 914, the monitored gaze is mapped to pixels of the image of the sample, optionally the scanned and/or WSI.

The mapping may be performed using the FOVs registered to the image of the sample (e.g., WSI and/or scanned image), i.e., the monitored gaze is mapped to the FOVs which are registered to the image of the sample, enabling mapping the monitored gaze directly to pixels of the image of the sample.

Mapping of the monitored gaze may be per pixel of the image of the sample, and/or per group of pixels of the image of the sample and/or per region of the image of the sample.

The representation of the monitored gaze, optionally the heat map, may be normalized to the pixels of the image of the sample. Since the monitored gaze may be initially correlated to FOVs obtained at different zoom levels, and/or since the monitored gaze may be initially correlated to FOVs obtained at different locations of the sample (which are not simultaneously visible on a display), the monitored gaze may require normalization in order to map to pixels of the image of the sample.

At 916, additional data, optionally metadata, associated with the sample may be obtained. The additional data may be assigned as a weak label to the image of the sample as a whole, for example, to the scanned image and/or to the WSI.

Examples of additional data include:
When the sample is tissue of a subject and/or a radiology image of the subject: a pathology/radiology report created by the user viewing the sample, a pathological/radiology diagnosis created by the user viewing the sample (e.g., type of cancer), a sample score indicating a pathological/radiology evaluation for the sample created by the user viewing the sample (e.g., percentage of tumor cells, Gleason score), at least one clinical parameter of the subject whose tissue is depicted in the sample (e.g., cancer stage), history parameter of the subject (e.g., smoker), and outcome of treatment administered to the subject (e.g., responsive to chemotherapy).
When the sample is a manufactured microarray: a user provided indication of at least one manufacturing defect seen in the manufactured microarray, and/or an indication of whether the manufactured microarray passed or failed a quality assurance text.
When the sample comprises a live cell culture: cells growth rate, cells density, cells homogeneity, and cells heterogeneity.
Other user provided data.

The additional data may be obtained, for example, from manual input provided by the user, automatically extracted from the pathological report, and/or automatically extracted from an electronic health record of the subject (e.g., medical history, diagnostic code).

At 918, one or more features described with reference to 902-916 are iterated for multiple different users, where each user may be viewing a different samples of tissue.

At 920, a training dataset of multiple records may be created. Each record may include an image of the sample (e.g., scanned image, WSI), and one or more of the following which may serve as target input and/or ground truth: monitored gaze mapped to pixels of the image of the sample, manipulations by the respective user performed to adjust the field of view of the sample, and the additional data.

The designation of target input and ground truth may be made according to the desired output of the ML model being trained, as described herein.

At 922, one or more machine learning models are trained on the training dataset.

In one example, the ML model is trained for generating an outcome of a target predicted gaze in response to an input of a target image of a target sample. Such model may be used, for example, to train new pathologists/radiologists on how to gaze at samples and/or as a quality control measure to verify pathologists/radiologists are appropriately gazing at samples. In another example, to train new quality assurance technicians on how to gaze at manufactured objects to evaluate manufacturing defects and/or for quality assurance and/or monitor the quality assurance technicians. In another example, to train new domain experts how to gaze at live cell cultures. Such ML model may be trained on a training dataset that includes multiple records, each record including an image of a sample, and a ground truth indication of monitored gaze of the user viewing the sample. The manipulations performed by the target user viewing the target image may be fed as input into the ML model when records of the training dataset also include the manipulations performed by users viewing the samples of the records.

In another example, the ML model is trained for generating an outcome of the additional data, such as a target visual evaluation, for example, quality assurance outcome (e.g., pass/fail, identified manufacturing defects), score clinical score for the sample, pathological/radiology diagnosis and/or target predicted pathology/radiology report. In another example, when the sample is a live cell culture, the ML model is trained to generate an outcome of: target cells growth rate, target cells density, target cells homogeneity, and/or target cells heterogeneity. Such model may be used, for example, to determine the additional data for the target sample. The ML model is fed an input of one or more of: the target image of the target sample, monitored gaze of the target user viewing the target sample, and manipulations of a presentation of the target sample performed by the target user. Such ML model may be trained on a training dataset that includes multiple records, each record including an image of a sample, a ground truth indication of the additional data for the sample, and monitored gaze and optionally monitored manipulations of the respective user viewing the sample of the record.

In yet another example, the ML model is trained for generating an outcome of a target predicted manipulation of the presentation of the sample to be performed in response to an input of a target image of a target sample. Such model may be used, for example, to train new domain experts on how to manipulate samples to obtained FOVs that enable proper viewing of the sample and/or as a quality control measure to verify existing domain experts are appropriately manipulating samples to obtain FOV that enable proper viewing of the sample. Such ML model may be trained on a training dataset that includes multiple records, each record including an image of a sample, and a ground truth indication of manipulations performed by the user viewing the sample. The gaze of the target user viewing the target image may be fed as input into the ML model when records of the training dataset also include the gaze of users viewing the samples of the records.

Exemplary architectures of the machine learning models described herein include, for example, statistical classifiers and/or other statistical models, neural networks of various architectures (e.g., convolutional, fully connected, deep, encoder-decoder, recurrent, graph), support vector machines (SVM), logistic regression, k-nearest neighbor, decision trees, boosting, random forest, a regressor, and/or any other commercial or open source package allowing regression, classification, dimensional reduction, supervised, unsupervised, semi-supervised or reinforcement learning. Machine learning models may be trained using supervised approaches and/or unsupervised approaches.

Figure 10:
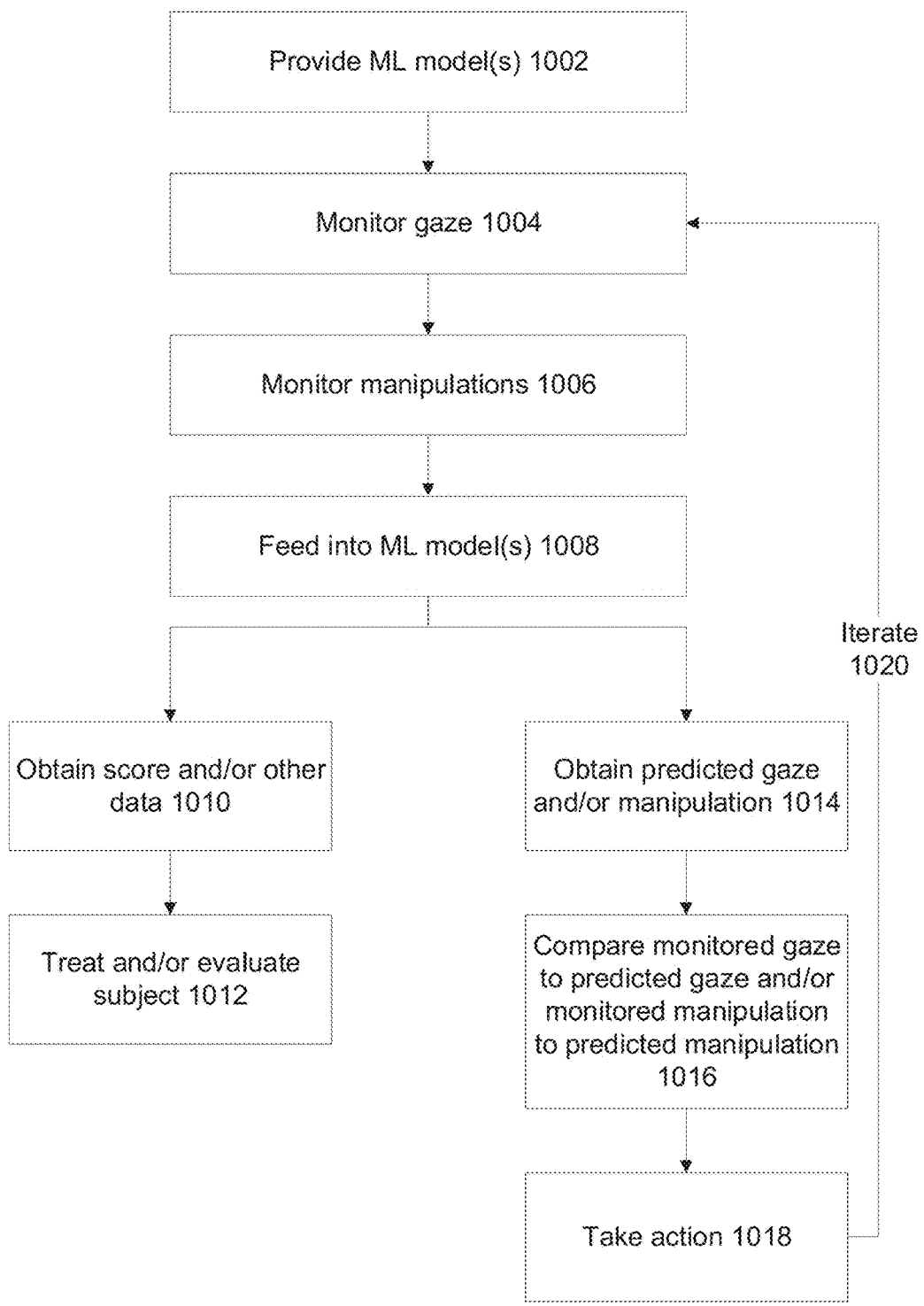
FIG. 10 is a flowchart of a method of inference by a machine learning model trained on a training dataset of images annotated with indications of monitored gaze and/or monitored manipulations, in accordance with various embodiments.

Reference is now made to FIG. 10, which is a flowchart of a method of inference by a machine learning model trained on a training dataset of images annotated with indications of monitored gaze and/or monitored manipulations, in accordance with some embodiments of the present invention. At 1002, one or more machine learning models are provided. Machine learning models are trained, for example, using the approach described with reference to FIG. 9, such as with respect to 922 of FIG. 9.

At 1004, a gaze of a user viewing a target image of a sample, is monitored in real time. Example of approaches for monitoring gaze and/or are described, for example, with reference to 904 of FIG. 9.

At 1006, manipulations of a presentation of a sample by a user may be monitored in real time. The manipulations may be of the user adjusting settings of the microscope, and/or adjusting the presentation of the image of the sample on a display. Examples of samples are described, for example, with reference to 902 of FIG. 9. The sample may be placed under a microscope for viewing by the user. Example of approaches for monitoring manipulations and/or exemplary manipulations are described, for example, with reference to 908 of FIG. 9.

At 1008, the target image of the sample is fed into the machine learning model(s). Optionally, the monitored gaze of the user viewing the sample is fed into the machine learning model in addition to the target image. Alternatively or additionally, the monitored manipulations performed by the user fed into the machine learning model in addition to the target image. Alternatively or additionally, one or more other data items are fed into the machine learning model in addition to the target image, such as tissue type and/or medical history, for example, as described with reference to 916 of FIG. 9.

The image of the sample may be obtained, for example, by scanning a slide of pathological tissue to create a WSI, and/or capturing a high resolution image of the manufactured object. When the sample is a live cell culture, the image may be obtained, for example, by a high resolution camera and/or a camera connected to the microscope. The user may view the image of the sample on a display. Additional exemplary details of obtaining the image of the sample are described, for example, with reference to 910 of FIG. 9.

Different outcomes may be generated, according to the training dataset used to train the machine learning model(s) and/or according to the input fed into the machine learning model, for example, as described with reference to 922 of FIG. 9. Examples of processes based on the outcome of the machine learning models are described with reference to 1010-1012 which relates to diagnosis and/or treatment of the subject, and 1014-1018 which relates to training of new users and/or quality control of users.

At 1010, a sample score (e.g., visual evaluation score) indicating, for example, a pathological/radiological evaluation for the sample (e.g., biological sample, tissue sample, radiology image and/or live cell culture), and/or a pass/fail quality assurance test outcome (e.g., for a manufactured object) and/or other examples of data described with reference to 916 of FIG. 9, may be obtained as an outcome of the machine learning model.

At 1012, in the case of a medical sample (e.g., biological sample, tissue sample, radiology image and/or live cell culture) the subject may be treated and/or evaluated according to the sample score. For example, the subject may be administered chemotherapy when the sample score is above a threshold, the subject may undergo surgery when the pathological diagnosis indicates a certain type of cancer, and the like. In the case of a manufactured object (e.g., microarray), the object may be further processed when the sample score indicates a pass and/or no significant manufacturing defects of a quality assurance test, and/or the object may be rejected when the sample score indicates a fail and/or significant manufacturing defects of the quality assurance test.

Alternatively or additionally to 1010-1012, at 1014, an indication of predicted gaze and/or predicted manipulation is obtained as an outcome of the machine learning model. The predicted monitored gaze may be, for example, per pixel and/or per group of pixels and/or per region of the target image. The predicted manipulations may be for the image as a whole and/or for the current FOV, for example, to zoom in, and/or to pan the view.

The monitored gaze may be represented as a heatmap. The heatmap may include multiple pixels mapped to pixels of the target image. Intensity of pixels of the heatmap correlate to a predicted time for gazing. Additional exemplary details of the heatmap are described, for example, with reference to 908 of FIG. 9.

The predicted gaze may be presented on a display, for example, as an overlay over the image of the sample.

The predicted monitored gaze and/or predicted manipulations may be represented as a time series indicating dynamic gaze mapped to pixels of the target image over a time interval and/or manipulations performed during different times of the time interval.

At 1016, the real time monitoring of manipulation is compared to the prediction of manipulations, and/or the real time of the gaze is compared to the prediction of the gaze.

The comparison may performed, for example, by computing a difference, for example, indicating an amount of similarity and/or dissimilarity. For example, number of pixels between the predicted gaze and the actual gaze. In another example, comparing a difference between the real time monitoring and the time series, and generating an alert when the difference is above a threshold.

At 1018, one or more actions may be taken. Actions may be taken when the difference is above a threshold, and/or when the difference indicates statistical dissimilarity. For example, an alert may be generated, and/or instructions may be generated, for example, presented on the display, played as a video, presented as an image, presented as text, and/or played as an audio file over speakers. The instructions may indicate to the user that their manipulation and/or gaze are different than expected. Such instructions may be provided, for example, for training of new domain experts and/or to monitor trained domain experts as a form of quality control, such as to help make sure the domain experts are following standard practice. Instructions may indicate what the predicted gaze and/or manipulations are, so that the user is able to follow the instructions.

In another example, the instructions indicating the predicted gaze and/or predicted manipulations are provided without necessarily monitoring the user's current gaze and/or manipulations, for example, to guide the user in the process of evaluating the sample.

At 1020, one or more features described with reference to 1004-1008 and/or 1014-1018 are iterated during the viewing session, for example, for dynamically guiding the user's gaze and/or manipulations for evaluating the sample, and/or for continuous real time training and/or quality control.

Figure 12:
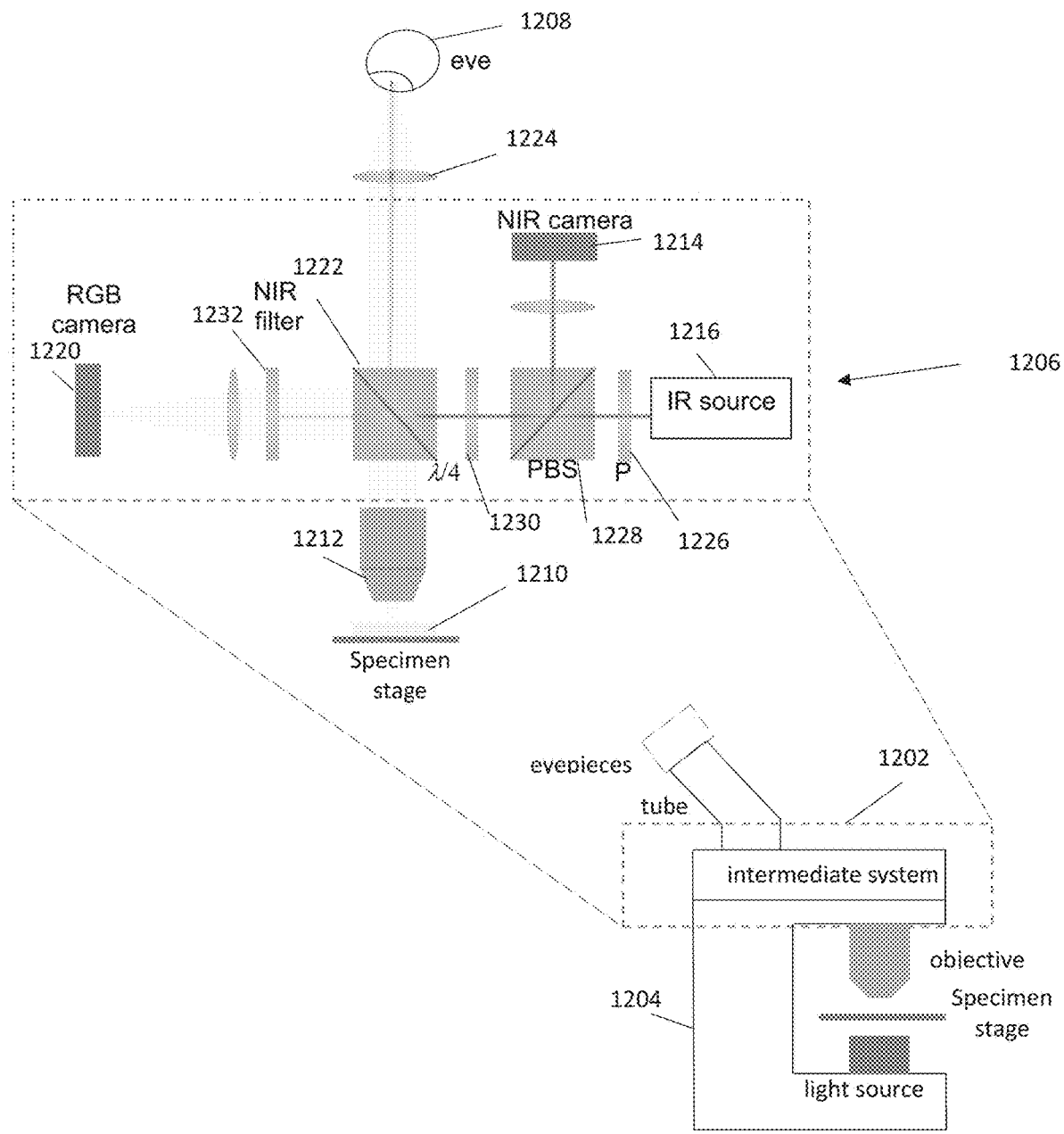
FIG. 12 is a schematic of a component for installation on a microscope for monitoring gaze of a user viewing a sample under the microscope, in accordance with various embodiments.

Reference is now made to FIG. 12, which is a schematic of a component 1202 for installation on a microscope 1204 for monitoring gaze of a user viewing a sample (e.g., biological sample, live cell sample, tissue sample, or a manufactured object such as microarray) under the microscope, in accordance with some embodiments of the present invention. Component 1202 may be integrated with microscope 1204, and/or designed to be connected and/or disconnected from microscope 1204.

Component 1202 is installed between an objective lens 1212 and eyepiece 1224 of microscope 1204.

Component 1202 is designed to not affect (or not significantly affect) the user optical path and/or user viewing experience and/or user workflow using the microscope by the addition of component 1202. The infinity corrected scheme may not affect the optical path and/or experience and/or workflow.

Component 1202 may include: an optical arrangement 1206 that directs a first set of electromagnetic frequencies back-reflected from an eye 1208 of a user viewing a sample 1210 under microscope objective lens 1212 to a camera 1214 that generates an indication of tracked gaze of the user. The first set of electromagnetic frequencies may be infrared (IR) frequencies generated by an IR source 1216. Camera 1214 may be a near IR (NIR) camera. Optical arrangement 1206 simultaneously directs a second set of electromagnetic frequencies from sample 1210 to a camera 1220 that captures images depicting a field of view the user is viewing.

The first and the second set of electromagnetic frequencies may include the visible light spectrum. Camera 1220 may be a red-green-blue (RGB) camera.

Optical arrangement 1206 may include a beam splitter 1222 that directs the first set of electromagnetic frequencies from IR source 1216 to eyepiece 1224 where eye of the user 1208 is located. Beam splitter 1222 simultaneously directs the back-reflected first set of electromagnetic frequencies from eye of the user 1208 via eyepiece 1224 to NIR camera 1214, and directs the second set of electromagnetic frequencies from sample 1210 to camera 1220 and to eyepiece 1224.

During the path from IR source 1216, the IR frequencies pass through linear polarizer set along a plane of incidence (P) 1226, polarized beam splitting (PBS) 1228, and $\lambda/4$ 1230. PBS 1228 enables the IR energy to pass from IR source 1216 to beam splitter 1222, but prevents IR energy from passing back to IR source 1216, and instead reflects the IR energy to NIR camera 1214. A NIR filter 1232 is located on the optical path from beam splitter 1222 to RGB camera 1220 to prevent reflected IR energy from reaching RGB camera 1220. Optical arrangement may include P, linear polarizer set along the plane of incidence, $\lambda/4$, quarter wave-plate, which transform linear polarization to circular polarization, serve as an optical isolator that prevent from IR back reflected light set normal to the plane of incidence after passing back through $\lambda/4$, to enter the IR light source and direct it to the IR camera.

It is noted that although a single 1208 a single eyepiece 1224 is shown, in practice, the user uses both eyes and two eyepieces. Optical arrangement 1206 separates the electromagnetic light waves from a single optical path after reflection from two eyes to two optical paths to two of the IR cameras 1216 may be implemented, for example, as one or more of: polarizers and/or waveplates that direct different polarized light to different paths, and/or using infrared spectral light sources, shifted in a certain wavelength, with dichroic mirrors and spectral filters, and/or adding amplitude modulation in different frequencies for each optical path for heterodyne detection.

Various embodiments provide tools and techniques for implementing annotation data collection, and, more particularly, to methods, systems, and apparatuses for implementing annotation data collection using gaze-based tracking, in some cases, for training an artificial intelligence ("AI") system (which might include, without limitation, at least one of a neural network, a convolutional neural network ("CNN"), a learning algorithm-based system, or a machine learning system, and/or the like).

In various embodiments, a first camera might capture at least one first image of at least one eye of a user, as the user is looking at an optical view of a first sample. A computing system might analyze the captured at least one first image of the at least one eye of the user and at least one second image of the optical view of the first sample to determine whether the at least one eye of the user is focused on a particular region of the optical view of the first sample. Based on a determination that the at least one eye of the user is focused on a particular region of the optical view of the first sample, the computing system might identify at least one particular portion of the at least one second image corresponding to the particular region of the optical view of the first sample. The computing system might generate collect attention data comprising the identified at least one particular portion of the at least one second image, and might store the collected attention data in a database 110a or 110b. According to some embodiments, collecting the attention data might be performed without interrupting, slowing, or encumbering the user as the user is providing the outcome data either while diagnosing the first sample using microscope 115 or while diagnosing an image of the first sample as displayed on a display screen 120. In some instances, the collected attention data might include, but is not limited to, at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample, and/or the like. In some cases, the identified at least one particular portion of the at least one second image corresponding to the particular region of the optical view of the first sample might include, without limitation, at least one of one or more specific cells, one or more specific tissues, one or more specific structures, or one or more molecules, and/or the like.

In some embodiments, the computing system might at least one highlighting field in the at least one second image covering the identified at least one particular portion of the at least one second image corresponding to the particular region of the optical view of the first sample. In some cases, the at least one highlighting field might each include, without limitation, at least one of a color, a shape, or a highlighting effect, and/or the like, where the highlighting effect might include, but is not limited to, at least one of outlining effect, shadowing effect, patterning effect, heat map effect, or jet colormap effect, and/or the like.

According to some embodiments, the at least one second image might be displayed on a display screen. Capturing the at least one first image of the at least one eye of the user might comprise capturing, with camera, the at least one first image of the at least one eye of the user, as the user is looking at the image(s) or video(s) of the optical view of the first sample as displayed on the display screen of the display device as the at least one second image. Alternative to camera, a gaze tracking device might be used to collect attention data, as the user is looking at the images or videos of the first sample that are displayed on the display screen of the display device. Identifying the at least one particular portion of the at least one second image corresponding to the particular region of the optical view of the first sample might comprise identifying, with the computing system, at least one particular portion of the at least one second image as displayed on the display screen corresponding to the particular region of the optical view of the first sample. The computing system might display, on the display screen, the at least one second image with the generated at least one highlighting field covering the identified at least one particular portion of the at least one second image corresponding to the particular region of the optical view of the first sample.

In some embodiments, the display of the at least one second image on the display screen may be shifted in response to commands by the user. In some instances, shifting display of the at least one second image might comprise at least one of horizontal shifting, vertical shifting, panning, tilting, zooming in, or zooming out, and/or the like, of the at least one second image on the display screen. The first camera might track movement of the at least one eye of the user, as the user is looking at the shifting display of the at least one second image on the display screen. The computing system might match the tracked movement of the at least one eye of the user with the shifting display of the at least one second image on the display screen, based at least in part on one or more of the tracked movement of the at least one eye of the user, the identified at least one particular portion of the at least one second image corresponding to the particular region of the optical view of the first sample, or the at least one of horizontal shifting, vertical shifting, panning, tilting, zooming in on, or zooming out of the at least one second image on the display screen, and/or the like. Alternative to using camera, the gaze tracking device might be used to collect additional attention data, as the user is looking at the shifting display of the at least one second image on the display screen of display device.

Alternatively, a microscope might project the optical view of the first sample to an eyepiece lens through which the at least one eye of the user is viewing. A second camera might capture the at least one second image of the optical view of the first sample. In some cases, capturing the at least one first image of the at least one eye of the user might comprise capturing, with the first camera, the at least one first image of the at least one eye of the user, as the user is looking at the optical view of the first sample through the eyepiece lens. Identifying the at least one particular portion of the at least one second image corresponding to the particular region of the optical view of the first sample might comprise identifying, with the computing system, at least one particular portion of the at least one second image as viewed through the eyepiece lens corresponding to the particular region of the optical view of the first sample. In some cases, the computing system might display, on the display screen, the at least one second image with the generated at least one highlighting field covering the identified at least one particular portion of the at least one second image corresponding to the particular region of the optical view of the first sample.

In some instances, the first camera might be one of an infrared ("IR") camera, a back-reflected IR camera, a visible-color camera, a light source, or a location photodiode, and/or the like. In some cases, the microscope might include, without limitation, two or more of a plurality of mirrors, a plurality of dichroic mirrors, or a plurality of half-mirrors that reflect or pass-through at least one of the optical view of the first sample as viewed through the eyepiece lens, an optical view of the at least one eye of the user as viewed through the eyepiece lens and as captured by the first camera as the at least one first image, or projection of the generated at least one highlighting field through the eyepiece lens to the at least one eye of the user, and/or the like.

According to some embodiments, projection of the optical view of the first sample to the eyepiece lens may be shifted, by at least one of adjusting an X-Y stage on which a microscope slide containing the first sample, exchanging objective or zoom lenses, or adjusting focus of the eyepiece lens, and/or the like. The first camera might track movement of the at least one eye of the user, as the user is looking at the shifting projection of the optical view of the first sample to the eyepiece lens. The computing system might match the tracked movement of the at least one eye of the user with the shifting projection of the optical view of the first sample to the eyepiece lens, based at least in part on one or more of the tracked movement of the at least one eye of the user, the identified at least one particular portion of the at least one second image corresponding to the particular region of the optical view of the first sample, or the at least one of adjusting an X-Y stage on which a microscope slide containing the first sample, exchanging objective or zoom lenses, or adjusting focus of the eyepiece lens, and/or the like.

Alternatively, or additionally, one or more audio sensors might capture one or more verbal notes from the user, as the user is looking at the optical view of the first sample. The computing system might map the captured one or more verbal notes from the user with the at least one second image of the optical view of the first sample to match the captured one or more verbal notes with the at least one second image of the optical view of the first sample.

According to some embodiments, the computing system might receive outcome data provided by the user, the outcome data comprising at least one of a diagnosis of the first sample, a pathology score of the first sample, or a set of identification data corresponding to at least portions of the first sample. The computing system might train an AI system (which might generally include, without limitation, at least one of a neural network, a convolutional neural network ("CNN"), a learning algorithm-based system, or a machine learning system, and/or the like), based at least in part on at least one of analysis of the captured at least one first image of the at least one eye of the user and the at least one second image of the optical view of the first sample or joint analysis of the collected attention data together with the received outcome data, to generate a model that is used to generate a predicted value. In some embodiments, the predicted value might include, but is not limited to, at least one of a predicted clinical outcome or predicted attention data, and/or the like.

In accordance with the various embodiments described herein, the annotation data collection system described herein allows for recording a user's (e.g., a pathologist's) visual attention in addition to tracking of microscope FOVs during the scoring process, and therefore provides highly localized spatial information that supports the overall score for the slide. This information will be used to develop algorithms for tumor localization, classification, and digital scoring in WSI, or the like. Algorithms may also be developed for ROI localization, classification, and digital scoring in WSI other than tumors.

These and other aspects of the annotation data collection system using gaze-based tracking and/or training of an AI system based on annotation data collected using gaze-based tracking are described in greater detail with respect to the figures.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Various embodiments described herein, while embodying (in some cases) software products, computer-performed methods, and/or computer systems, represent tangible, concrete improvements to existing technological areas, including, without limitation, annotation collection technology, annotation data collection technology, and/or the like. In other aspects, certain embodiments, can improve the functioning of user equipment or systems themselves (e.g., annotation collection system, annotation data collection system, etc.), for example, by capturing, with a first camera, at least one first image of at least one eye of a user, as the user is looking at an optical view of a first sample; capturing, with a second camera, at least one second image of the optical view of the first sample; analyzing, with a computing system, the captured at least one first image of the at least one eye of the user and the captured at least one second image of the optical view of the first sample to determine whether the at least one eye of the user is focused on a particular region of the optical view of the first sample; based on a determination that the at least one eye of the user is focused on a particular region of the optical view of the first sample, identifying, with the computing system, at least one particular portion of the at least one second image corresponding to the particular region of the optical view of the first sample; collecting, with the computing system, attention data comprising the identified at least one particular portion of the at least one second image; storing, in a database, the collected attention data; receiving, with the computing system, outcome data provided by the user, the outcome data comprising at least one of a diagnosis of the first sample, a pathology score of the first sample, or a set of identification data corresponding to at least portions of the first sample; and training at least one of a neural network, a convolutional neural network ("CNN"), an artificial intelligence ("AI") system, or a machine learning system, based at least in part on at least one of analysis of the captured at least one first image of the at least one eye of the user and the captured at least one second image of the optical view of the first sample or joint analysis of the collected attention data together with the received outcome data, to generate a model that is used to generate a predicted value (e.g., at least one of a predicted clinical outcome or predicted attention data, or the like); and/or the like.

In particular, to the extent any abstract concepts are present in the various embodiments, those concepts can be implemented as described herein by devices, software, systems, and methods that involve specific novel functionality (e.g., steps or operations), such as, capturing, with a first camera, at least one first image of at least one eye of a user, as the user is looking at an optical view of a first sample; capturing, with a second camera, at least one second image of the optical view of the first sample; analyzing, with a computing system, the captured at least one first image of the at least one eye of the user and the captured at least one second image of the optical view of the first sample to determine whether the at least one eye of the user is focused on a particular region of the optical view of the first sample; based on a determination that the at least one eye of the user is focused on a particular region of the optical view of the first sample, identifying, with the computing system, at least one particular portion of the at least one second image corresponding to the particular region of the optical view of the first sample; collecting, with the computing system, attention data comprising the identified at least one particular portion of the at least one second image; storing, in a database, the collected attention data; receiving, with the computing system, outcome data provided by the user, the outcome data comprising at least one of a diagnosis of the first sample, a pathology score of the first sample, or a set of identification data corresponding to at least portions of the first sample; and training at least one of a neural network, a convolutional neural network ("CNN"), an artificial intelligence ("AI") system, or a machine learning system, based at least in part on at least one of analysis of the captured at least one first image of the at least one eye of the user and the captured at least one second image of the optical view of the first sample or joint analysis of the collected attention data together with the received outcome data, to generate a model that is used to generate a predicted value (e.g., at least one of a predicted clinical outcome or predicted attention data, or the like); and/or the like, to name a few examples, that extend beyond mere conventional computer processing operations. These functionalities can produce tangible results outside of the implementing computer system, including, merely by way of example, allows for recording a user's visual attention in addition to tracking of FOVs of samples during visual analysis by the user, and therefore provides highly localized spatial information that supports the overall annotation of the samples as analyzed by the user, and, in some cases, this information will be used to develop algorithms for sample region of interest ("ROI") localization, classification, and digital scoring of the sample, or the like, at least some of which may be observed or measured by users and/or service providers.

In an aspect, a method might comprise projecting, with a microscope, an optical view of a first sample to an eyepiece lens through which at least one eye of a user is viewing; capturing, with a first camera, at least one first image of the at least one eye of the user, as the user is looking at the optical view of the first sample through the eyepiece lens; capturing, with a second camera, at least one second image of the optical view of the first sample; analyzing, with a computing system, the captured at least one first image of the at least one eye of the user and the captured at least one second image of the optical view of the first sample to determine whether the at least one eye of the user is focused on a particular region of the optical view of the first sample; based on a determination that the at least one eye of the user is focused on a particular region of the optical view of the first sample, identifying, with the computing system, at least one particular portion of the at least one second image as viewed through the eyepiece lens corresponding to the particular region of the optical view of the first sample; collecting, with the computing system, attention data comprising the identified at least one particular portion of the at least one second image; and storing, in a database, the collected attention data.

In some embodiments, the first sample may be contained within at least one of a microscope slide, a transparent sample cartridge, a vial, a tube, a capsule, a flask, a vessel, a receptacle, a microarray, or a microfluidic chip, and/or the like. In some cases, the first camera might be one of an infrared ("IR") camera, a back-reflected IR camera, a visible-color camera, a light source, or a location photodiode, and/or the like. In some instances, the microscope might comprise two or more of a plurality of mirrors, a plurality of dichroic mirrors, or a plurality of half-mirrors that reflect or pass-through at least one of the optical view of the first sample as viewed through the eyepiece lens or an optical view of the at least one eye of the user as viewed through the eyepiece lens and as captured by the first camera as the at least one first image.

According to some embodiments, the identified at least one particular portion of the at least one second image corresponding to the particular region of the optical view of the first sample might comprise at least one of one or more specific cells, one or more specific tissues, one or more specific structures, or one or more molecules, and/or the like. In some instances, identifying the at least one particular portion of the at least one second image might comprise determining, with the computing system, coordinate locations within the at least one second image of the optical view corresponding to the identified at least one particular portion of the at least one second image.

In some embodiments, the method might further comprise receiving, with the computing system, outcome data provided by the user, the outcome data comprising at least one of a diagnosis of the first sample, a pathology score of the first sample, or a set of identification data corresponding to at least portions of the first sample; and training at least one of a neural network, a convolutional neural network ("CNN"), an artificial intelligence ("AI") system, or a machine learning system, based at least in part on at least one of analysis of the captured at least one first image of the at least one eye of the user and the captured at least one second image of the optical view of the first sample or joint analysis of the collected attention data together with the received outcome data, to generate a model that is used to generate a predicted value. In some cases, the predicted value might comprise at least one of a predicted clinical outcome or predicted attention data, and/or the like. In some instances, collecting the attention data might be performed without interrupting, slowing, or encumbering the user as the user is providing the outcome data while diagnosing the first sample using the microscope.

According to some embodiments, the method might further comprise tracking, with the first camera, movement of the at least one eye of the user; and concurrently tracking, with the computing system, at least one of one or more coordinate locations of the identified at least one particular portion of the at least one second image, attention duration of the user's focus on the particular region of the optical view, or zoom level of the optical view of the first sample during the user's focus on the particular region of the optical view. In some cases, determining whether the at least one eye of the user is focused on a particular region of the optical view of the first sample might comprise determining whether the at least one eye of the user is focused on a particular region of the optical view of the first sample, based at least in part on at least one of the one or more coordinate locations of the identified at least one particular portion of the at least one second image, the attention duration of the user's focus on the particular region of the optical view, or the zoom level of the optical view of the first sample during the user's focus on the particular region of the optical view.

In some embodiments, the method might further comprise capturing, with an audio sensor, one or more verbal notes from the user, as the user is looking at the optical view of the first sample; and mapping, with the computing system, the captured one or more verbal notes from the user with the at least one second image of the optical view of the first sample to match the captured one or more verbal notes with the at least one second image of the optical view of the first sample.

In another aspect, a system might comprise a microscope, a first camera, a second camera, and a computing system. The microscope might be configured to project an optical view of a first sample to an eyepiece lens through which at least one eye of a user is viewing. The first camera might be configured to capture at least one first image of the at least one eye of the user, as the user is looking at the optical view of the first sample through the eyepiece lens. The second camera might be configured to capture at least one second image of the optical view of the first sample. The computing system might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to: analyze the captured at least one first image of the at least one eye of the user and the captured at least one second image of the optical view of the first sample to determine whether the at least one eye of the user is focused on a particular region of the optical view of the first sample; based on a determination that the at least one eye of the user is focused on a particular region of the optical view of the first sample, identify at least one particular portion of the at least one second image as viewed through the eyepiece lens corresponding to the particular region of the optical view of the first sample; collect attention data comprising the identified at least one particular portion of the at least one second image; and store, in a database, the collected attention data.

In some embodiments, the first set of instructions, when executed by the at least one first processor, further causes the computing system to: receive outcome data provided by the user, the outcome data comprising at least one of a diagnosis of the first sample, a pathology score of the first sample, or a set of identification data corresponding to at least portions of the first sample; and train at least one of a neural network, a convolutional neural network ("CNN"), an artificial intelligence ("AI") system, or a machine learning system, based at least in part on at least one of analysis of the captured at least one first image of the at least one eye of the user and the captured at least one second image of the optical view of the first sample or joint analysis of the collected attention data together with the received outcome data, to generate a model that is used to generate a predicted value. In some cases, the predicted value might comprise at least one of a predicted clinical outcome or predicted attention data, and/or the like. In some instances, the first camera might be further configured to track movement of the at least one eye of the user. In some cases, the computing system might be further configured to concurrently track at least one of one or more coordinate locations, attention duration, or zoom level of the optical view of the first sample.

According to some embodiments, determining whether the at least one eye of the user is focused on a particular region of the optical view of the first sample might comprise determining whether the at least one eye of the user is focused on a particular region of the optical view of the first sample, based at least in part on one or more of tracking of the one or more coordinate locations of attention gaze, tracking of the at least one of movement and zoom level of the optical view of the first sample, or a determination that the at least one eye of the user is lingering on a portion of the optical view of the first sample.

In some embodiments, the system might further comprise an audio sensor configured to capture one or more verbal notes from the user, as the user is looking at the optical view of the first sample. The first set of instructions, when executed by the at least one first processor, might cause the computing system to: map the captured one or more verbal notes from the user with the at least one second image of the optical view of the first sample to match the captured one or more verbal notes with the at least one second image of the optical view of the first sample.

In yet another aspect, a method might comprise receiving at least one first image of at least one eye of a user that is captured by a first camera, as the user is looking at an optical view of a first sample through an eyepiece lens of a microscope; receiving at least one second image of the optical view of the first sample that is captured by a second camera; analyzing, with a computing system, the at least one first image and the at least one second image to determine whether the at least one eye of the user is focused on a particular region of the optical view of the first sample; tracking, with the computing system, attention of the user based on the analysis; and collecting, with the computing system, attention data based on the tracking.

In an aspect, a method might comprise receiving, with a computing system, collected attention data corresponding to a user looking at an optical view of a first sample; receiving, with the computing system, outcome data provided by the user, the outcome data comprising at least one of a diagnosis of the first sample, a pathology score of the first sample, or a set of identification data corresponding to at least portions of the first sample; and training at least one of a neural network, a convolutional neural network ("CNN"), an artificial intelligence ("AI") system, or a machine learning system, based at least in part on joint analysis of the collected attention data together with the received outcome data, to generate a model that is used to generate a predicted value.

In some embodiments, the first sample might be contained within at least one of a microscope slide, a transparent sample cartridge, a vial, a tube, a capsule, a flask, a vessel, a receptacle, a microarray, or a microfluidic chip, and/or the like. In some cases, the predicted value might comprise at least one of a predicted clinical outcome or predicted attention data, and/or the like.

According to some embodiments, collecting the attention data might be performed without interrupting, slowing, or encumbering the user as the user is providing the outcome data either while diagnosing the first sample using a microscope or while diagnosing an image of the first sample as displayed on a display screen. In some instances, the collected attention data might comprise at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample, and/or the like.

In some embodiments, the attention data might be collected based on at least one first image of the at least one eye of the user that is captured by a first camera as the user is looking at the optical view of the first sample through an eyepiece lens of a microscope. In some cases, the microscope might comprise two or more of a plurality of mirrors, a plurality of dichroic mirrors, or a plurality of half-mirrors that reflect or pass-through at least one of the optical view of the first sample as viewed through the eyepiece lens or an optical view of the at least one eye of the user as viewed through the eyepiece lens and as captured by the first camera as the at least one first image.

Alternatively, the attention data might be collected using a gaze tracking device, as the user is looking at a first image of the optical view of the first sample that is displayed on a display screen. In some embodiments, the method might further comprise generating, with the computing system, at least one highlighting field for overlapping with identified at least one particular portion of the at least one first image as displayed on the display screen corresponding to a particular region of the optical view of the first sample. In some instances, the method might further comprise displaying, with the computing system and on the display screen, the generated at least one highlighting field to overlap with the identified at least one particular portion of the at least one first image as displayed on the display screen corresponding to the collected attention data; tracking, with the gaze tracking device, the attention data, as the user is looking at the first image of the optical view of the first sample as displayed on the display screen; and matching, with the computing system, the tracked attention data with the display of the at least one first image of the optical view of the first sample as displayed on the display screen, based at least in part on at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample. In some cases, the at least one highlighting field might each comprise at least one of a color, a shape, or a highlighting effect, and/or the like. The highlighting effect might comprise at least one of outlining effect, shadowing effect, patterning effect, heat map effect, or jet colormap effect, and/or the like.

According to some embodiments, the method might further comprise tracking, with a gaze tracking device, attention data; and concurrently tracking, with the computing system, at least one of one or more coordinate locations of identified at least one particular portion of at least one second image of the optical view of the first sample, attention duration of the user's focus on a particular region of the optical view, or zoom level of the optical view of the first sample during the user's focus on the particular region of the optical view.

In some embodiments, the method might further comprise capturing, with an audio sensor, one or more verbal notes from the user, as the user is looking at the optical view of the first sample; and mapping, with the computing system, the captured one or more verbal notes from the user with at least one third image of the optical view of the first sample to match the captured one or more verbal notes with the at least one third image of the optical view of the first sample.

In another aspect, an apparatus might comprise at least one processor and a non-transitory computer readable medium communicatively coupled to the at least one processor. The non-transitory computer readable medium might have stored thereon computer software comprising a set of instructions that, when executed by the at least one processor, causes the apparatus to: receive collected attention data corresponding to a user looking at an optical view of a first sample; receive outcome data provided by the user, the outcome data comprising at least one of a diagnosis of the first sample, a pathology score of the first sample, or a set of identification data corresponding to at least portions of the first sample; and train at least one of a neural network, a convolutional neural network ("CNN"), an artificial intelligence ("AI") system, or a machine learning system, based at least in part on joint analysis of the collected attention data together with the received outcome data, to generate a model that is used to generate a predicted value.

In yet another aspect, a system might comprise a first camera, a second camera, and a computing system. The first camera might be configured to capture at least one first image of the at least one eye of the user, as the user is looking at the optical view of the first sample. The second camera might be configured to capture at least one second image of the optical view of the first sample. The computing system might comprise at least one first processor and a first non-transitory computer readable medium communicatively coupled to the at least one first processor. The first non-transitory computer readable medium might have stored thereon computer software comprising a first set of instructions that, when executed by the at least one first processor, causes the computing system to: receive collected attention data corresponding to a user looking at the optical view of the first sample; receive outcome data provided by the user, the outcome data comprising at least one of a diagnosis of the first sample, a pathology score of the first sample, or a set of identification data corresponding to at least portions of the first sample; and train at least one of a neural network, a convolutional neural network ("CNN"), an artificial intelligence ("AI") system, or a machine learning system, based at least in part on joint analysis of the collected attention data together with the received outcome data, to generate a model that is used to generate a predicted value.

Various modifications and additions can be made to the embodiments discussed without departing from the scope of the invention. For example, while the embodiments described above refer to particular features, the scope of this invention also includes embodiments having different combination of features and embodiments that do not include all of the above described features.

We now turn to the embodiments as illustrated by the drawings. FIGS. 1-12 illustrate some of the features of the method, system, and apparatus for implementing annotation data collection, and, more particularly, to methods, systems, and apparatuses for implementing annotation data collection using gaze-based tracking and/or training of an artificial intelligence ("AI") system based on annotation data collected using gaze-based tracking, as referred to above. The methods, systems, and apparatuses illustrated by FIGS. 1-7 refer to examples of different embodiments that include various components and steps, which can be considered alternatives or which can be used in conjunction with one another in the various embodiments. The description of the illustrated methods, systems, and apparatuses shown in FIGS. 1-12 is provided for purposes of illustration and should not be considered to limit the scope of the different embodiments.

With reference to the figures, FIG. 1 is a schematic diagram illustrating a system 100 for implementing annotation data collection using gaze-based tracking, in accordance with various embodiments.

In the non-limiting embodiment of FIG. 1, system 100 might comprise a computing system 105a and a data store or database 110a that is local to the computing system 105a. In some cases, the database 110a might be external, yet communicatively coupled, to the computing system 105a. In other cases, the database 110a might be integrated within the computing system 105a. System 100, according to some embodiments, might further comprise a microscope 115 and/or a display device 120 that might allow a user 125 to view a sample (e.g., sample 170, or the like) or an image(s) or video(s) of the sample. System 100 might further comprise a camera(s) 130, one or more audio sensors 135 (optional), and one or more user devices 140 (optional). The camera 130 might capture images or videos of the user 125 (in some cases, capturing images or videos of at least one eye of the user 125) while the user 125 is within the field of view ("FOV") 130a of camera 130. In some instances, the camera 130 might include, without limitation, one or more eye tracking sensors, one or more motion sensors, or one or more tracking sensors, and/or the like. Alternative to the camera 130, gaze tracking device (not shown in FIG. 1) might be used to collect attention data, as the user is looking at an optical view of the first sample through an eyepiece lens of the microscope 115 or looking at the images or videos of the first sample that are displayed on the display screen of the display device 120. In some cases, the one or more audio sensors 135 might include, but is not limited to, one or more microphones, one or more voice recorders, or one or more audio recorders, and/or the like. In some instances, the one or more user devices 140 might include, without limitation, smart phones, mobile phones, tablet computers, laptop computers, desktop computers, or monitors, and/or the like. Computing system 105a might communicatively couple (either via wireless (as depicted by lightning bolt symbols, or the like) or wired connection (as depicted by connecting lines)) with one or more of the microscope 115, the display device 120, the camera 130 (or the gaze tracking device), the one or more audio sensors 135, and/or the one or more user devices 140. Computing system 105a, database(s) 110a, microscope 115, display device 120, user 125, camera 130 (or the gaze tracking device), audio sensors 135, and/or user devices 140 might be disposed or located within work environment 145, which might include, but is not limited to, one of a laboratory, a clinic, a medical facility, a research facility, or a room, and/or the like.

System 100 might further comprise remote computing system 105b (optional) and corresponding database(s) 110b (optional) that might communicatively couple with computing system 105a via network(s) 150. In some cases, system 100 might further comprise artificial intelligence ("AI") system 105c that might communicatively couple with computing system 105a or remote computing system 105b via network(s) 150. In some embodiments, the AI system 105c might include, but is not limited to, at least one of a machine learning system(s), a learning algorithm-based system(s), or a neural network system(s), and/or the like.

Merely by way of example, network(s) 150 might each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, network(s) 150 might each include an access network of an Internet service provider ("ISP"). In another embodiment, network(s) 150 might each include a core network of the ISP, and/or the Internet.

According to some embodiments, the microscope 115 might include, without limitation, at least one of a processor 155, a data store 160a, a user interface device(s) 160b (e.g., touchscreen(s), buttons, keys, switches toggles, knobs, dials, etc.), a microscope stage 165a (e.g., X-Y stage or X-Y-Z stage, or the like), a first motor 165b (for autonomously controlling X-direction movement of the microscope stage), a second motor 165c (for autonomously controlling Y-direction movement of the microscope stage), a third motor 165d (optional; for autonomously controlling Z-direction movement of the microscope stage), a light source 165e (e.g., a lamp for backlighting samples contained in a microscope slide placed on the microscope stage, etc.), one or more objective or zoom lenses 165f, a sample 170 (which, if present, may be contained in or on a microscope slide mounted on the microscope stage 165a), a FOV camera 175, an eyepiece lens(es) 180, a gaze camera 185, a projection device 190 (optional), a wired communications system 195a, and a transceiver 195b. The processor 155 might communicatively couple with at least one of the data store 160a, the user interface device(s) 160b, the first motor 165b, the second motor 165c, the third motor 165d, the FOV camera 175, the gaze camera 185, the projection device 190, the wired communications system 195a, or the transceiver 195, and/or the like.

In operation, the microscope 115 might project an optical view of a first sample 170 to eyepiece lens(es) 180 through which at least one eye of user 125 is viewing. The camera 130 (or gaze tracking device) or gaze camera 185 might capture at least one first image of at least one eye of the user 125, as the user 125 is looking at an optical view of a first sample (whether projected through the eyepiece lens(es) 180 of the microscope 115 or displayed on a display screen of display device 120, or the like). Computing system 105a, user device(s) 140, remote computing system(s) 105b, and/ or processor 155 (if the microscope is being used) (collectively, "computing system" or the like) might analyze the captured at least one first image of the at least one eye of the user 125 and the captured at least one second image of the optical view of the first sample to determine whether the at least one eye of the user 125 is focused on a particular region of the optical view of the first sample. Based on a determination that the at least one eye of the user 125 is focused on a particular region of the optical view of the first sample, the computing system might identify at least one particular portion of the at least one second image corresponding to the particular region of the optical view of the first sample. The computing system might collect attention data comprising the identified at least one particular portion of the at least one second image, and might store the collected attention data in a database 110a or 110b. According to some embodiments, collecting the attention data might be performed without interrupting, slowing, or encumbering the user as the user is providing the outcome data either while diagnosing the first sample using microscope 115 or while diagnosing an image of the first sample as displayed on a display screen 120. In some instances, the collected attention data might include, but is not limited to, at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample, and/or the like. In some cases, the identified at least one particular portion of the at least one second image corresponding to the particular region of the optical view of the first sample might include, without limitation, at least one of one or more specific cells, one or more specific tissues, one or more specific structures, or one or more molecules, and/or the like.

In some embodiments, the computing system might generate at least one highlighting field in the at least one second image covering the identified at least one particular portion of the at least one second image corresponding to the particular region of the optical view of the first sample. In some cases, the at least one highlighting field might each include, without limitation, at least one of a color, a shape, or a highlighting effect, and/or the like, where the highlighting effect might include, but is not limited to, at least one of outlining effect, shadowing effect, patterning effect, heat map effect, or jet colormap effect, and/or the like.

According to some embodiments, the at least one second image might be displayed on a display screen (e.g., display screen of display device 120, or the like). Capturing the at least one first image of the at least one eye of the user 125 might comprise capturing, with camera 130, the at least one first image of the at least one eye of the user 125, as the user 125 is looking at the image(s) or video(s) of the optical view of the first sample as displayed on the display screen of the display device 120 as the at least one second image. Alternative to camera 130, the gaze tracking device might be used to collect attention data, as the user is looking at the images or videos of the first sample that are displayed on the display screen of the display device 120. Identifying the at least one particular portion of the at least one second image corresponding to the particular region of the optical view of the first sample might comprise identifying, with the computing system, at least one particular portion of the at least one second image as displayed on the display screen corresponding to the particular region of the optical view of the first sample. The computing system might display, on the display screen (e.g., display screen of display device 120, or the like), the at least one second image with the generated at least one highlighting field covering the identified at least one particular portion of the at least one second image corresponding to the particular region of the optical view of the first sample.

In some embodiments, the display of the at least one second image on the display screen may be shifted in response to commands by the user. In some instances, shifting display of the at least one second image might comprise at least one of horizontal shifting, vertical shifting, panning, tilting, zooming in, or zooming out, and/or the like, of the at least one second image on the display screen. The camera 130 might track movement of the at least one eye of the user 125, as the user 125 is looking at the shifting display of the at least one second image on the display screen. The computing system might match the tracked movement of the at least one eye of the user 125 with the shifting display of the at least one second image on the display screen, based at least in part on one or more of the tracked movement of the at least one eye of the user 125, the identified at least one particular portion of the at least one second image corresponding to the particular region of the optical view of the first sample, or the at least one of horizontal shifting, vertical shifting, panning, tilting, zooming in on, or zooming out of the at least one second image on the display screen, and/or the like. Alternative to using camera 130, the gaze tracking device might be used to collect additional attention data, as the user is looking at the shifting display of the at least one second image on the display screen of display device 120.

Alternatively, microscope 115 might project the optical view of the first sample (e.g., sample 170 or the like) to eyepiece lens 180 through which the at least one eye of the user 125 is viewing. FOV camera 175 might capture the at least one second image of the optical view of the first sample. In some cases, capturing the at least one first image of the at least one eye of the user 125 might comprise capturing, with gaze camera 185, the at least one first image of the at least one eye of the user 125, as the user 125 is looking at the optical view of the first sample through the eyepiece lens 180. Identifying the at least one particular portion of the at least one second image corresponding to the particular region of the optical view of the first sample might comprise identifying, with the computing system, at least one particular portion of the at least one second image as viewed through the eyepiece lens 180 corresponding to the particular region of the optical view of the first sample. Generating the at least one highlighting field in the at least one second image covering the identified at least one particular portion of the at least one second image corresponding to the particular region of the optical view of the first sample might comprise generating, with the computing system, at least one highlighting field for overlapping with the identified at least one particular portion of the at least one second image as viewed through the eyepiece lens 180 corresponding to the particular region of the optical view of the first sample. The computing system might project, using projection device 190, the generated at least one highlighting field to overlap with the identified at least one particular portion of the at least one second image as viewed through the eyepiece lens 180 corresponding to the particular region of the optical view of the first sample. Alternatively, or additionally, the computing system might display, on the display screen (e.g., display screen of display device 120, or the like), the at least one second image with the generated at least one highlighting field covering the identified at least one particular portion of the at least one second image corresponding to the particular region of the optical view of the first sample.

In some instances, the FOV camera 175 might be one of an infrared ("IR") camera, a back-reflected IR camera, a visible-color camera, a light source, or a location photo-diode, and/or the like. In some cases, the microscope 115 might include, without limitation, two or more of a plurality of mirrors, a plurality of dichroic mirrors, or a plurality of half-mirrors that reflect or pass-through at least one of the optical view of the first sample as viewed through the eyepiece lens 180, an optical view of the at least one eye of the user 125 as viewed through the eyepiece lens 180 and as captured by the FOV camera 175 as the at least one first image, or projection of the generated at least one highlighting field through the eyepiece lens 180 to the at least one eye of the user 125 (if the projection device 190 is used or present), and/or the like.

According to some embodiments, projection of the optical view of the first sample to the eyepiece lens 180 may be shifted, by at least one of adjusting microscope stage 165*a* on which a microscope slide containing the first sample, exchanging objective or zoom lenses 165*f*, or adjusting focus of the eyepiece lens 180, and/or the like. The camera 130 or 185 might track movement of the at least one eye of the user 125, as the user 125 is looking at the shifting projection of the optical view of the first sample to the eyepiece lens 180. The computing system might match the tracked movement of the at least one eye of the user 125 with the shifting projection of the optical view of the first sample to the eyepiece lens 180, based at least in part on one or more of the tracked movement of the at least one eye of the user 125, the identified at least one particular portion of the at least one second image corresponding to the particular region of the optical view of the first sample, or the at least one of adjusting microscope stage 165*a* on which a microscope slide containing the first sample, exchanging objective or zoom lenses 165*f*, or adjusting focus of the eyepiece lens 180, and/or the like.

Alternatively, or additionally, the one or more audio sensors 135 might capture one or more verbal notes from the user 125, as the user 125 is looking at the optical view of the first sample. The computing system might map the captured one or more verbal notes from the user 125 with the at least one second image of the optical view of the first sample to match the captured one or more verbal notes with the at least one second image of the optical view of the first sample.

According to some embodiments, the computing system might receive outcome data provided by the user, the outcome data comprising at least one of a diagnosis of the first sample, a pathology score of the first sample, or a set of identification data corresponding to at least portions of the first sample. The computing system might train AI system 105*c* (which might generally include, without limitation, at least one of a neural network, a convolutional neural network ("CNN"), a learning algorithm-based system, or a machine learning system, and/or the like), based at least in part on at least one of analysis of the captured at least one first image of the at least one eye of the user and the captured at least one second image of the optical view of the first sample or joint analysis of the collected attention data together with the received outcome data, to generate a model that is used to generate a predicted value. In some embodiments, the predicted value might include, but is not limited to, at least one of a predicted clinical outcome or predicted attention data, and/or the like.

In an aspect, the computing system might receive at least one first image of at least one eye of a user that is captured by a first camera, as the user is looking at an optical view of a first sample through an eyepiece lens of a microscope; might receive at least one second image of the optical view of the first sample that is captured by a second camera; might analyze the at least one first image and the at least one second image to determine whether the at least one eye of the user is focused on a particular region of the optical view of the first sample; might track attention of the user based on the analysis; and might collect attention data based on the tracking.

In some aspects, a semi-weak-annotation data collection system (such as system 100, or the like) may gather information on visual attention of a pathologist during his or her routine workflow without any interference or alteration of workflow. Here, the annotation is referred to as being "weak" in the sense that it only specifies the pathologist's attention while making a decision, but not the specific decision about each location. Weakly supervised methods (where one or more scores or classifications are assigned to a microscope slide without any spatial information) have shown to provide accuracy that is comparable with state-of-the-art performance of a fully supervised methods (where all pixels are annotated in the image). By tracking the pathologist's visual attention while he or she examines and grades clinical cases, the system, according to the various embodiments, is able to collect a huge amount of valuable annotation data that would be usable, e.g., for tumor localization and classification algorithm's development.

In some embodiments, two modalities may be provided for tracing and collecting the pathologist's region of interests ("ROIs") during pathology slide scoring depending on the grading platform: (1) display device modality; and/or (2) microscope modality. With reference to the display device modality—that is, in case the pathologist scores the microscope slide while viewing a digital slide—, a weak-annotation collection system for digital-pathology may be implemented using an eye tracking system (or gaze-tracking camera, or the like) that would track the pathologist's gaze while looking at a whole slide image ("WSI") on the screen. In addition, the coordinates (and in some cases, size and magnification) of the field of views ("FOVs") and duration where the user zooms into will be stored. The gaze tracking system might integrate the information from both the gaze-tracking camera (annotated by jet colormap, or the like) and the WSI FOVs (displayed as an RGB image, or the like) (such as depicted in FIG. 2B, or the like).

Figure 3A:
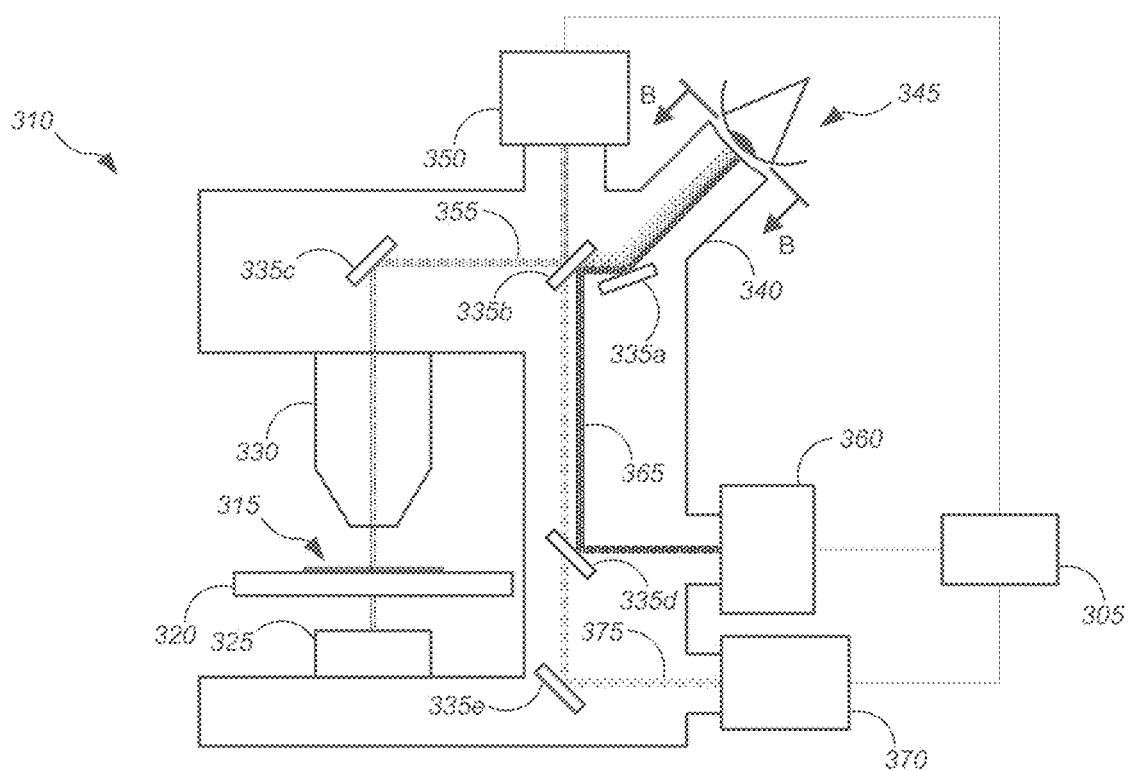
FIGS. 3A-3D are schematic diagrams illustrating various other non-limiting examples of annotation data collection using gaze-based tracking, in accordance with various embodiments.
Figure 3B:
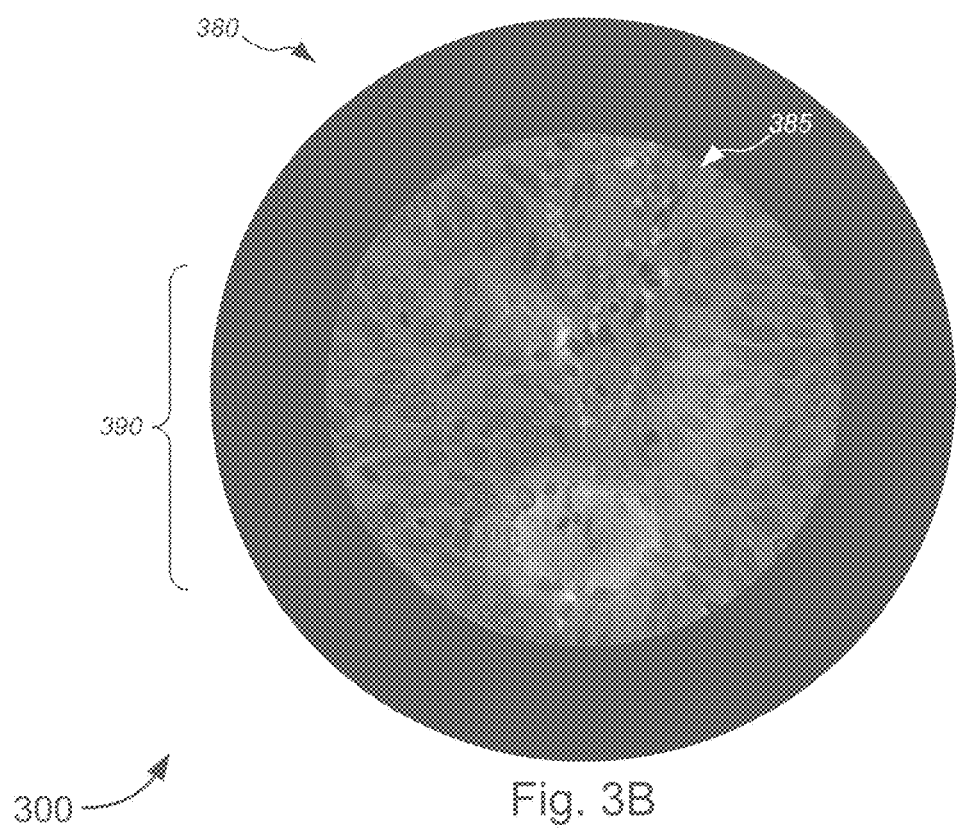
Figure 3C:
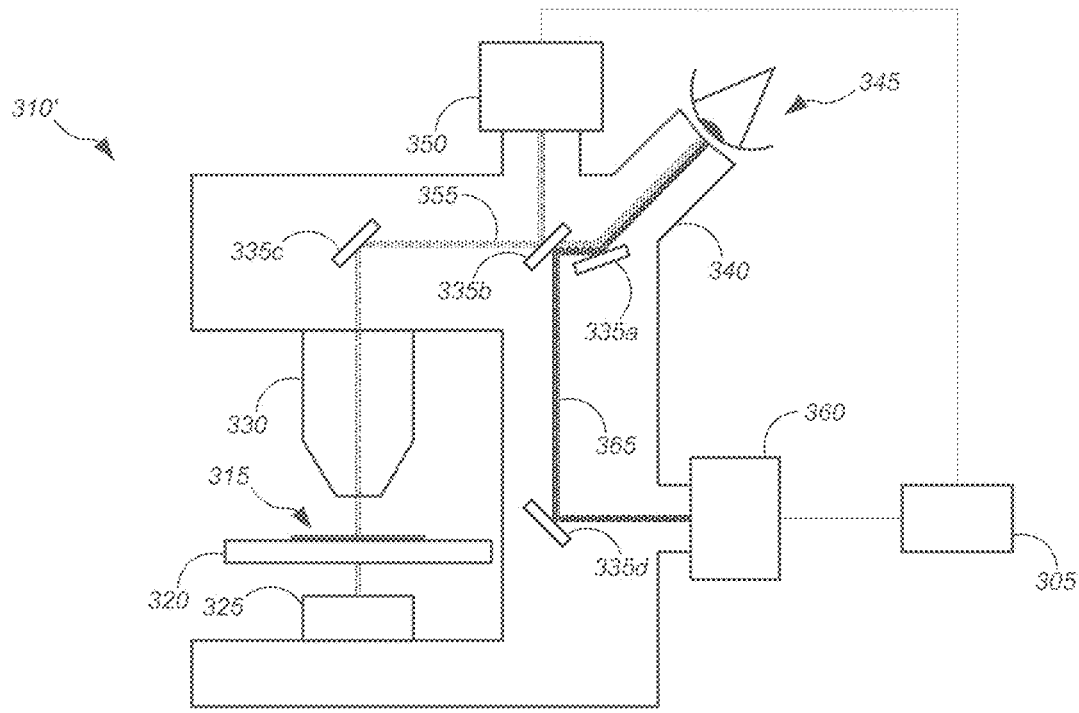

Referring to the microscope modality—that is, in the case the pathologist scores the slide with a microscope—, the weak-annotation collection system for digital-pathology may be implemented using a custom eye tracking system integrated within a microscope, which is implemented without interfering with the pathologist's continued workflow (e.g., as depicted in FIG. 3A or 3C, or the like). The gaze system may be based on optical tracking of the pathologist's eye motions through detection of back-reflected infrared ("IR") light source, or the like, from the pathologist's eyes by digital cameras while the pathologist is continuously viewing the sample through the microscope eye pieces (or eyepiece lens). In addition, another digital camera may be used to capture the field of view ("FOV") that the user is currently viewing on the pathology slide. A gaze tracking software, integrating the information from both gaze cameras and the FOV camera, will overlay user-observed ROIs over matched FOVs during the grading process. Finally, the recorded FOVs will be registered to WSI that would be scanned post grading process, providing localization of the pathologist grading on WSI through gaze-based interaction.

In some embodiments, voice recording/recognition capabilities may be included to make the "weak" annotation even stronger.

These and other functions of the system 100 (and its components) are described in greater detail below with respect to FIGS. 2-5. Further, although the various embodiments are described herein with respect to microscopy-related applications, the various embodiments are not so limited, and may be applicable to other fields or technologies where "weak" annotations can be used—including, but not limited to, locating faults in manufacturing processes, locating faults in a malfunctioning machine or system, tracking gaze while an operator is solving or performing a pre-defined task, and/or the like.

Figure 2A:
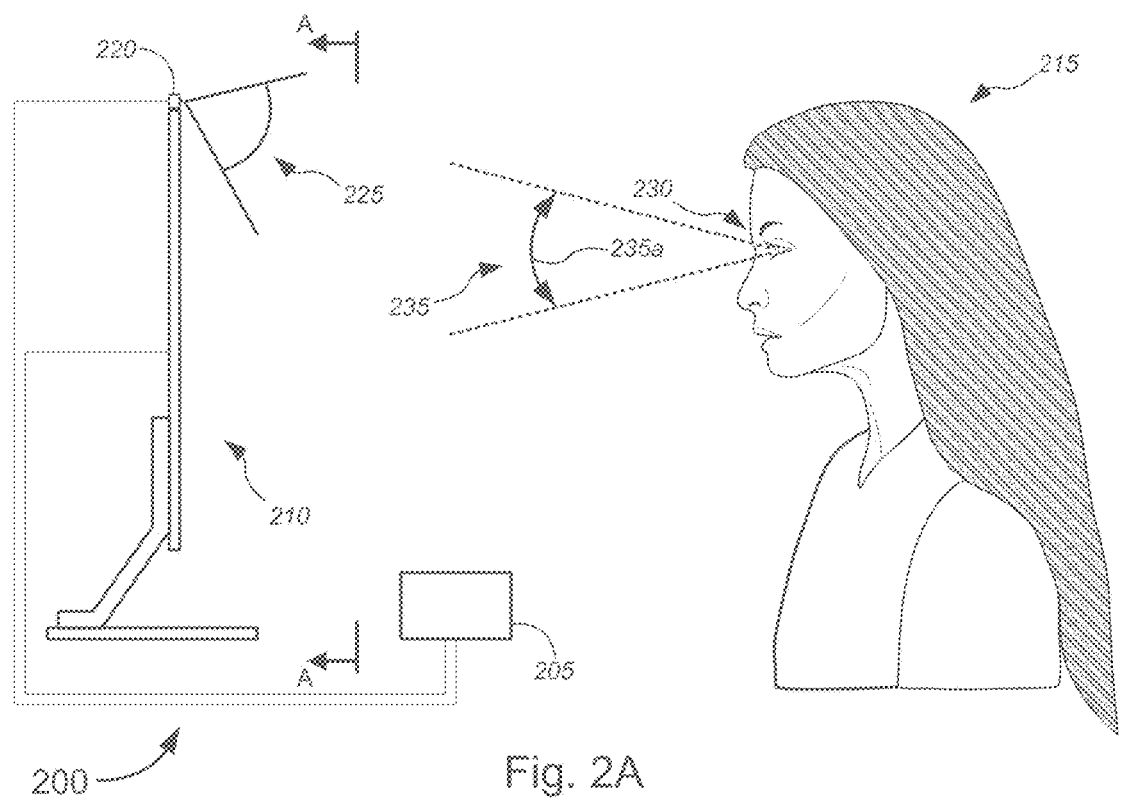
FIGS. 2A and 2B are schematic diagrams illustrating a non-limiting example of annotation data collection using gaze-based tracking, in accordance with various embodiments.
Figure 2B:
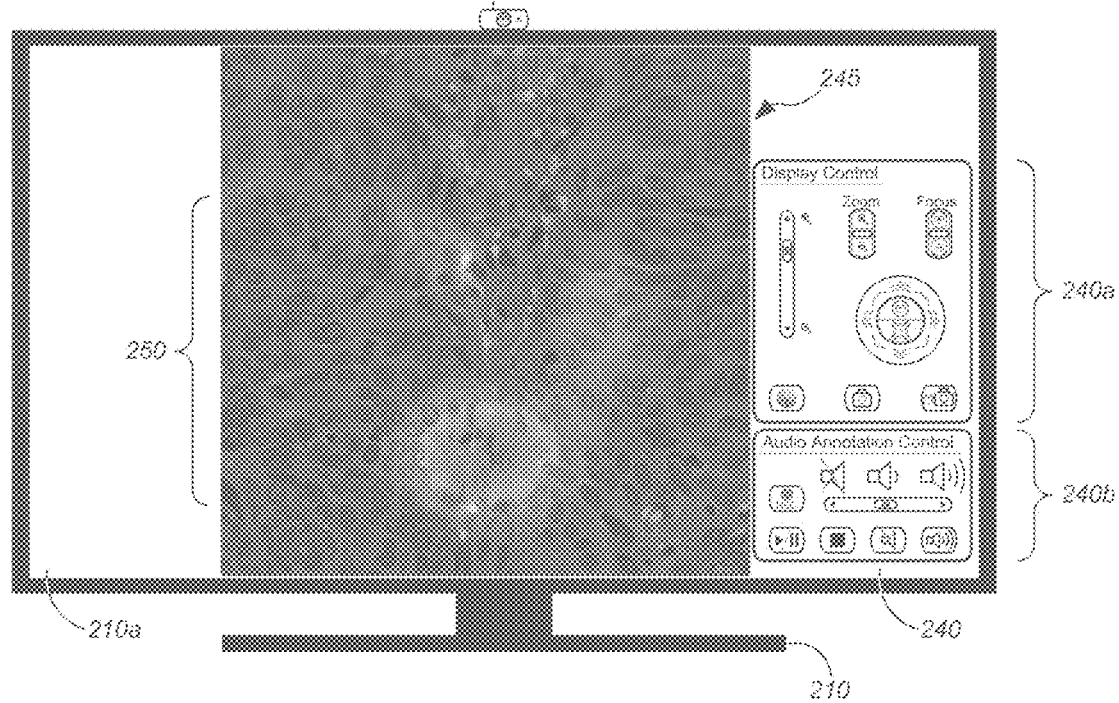

FIGS. 2A and 2B (collectively, "FIG. 2") are schematic diagrams illustrating a non-limiting example 200 of annotation data collection using gaze-based tracking, in accordance with various embodiments. FIG. 2A depicts a side view of a user viewing at an image of a sample being displayed on a display screen while the user's eye(s) is(are) being tracked and image-captured, while FIG. 2B depicts the image of the sample being displayed on the display screen, as shown in the A-A direction of FIG. 2A.

With reference to the non-limiting example 200 of FIG. 2A, a computing system 205 (similar to computing system 105a, remote computing system 105b, and/or user device(s) 140 of FIG. 1, or the like) might display images or videos of a first sample on a display screen of a display device 210 (similar to display device 120 of FIG. 1, or the like). In some cases, the first sample might include, without limitation, at least one of one or more specific cells, one or more specific tissues, one or more specific structures, or one or more molecules, and/or the like. In some instances, the first sample, the images or videos of which are displayed on the display screen of the display device 210, might be contained within at least one of a microscope slide, a transparent sample cartridge, a vial, a tube, a capsule, a flask, a vessel, a receptacle, a microarray, or a microfluidic chip, and/or the like. A user 215 (similar to user 125 of FIG. 1, or the like) might view the images or videos of the first sample as displayed on the display screen of the display device 210, as a camera or gaze camera 220 (similar to camera 130 of FIG. 1, or the like) captures images or videos of the user 215 or at least one eye 230 of the user 215. In some cases, the camera 220 might have a field of view ("FOV") 225, while the at least one eye 230 might have a field of view 235 defining an angle 235a that is rotated about a 360 degree direction about an axis that is normal to the lens of the user's eye(s) 230. Alternative to camera 220, a gaze tracking device might be used to collect attention data, as the user is looking at the images or videos of the first sample that are displayed on the display screen of the display device 210.

Turning to FIG. 2B, as viewed in the A-A direction in FIG. 2A, on display screen 210a of display device 210 might be displayed an annotation data collection user interface ("UI") 240, which might display an image(s) or video(s) of the first sample 245, and which might provide user interface inputs or icons (including, but not limited to, display control inputs or icons 240a, audio annotation control inputs or icons 240b, and/or the like). In some cases, the display control inputs or icons 240a might include, without limitation, at least one of zoom in, zoom out, zoom scroll bar, focus in, focus out, direction shifting controls (e.g., upward shift, downward shift, rightward shift, leftward shift, upward-right shift, upward-left shift, downward-right shift, downward-left shift, etc.), autofocus, center or center-focus out, colormap or highlighting effects options, single screen-shot, or multiple screenshot, and/or the like. In some instances, the audio annotation control inputs or icons 240b might include, but is not limited to, at least one of record, play or pause, stop, mute, audio on, or audio scroll bar, and/or the like. Also shown in FIG. 2B is camera 220 of FIG. 2A.

In operation, camera 220 might capture at least one first image of at least one eye 230 of the user 215, as the user 215 is looking at an optical view of a first sample 245, as displayed on the display screen 210a of display device 210, or the like. Computing system 205 might analyze the captured at least one first image of the at least one eye 230 of the user 215 and at least one second image of the optical view of the first sample 245 to determine whether the at least one eye 230 of the user 215 is focused on a particular region of the optical view of the first sample 245, as displayed on the display screen 210a of display device 210. Alternative to camera 220, the gaze tracking device might be used to collect attention data, as the user is looking at the images or videos of the first sample that are displayed on the display screen of the display device 210. Based on a determination that the at least one eye 230 of the user 215 is focused on a particular region of the optical view of the first sample 245 as displayed on the display screen 210a of display device 210 or based on the collected attention data, the computing system 205 might identify at least one particular portion of the at least one second image, as displayed on the display screen 210a of display device 210, corresponding to the particular region of the optical view of the first sample 245. The computing system 205 might generate at least one highlighting field 250 in the at least one second image covering the identified at least one particular portion of the at least one second image corresponding to the particular region of the optical view of the first sample 245. The computing system 205 might display, on the display screen 210a of display device 210, the at least one second image with the generated at least one highlighting field 250 covering the identified at least one particular portion of the at least one second image corresponding to the particular region of the optical view of the first sample 245.

In some embodiments, the at least one highlighting field 250 might each include, without limitation, at least one of a color, a shape, or a highlighting effect, and/or the like, where the highlighting effect might include, but is not limited to, at least one of outlining effect, shadowing effect, patterning effect, heat map effect, or jet colormap effect, and/or the like. In some cases, the identified at least one particular portion of the at least one second image corresponding to the particular region of the optical view of the first sample 245 might include, without limitation, at least one of one or more specific cells, one or more specific tissues, one or more specific structures, or one or more molecules, and/or the like.

In some embodiments, the display of the at least one second image on the display screen 210a of display device 210 may be shifted in response to commands by the user 215 (whether verbal commands, key-stroke commands, user interface commands, or the like). In some instances, shifting display of the at least one second image might include, without limitation, at least one of horizontal shifting, vertical shifting, panning, tilting, zooming in, or zooming out, and/or the like, of the at least one second image on the display screen 210a of display device 210. The camera 220 might track movement of the at least one eye 230 of the user 215, as the user 215 is looking at the shifting display of the at least one second image on the display screen 210a of display device 210. The computing system 205 might match the tracked movement of the at least one eye 230 of the user 215 with the shifting display of the at least one second image on the display screen 210a of display device 210, based at least in part on one or more of the tracked movement of the at least one eye 230 of the user 215, the identified at least one particular portion of the at least one second image corresponding to the particular region of the optical view of the first sample, or the at least one of horizontal shifting, vertical shifting, panning, tilting, zooming in on, or zooming out of the at least one second image on the display screen, and/or the like. Alternative to using camera 220, the gaze tracking device might be used to collect additional attention data, as the user is looking at the shifting display of the at least one second image on the display screen 210a of display device 210.

Figure 3D:
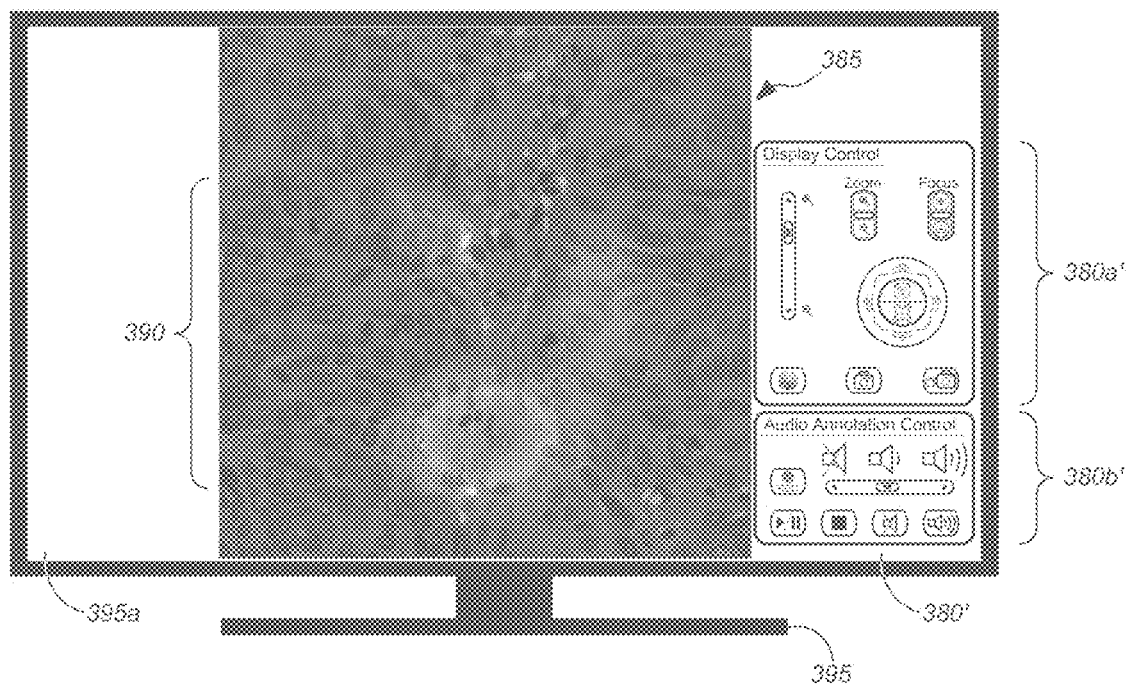

FIGS. 3A-3D (collectively, "FIG. 3") are schematic diagrams illustrating various other non-limiting examples 300 and 300' of annotation data collection using gaze-based tracking, in accordance with various embodiments. FIG. 3A depicts a side view of a microscope whose eyepiece lens is one through which a user is viewing an image of a sample, while FIG. 3B depicts the image of the sample being projected through the eyepiece lens, as shown in the B-B direction of FIG. 3A. FIG. 3C depicts example 300', which is an alternative to example 300 as shown in FIG. 3A, while FIG. 3D depicts a display screen on which an annotated image(s) or video(s) of the sample is displayed.

With reference to the non-limiting example 300 of FIG. 3A, a computing system 305 (similar to computing system 105a, remote computing system 105b, user device(s) 140, and/or processor 155 of FIG. 1, or the like), which either might be integrated within microscope 310 (not shown) or might be external, yet communicatively coupled, to microscope 310 (shown in FIG. 3A), might control various operations of microscope 310. As shown in FIG. 3A, a microscope slide 315 containing a first sample might be positioned on an adjustable microscope stage 320 (e.g., X-Y stage or X-Y-Z stage, or the like, similar to microscope stage 165a of FIG. 1, or the like), with light from a light source 325 (similar to light source 165e of FIG. 1, or the like) being projected through stage 320, through microscope slide 315, through one of at least one objective or zoom lens 330 (similar to objective or zoom lens(es) 165f of FIG. 1, or the like), and reflected off or through a plurality of mirrors, dichroic mirrors, and/or half-mirrors 335, through eyepiece lens 340 (similar to eyepiece lens 180 of FIG. 1, or the like) to at least one eye 345 of a user.

The microscope 310 might comprise a field of view ("FOV") camera 350 (similar to FOV camera 175 of FIG. 1, or the like) that may be used to capture an image(s) or a video(s) of the first sample contained in microscope slide 315 along light beam 355 (depicted in FIG. 3A as a medium shaded thick line 355, or the like). Light beam 355 might extend from light source 325, through stage 320, through the first sample contained in microscope slide 315, through the one of at least one objective or zoom lens 330, reflected off mirrors, dichroic mirrors, and/or half-mirrors 335b and 335c, to FOV camera 350. In other words, the FOV camera 350 might capture the image(s) or the video(s) of the first sample contained in microscope slide 315 (along light beam 355), as backlit by light source 325. The eyepiece lens 340 might collect light of the projected image(s) or video(s) of the first sample contained in microscope slide 315, as projected by light source 325. Light beam 355 might extend from light source 325, through stage 320, through the first sample contained in microscope slide 315, through the one of at least one objective or zoom lens 330, reflected off mirror 335c, through half-mirror 335b, reflected off mirror 335a, through eyepiece lens 340, to the at least one eye 345 of the user. In other words, the user might view the image(s) or video(s) of the first sample contained in microscope slide 315 (along light beam 355), as backlit by light source 325.

The microscope 310 might further comprise a gaze camera 360 (similar to gaze camera 185 of FIG. 1, or the like) that may be used to capture an image(s) or a video(s) of the at least one eye 345 of the user along light beam 365 (depicted in FIG. 3A as a heavily shaded thick line 365, or the like). Light beam 365 might extend from the at least one eye 345 of the user, through eyepiece lens 340, reflected off mirrors, dichroic mirrors, and/or half-mirrors 335a, 335b, and 335d, to gaze camera 360. According to some embodiments, the gaze camera 360 might include, but is not limited to, one of an infrared ("IR") camera, a back-reflected IR camera, a visible-color camera, a light source, or a location photodiode, and/or the like.

In operation, the microscope 310 might project an optical view of a first sample to eyepiece lens 340 through which at least one eye 345 of a user is viewing. The gaze camera 360 might capture at least one first image of the at least one eye 345 of the user, as the user is looking at the optical view of the first sample as viewed through the eyepiece lens 340 of the microscope 310. FOV camera 350 might capture at least one second image of the optical view of the first sample. Computing system 305 might analyze the captured at least one first image of the at least one eye 345 of the user and the captured at least one second image of the optical view of the first sample to determine whether the at least one eye 345 of the user is focused on a particular region of the optical view of the first sample. Based on a determination that the at least one eye 345 of the user is focused on a particular region of the optical view of the first sample, the computing system 305 might identify at least one particular portion of the at least one second image corresponding to the particular region of the optical view of the first sample. The computing system 305 might collect attention data comprising the identified at least one particular portion of the at least one second image, and might store the collected attention data in a database (e.g., database(s) 110a or 110b of FIG. 1, or the like). According to some embodiments, collecting the attention data might be performed without interrupting, slowing, or encumbering the user as the user is providing the outcome data while diagnosing the first sample using the microscope. In some instances, the collected attention data might include, but is not limited to, at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample, and/or the like. In some cases, the identified at least one particular portion of the at least one second image corresponding to the particular region of the optical view of the first sample might include, without limitation, at least one of one or more specific cells, one or more specific tissues, one or more specific structures, or one or more molecules, and/or the like.

In some embodiments, the computing system 305 might generate at least one highlighting field in the at least one second image for overlapping with the identified at least one particular portion of the at least one second image corresponding to the particular region of the optical view of the first sample. In some cases, the at least one highlighting field might each include, without limitation, at least one of a color, a shape, or a highlighting effect, and/or the like, where the highlighting effect might include, but is not limited to, at least one of outlining effect, shadowing effect, patterning effect, heat map effect, or jet colormap effect, and/or the like.

According to some embodiments, the microscope 310 might further comprise a projection device 370 (similar to projection device 190 of FIG. 1, or the like) that may be used to project the generated at least one highlighting field through the eyepiece lens 340 to the at least one eye 345 of the user along light beam 375 (depicted in FIG. 3A as a lightly shaded thick line 375, or the like). Light beam 375 might extend from projection device 370, reflected off mirror 335*e*, through half-mirror 335*d*, reflected off half-mirror 335*b*, reflected off mirror 335*a*, through eyepiece lens 340, to the at least one eye 345 of the user.

FIG. 3B depicts the optical view 380 of the first sample as viewed through the eyepiece lens 340 of the microscope 310 along the B-B direction of FIG. 3A. The optical view 380 includes the at least one second image of the first sample 385. As shown in FIG. 3B, the optical view 380 might, in some embodiments, further include one or more generated highlighting fields 390 (in this case, depicted or embodied by a jet colormap, or the like) that highlight portions of the first sample 385 that the user's eye(s) is(are) focused on. For example, with reference to the jet colormap embodiment, red-colored regions of the colormap might represent the highest incidence or duration of eye focus or attention, while yellow or orange-colored regions of the colormap might represent the next highest incidence or duration of eye focus or attention, and green-colored regions of the colormap might represent a lower incidence or duration of eye focus or attention, while blue or purple-colored regions of the colormap might represent the lowest incidence or duration of eye focus or attention that are statistically greater than that of roving or scanning focus or attention, or the like.

Referring to FIG. 3C, alternative to microscope 310 of the non-limiting example 300 of FIG. 3A, microscope 310' of non-limiting example 300' of FIG. 3C might exclude the projection device 370 and mirror 335*e*, but would otherwise be similar to microscope 310 of FIG. 3A.

In particular, a computing system 305 (similar to computing system 105*a*, remote computing system 105*b*, user device(s) 140, and/or processor 155 of FIG. 1, or the like), which either might be integrated within microscope 310' (not shown) or might be external, yet communicatively coupled, to microscope 310' (shown in FIG. 3C), might control various operations of microscope 310'. As shown in FIG. 3C, a microscope slide 315 containing a first sample might be positioned on an adjustable microscope stage 320 (e.g., X-Y stage or X-Y-Z stage, or the like, similar to microscope stage 165*a* of FIG. 1, or the like), with light from a light source 325 (similar to light source 165*e* of FIG. 1, or the like) being projected through stage 320, through microscope slide 315, through one of at least one objective or zoom lens 330 (similar to objective or zoom lens(es) 165*f* of FIG. 1, or the like), and reflected off or through a plurality of mirrors, dichroic mirrors, and/or half-mirrors 335, through eyepiece lens 340 (similar to eyepiece lens 180 of FIG. 1, or the like) to at least one eye 345 of a user.

The microscope 310' might comprise a FOV camera 350 (similar to FOV camera 175 of FIG. 1, or the like) that may be used to capture an image(s) or a video(s) of the first sample contained in microscope slide 315 along light beam 355 (depicted in FIG. 3C as a medium shaded thick line 355, or the like). Light beam 355 might extend from light source 325, through stage 320, through the first sample contained in microscope slide 315, through the one of at least one objective or zoom lens 330, reflected off mirrors, dichroic mirrors, and/or half-mirrors 335*b* and 335*c*, to FOV camera 350. In other words, the FOV camera 350 might capture the image(s) or the video(s) of the first sample contained in microscope slide 315 (along light beam 355), as backlit by light source 325. The eyepiece lens 340 might collect light of the projected image(s) or video(s) of the first sample contained in microscope slide 315, as projected by light source 325. Light beam 355 might extend from light source 325, through stage 320, through the first sample contained in microscope slide 315, through the one of at least one objective or zoom lens 330, reflected off mirror 335*c*, through half-mirror 335*b*, reflected off mirror 335*a*, through eyepiece lens 340, to the at least one eye 345 of the user. In other words, the user might view the image(s) or video(s) of the first sample contained in microscope slide 315 (along light beam 355), as backlit by light source 325.

The microscope 310' might further comprise a gaze camera 360 (similar to gaze camera 185 of FIG. 1, or the like) that may be used to capture an image(s) or a video(s) of the at least one eye 345 of the user along light beam 365 (depicted in FIG. 3C as a heavily shaded thick line 365, or the like). Light beam 365 might extend from the at least one eye 345 of the user, through eyepiece lens 340, reflected off mirrors, dichroic mirrors, and/or half-mirrors 335*a*, 335*b*, and 335*d*, to gaze camera 360. According to some embodiments, the gaze camera 360 might include, but is not limited to, one of an infrared ("IR") camera, a back-reflected IR camera, a visible-color camera, a light source, or a location photodiode, and/or the like.

In operation, similar to example 300 of FIG. 3A, the microscope 310 might project an optical view of a first sample to eyepiece lens 340 through which at least one eye 345 of a user is viewing. The gaze camera 360 might capture at least one first image of the at least one eye 345 of the user, as the user is looking at the optical view of the first sample as viewed through the eyepiece lens 340 of the microscope 310'. FOV camera 350 might capture at least one second image of the optical view of the first sample. Computing system 305 might analyze the captured at least one first image of the at least one eye 345 of the user and the captured at least one second image of the optical view of the first sample to determine whether the at least one eye 345 of the user is focused on a particular region of the optical view of the first sample. Based on a determination that the at least one eye 345 of the user is focused on a particular region of the optical view of the first sample, the computing system 305 might identify at least one particular portion of the at least one second image corresponding to the particular region of the optical view of the first sample. The computing system 305 might collect attention data comprising the identified at least one particular portion of the at least one second image, and might store the collected attention data in a database (e.g., database(s) 110*a* or 110*b* of FIG. 1, or the like). According to some embodiments, collecting the attention data might be performed without interrupting, slowing, or encumbering the user as the user is providing the outcome data while diagnosing the first sample using the microscope. In some instances, the collected attention data might include, but is not limited to, at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample, and/or the like. In some cases, the identified at least one particular portion of the at least one second image corresponding to the particular region of the optical view of the first sample might include, without limitation, at least one of one or more specific cells, one or more specific tissues, one or more specific structures, or one or more molecules, and/or the like.

In some embodiments, the computing system 305 might generate at least one highlighting field in the at least one second image for overlapping with the identified at least one particular portion of the at least one second image corresponding to the particular region of the optical view of the first sample. In some cases, the at least one highlighting field might each include, without limitation, at least one of a color, a shape, or a highlighting effect, and/or the like, where the highlighting effect might include, but is not limited to, at least one of outlining effect, shadowing effect, patterning effect, heat map effect, or jet colormap effect, and/or the like.

Unlike example 300 of FIG. 3A, where the generated at least one highlighting field is projected through the eyepiece lens 340 to the at least one eye 345 of the user via mirrors, dichroic mirrors, and/or half-mirrors 335, computing system 305 of example 300' of FIG. 3C might display, on a display screen 395a of display device 395, the image(s) or video(s) of the first sample 385 (as shown in FIG. 3D). Similar to example 300 of FIG. 3B, the optical view of example 300' of FIG. 3D might further include one or more generated highlighting fields 390 (in this case, depicted or embodied by a jet colormap, or the like) that highlight portions of the first sample 385 that the user's eye(s) is(are) focused on. For example, with reference to the jet colormap embodiment, red-colored regions of the colormap might represent the highest incidence or duration of eye focus or attention, while yellow or orange-colored regions of the colormap might represent the next highest incidence or duration of eye focus or attention, and green-colored regions of the colormap might represent a lower incidence or duration of eye focus or attention, while blue or purple-colored regions of the colormap might represent the lowest incidence or duration of eye focus or attention that are statistically greater than that of roving or scanning focus or attention, or the like.

Similar to display of the image(s) or video(s) of the first sample 245 on display screen 210a of display device 210 of FIG. 2B, the image(s) or video(s) of the first sample 385 may be displayed within an annotation data collection user interface ("UI") 380' that is displayed on display screen 395a of display device 395. Similar to the example of FIG. 2B, the annotation data collection UI 380' of FIG. 3D might provide user interface inputs or icons (including, but not limited to, display control inputs or icons 380a', audio annotation control inputs or icons 380b', and/or the like). In some cases, the display control inputs or icons 380a' might include, without limitation, at least one of zoom in, zoom out, zoom scroll bar, focus in, focus out, direction shifting controls (e.g., upward shift, downward shift, rightward shift, leftward shift, upward-right shift, upward-left shift, downward-right shift, downward-left shift, etc.), autofocus, center or center-focus out, colormap or highlighting effects options, single screenshot, or multiple screenshot, and/or the like. In some instances, the audio annotation control inputs or icons 380b' might include, but is not limited to, at least one of record, play or pause, stop, mute, audio on, or audio scroll bar, and/or the like.

In some embodiments, the display of the image(s) or video(s) of the first sample 385 on display screen 395a of display device 395 of FIG. 3D may be in addition to the optical view 380 of the first sample 385 as viewed through the eyepiece lens 340 of the microscope 310 of FIG. 3B.

FIGS. 4A-4D (collectively, "FIG. 4") are flow diagrams illustrating a method 400 for implementing annotation data collection using gaze-based tracking, in accordance with various embodiments. Method 400 of FIG. 4A continues onto FIG. 4B following the circular marker denoted, "A," and continues from FIG. 4A onto FIG. 4C following the circular marker denoted, "B." Method 400 of FIG. 4B continues onto FIG. 4C following the circular marker denoted, "C."

While the techniques and procedures are depicted and/or described in a certain order for purposes of illustration, it should be appreciated that certain procedures may be reordered and/or omitted within the scope of various embodiments. Moreover, while the method 400 illustrated by FIG. 4 can be implemented by or with (and, in some cases, are described below with respect to) the systems, examples, or embodiments 100, 200, and 300 of FIGS. 1, 2, and 3, respectively (or components thereof), such methods may also be implemented using any suitable hardware (or software) implementation. Similarly, while each of the systems, examples, or embodiments 100, 200, and 300 of FIGS. 1, 2, and 3, respectively (or components thereof), can operate according to the method 400 illustrated by FIG. 4 (e.g., by executing instructions embodied on a computer readable medium), the systems, examples, or embodiments 100, 200, and 300 of FIGS. 1, 2, and 3 can each also operate according to other modes of operation and/or perform other suitable procedures.

Figure 4A:
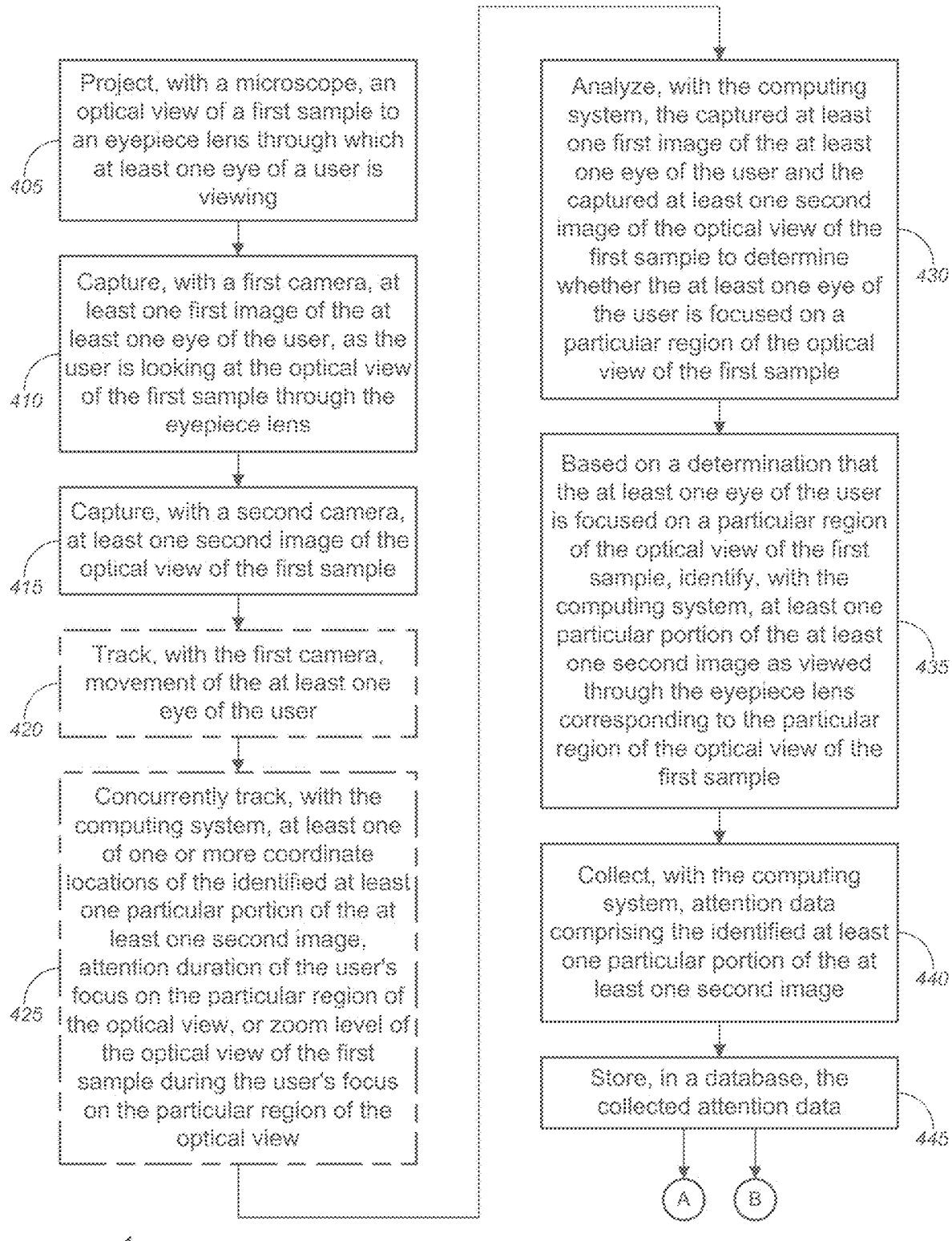

In the non-limiting embodiment of FIG. 4A, method 400, at block 405, might comprise projecting, with a microscope, an optical view of a first sample to an eyepiece lens through which at least one eye of a user is viewing. In some embodiments, the first sample might be contained within at least one of a microscope slide, a transparent sample cartridge, a vial, a tube, a capsule, a flask, a vessel, a receptacle, a microarray, or a microfluidic chip, and/or the like. According to some embodiments, the microscope might include, without limitation, two or more of a plurality of mirrors, a plurality of dichroic mirrors, or a plurality of half-mirrors, and/or the like, that reflect or pass-through at least one of the optical view of the first sample as viewed through the eyepiece lens or an optical view of the at least one eye of the user as viewed through the eyepiece lens and as captured by the first camera as the at least one first image.

Method 400 might further comprise capturing, with a first camera, at least one first image of the at least one eye of the user, as the user is looking at the optical view of the first sample through the eyepiece lens (block 410); and capturing, with a second camera, at least one second image of the optical view of the first sample (block 415).

At optional block 420, method 400 might comprise tracking, with the first camera, movement of the at least one eye of the user. Method 400 might further comprise, at optional block 425, concurrently tracking, with the computing system, at least one of one or more coordinate locations of the identified at least one particular portion of the at least one second image, attention duration of the user's focus on the particular region of the optical view, or zoom level of the optical view of the first sample during the user's focus on the particular region of the optical view, and/or the like. In some cases, the first camera might include, but is not limited to, one of an infrared ("IR") camera, a back-reflected IR camera, a visible-color camera, a light source, or a location photodiode, and/or the like.

Method 400 might further comprise analyzing, with a computing system, the captured at least one first image of the at least one eye of the user and the captured at least one second image of the optical view of the first sample to determine whether the at least one eye of the user is focused on a particular region of the optical view of the first sample (block 430); and based on a determination that the at least one eye of the user is focused on a particular region of the optical view of the first sample, identifying, with the computing system, at least one particular portion of the at least one second image as viewed through the eyepiece lens corresponding to the particular region of the optical view of the first sample (block 435). According to some embodiments, the identified at least one particular portion of the at least one second image corresponding to the particular region of the optical view of the first sample might include, without limitation, at least one of one or more specific cells, one or more specific tissues, one or more specific structures, or one or more molecules, and/or the like. In some embodiments, identifying the at least one particular portion of the at least one second image might comprise determining, with the computing system, coordinate locations within the at least one second image of the optical view corresponding to the identified at least one particular portion of the at least one second image.

Method 400, at block 440, might comprise collecting, with the computing system, attention data comprising the identified at least one particular portion of the at least one second image. At block 445, method 400 might comprise storing, in a database, the collected attention data. Method 400 might continue onto the process at optional block 450 in FIG. 4B following the circular marker denoted, "A," or might continue onto the process at block 460 in FIG. 4C following the circular marker denoted, "B."

At optional block 450 in FIG. 4B (following the circular marker denoted, "A"), method 400 might comprise capturing, with an audio sensor, one or more verbal notes from the user, as the user is looking at the optical view of the first sample. Method 400 might further comprise mapping, with the computing system, the captured one or more verbal notes from the user with the at least one second image of the optical view of the first sample to match the captured one or more verbal notes with the at least one second image of the optical view of the first sample (optional block 455). Method 400 might continue onto the process at block 465 in FIG. 4C following the circular marker denoted, "C."

Alternatively, or additionally, at block 460 in FIG. 4C (following the circular marker denoted, "B"), method 400 might comprise receiving, with the computing system, outcome data provided by the user, the outcome data comprising at least one of a diagnosis of the first sample, a pathology score of the first sample, or a set of identification data corresponding to at least portions of the first sample. Method 400 might further comprise, at block 465, training at least one of a neural network, a convolutional neural network ("CNN"), an artificial intelligence ("AI") system, or a machine learning system, based at least in part on at least one of analysis of the captured at least one first image of the at least one eye of the user and the captured at least one second image (and, in some cases, captured verbal notes mapped to the captured at least one second image) of the optical view of the first sample or joint analysis of the collected attention data together with the received outcome data, to generate a model that is used to generate a predicted value. In some embodiments, the predicted value might include, without limitation, at least one of a predicted clinical outcome or predicted attention data, and/or the like. According to some embodiments, collecting the attention data might be performed without interrupting, slowing, or encumbering the user as the user is providing the outcome data while diagnosing the first sample using the microscope.

Figure 4D:
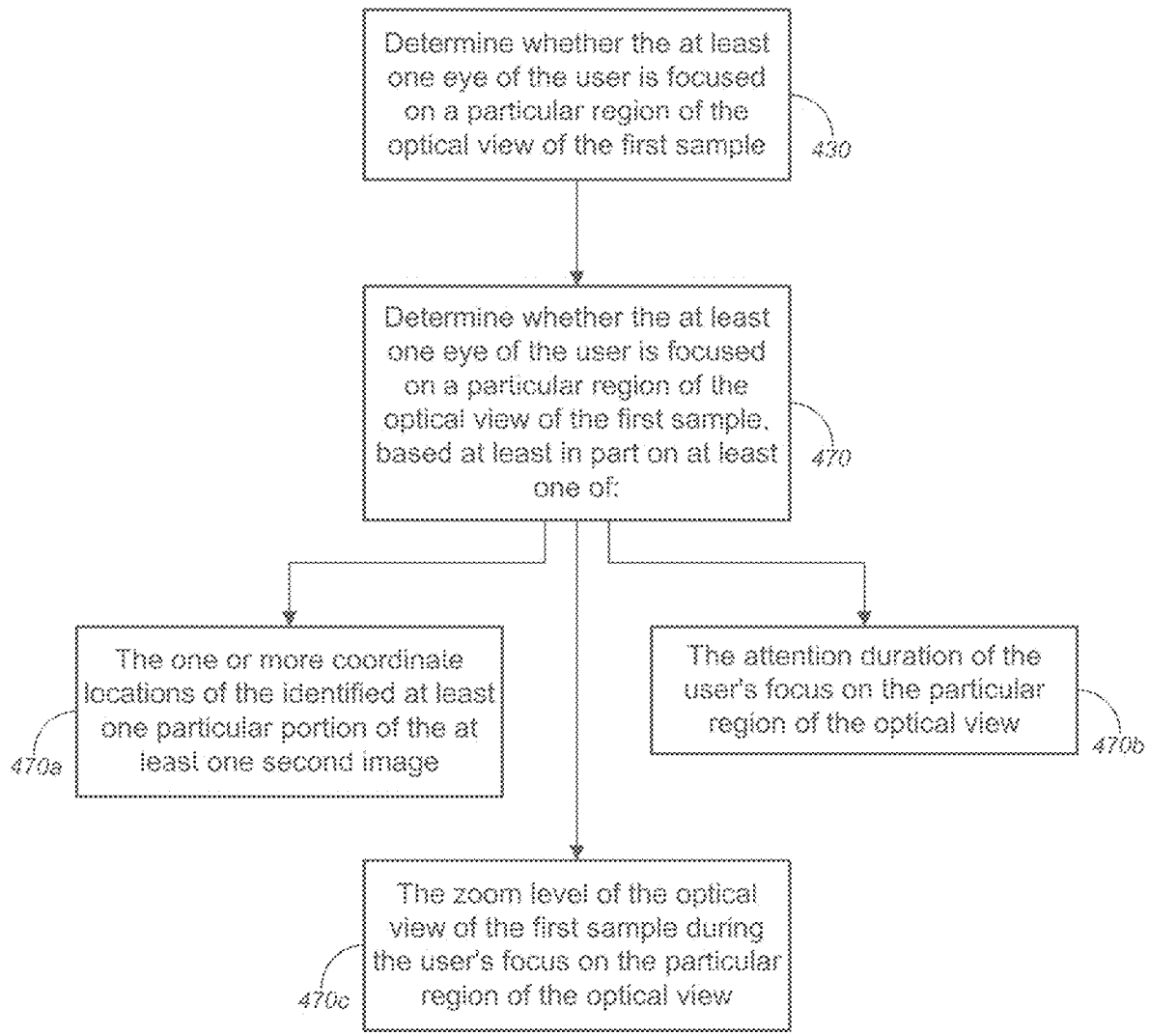

Turning to FIG. 4D, determining whether the at least one eye of the user is focused on a particular region of the optical view of the first sample (at block 430) might comprise, at block 470, determining whether the at least one eye of the user is focused on a particular region of the optical view of the first sample, based at least in part on at least one of: the one or more coordinate locations of the identified at least one particular portion of the at least one second image (at block 470a); the attention duration of the user's focus on the particular region of the optical view (at block 470b); or the zoom level of the optical view of the first sample during the user's focus on the particular region of the optical view (at block 470c).

FIGS. 5A-5D (collectively, "FIG. 5") are flow diagrams illustrating a method 500 for implementing annotation data collection using gaze-based tracking, in accordance with various embodiments. Method 500 of FIG. 5B continues onto FIG. 5C or FIG. 5D following the circular marker denoted, "A," and returns from FIG. 5C or FIG. 5D to FIG. 5A following the circular marker denoted, "B."

While the techniques and procedures are depicted and/or described in a certain order for purposes of illustration, it should be appreciated that certain procedures may be reordered and/or omitted within the scope of various embodiments. Moreover, while the method 500 illustrated by FIG. 5 can be implemented by or with (and, in some cases, are described below with respect to) the systems, examples, or embodiments 100, 200, and 300 of FIGS. 1, 2, and 3, respectively (or components thereof), such methods may also be implemented using any suitable hardware (or software) implementation. Similarly, while each of the systems, examples, or embodiments 100, 200, and 300 of FIGS. 1, 2, and 3, respectively (or components thereof), can operate according to the method 500 illustrated by FIG. 5 (e.g., by executing instructions embodied on a computer readable medium), the systems, examples, or embodiments 100, 200, and 300 of FIGS. 1, 2, and 3 can each also operate according to other modes of operation and/or perform other suitable procedures.

Figure 5A:
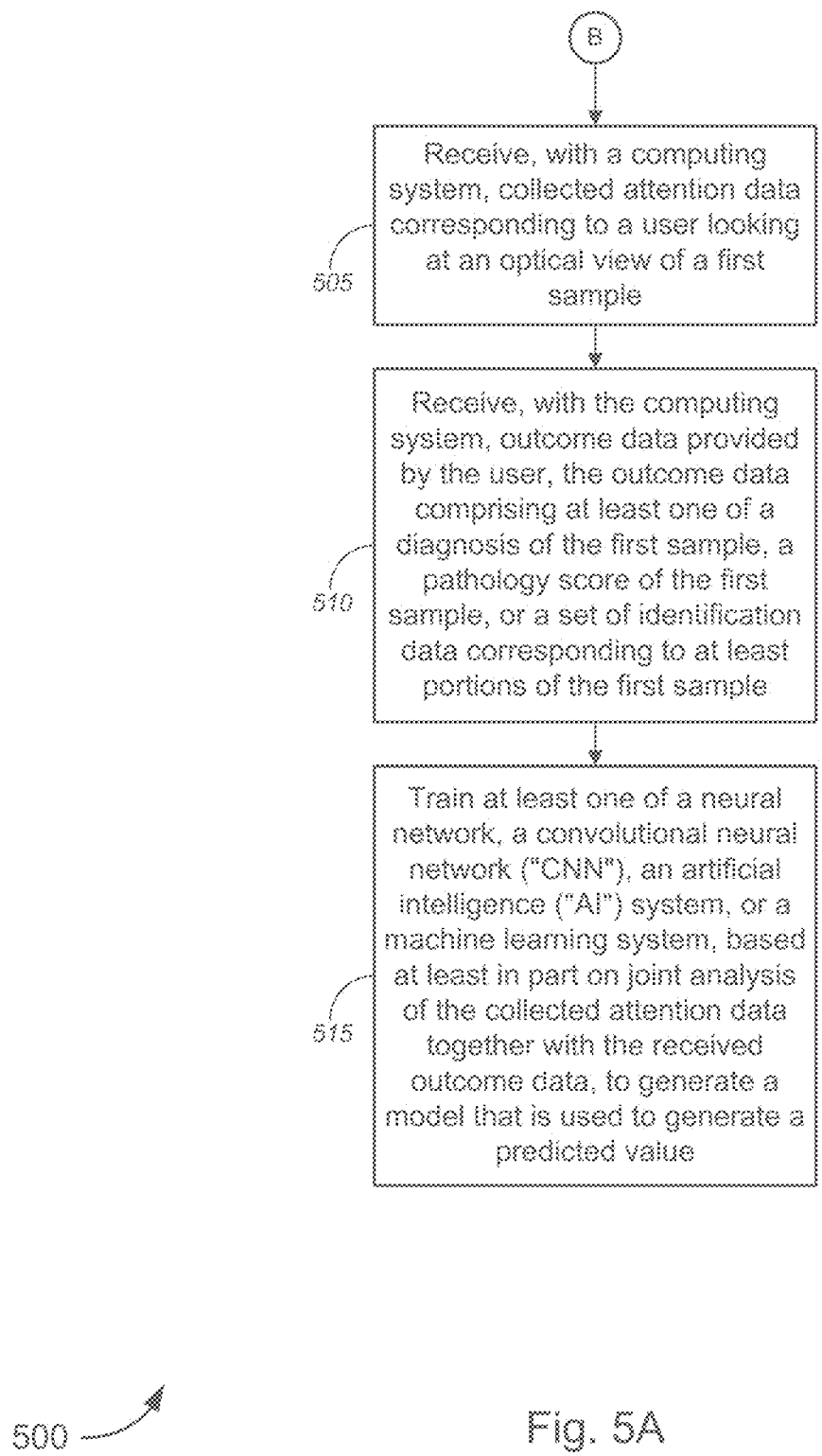
FIGS. 5A-5D are flow diagrams illustrating a method for implementing training of an AI system based on annotation data collected using gaze-based tracking, in accordance with various embodiments.

With reference to the non-limiting embodiment of FIG. 5A, method 500, at block 505, might comprise receiving, with a computing system, collected attention data corresponding to a user looking at an optical view of a first sample. At block 510, method 500 might comprise receiving, with the computing system, outcome data provided by the user, the outcome data comprising at least one of a diagnosis of the first sample, a pathology score of the first sample, or a set of identification data corresponding to at least portions of the first sample. Method 500 might further comprise, at block 515, training at least one of a neural network, a convolutional neural network ("CNN"), an artificial intelligence ("AI") system, or a machine learning system, based at least in part on joint analysis of the collected attention data together with the received outcome data, to generate a model that is used to generate a predicted value.

In some embodiments, the first sample might be contained within at least one of a microscope slide, a transparent sample cartridge, a vial, a tube, a capsule, a flask, a vessel, a receptacle, a microarray, or a microfluidic chip, and/or the like. According to some embodiments, the predicted value might include, without limitation, at least one of a predicted clinical outcome or predicted attention data, and/or the like.

Figures 5B, 5C:
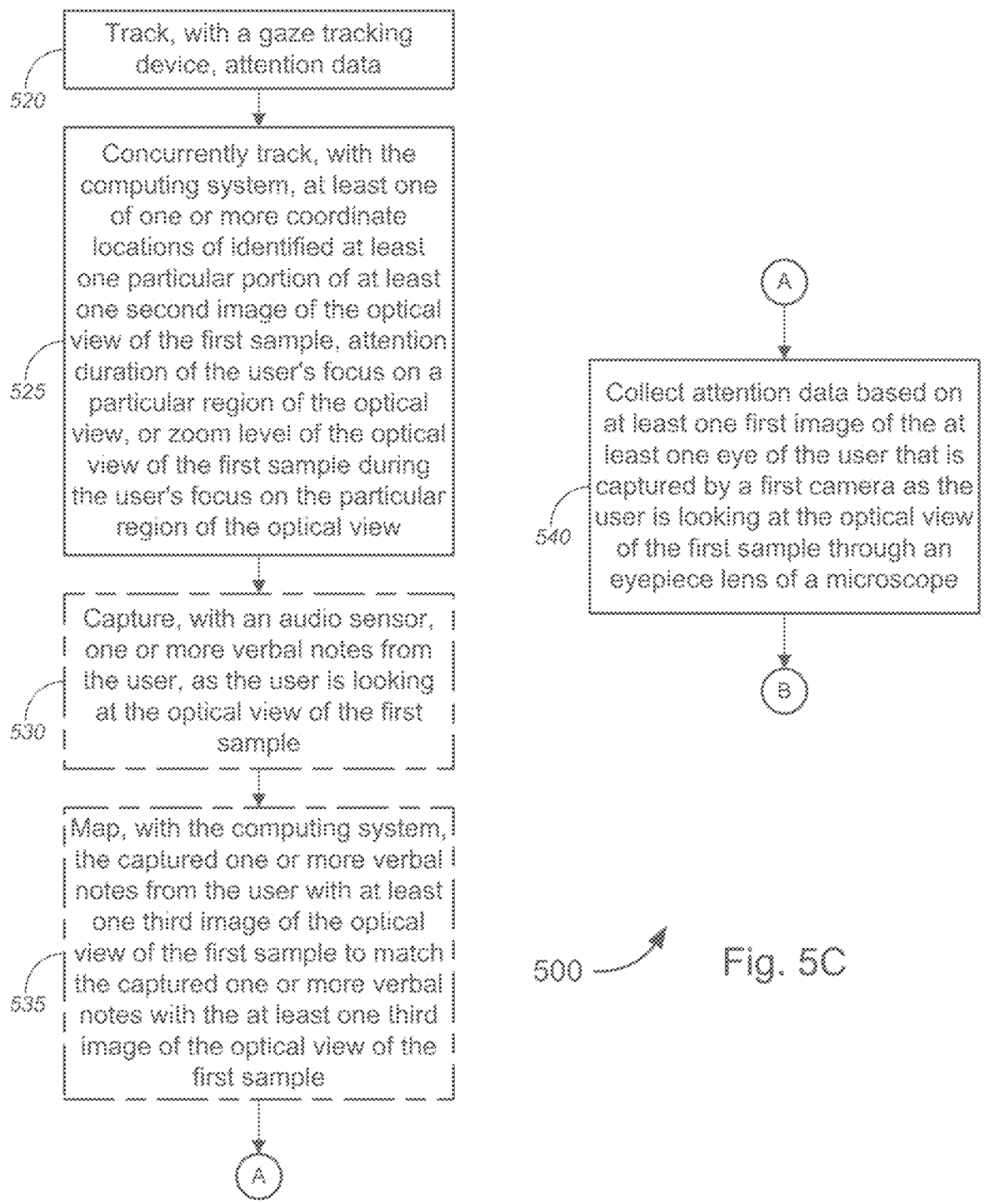

Turning to FIG. 5B, method 500 might further comprise tracking, with a gaze tracking device, attention data (block 520); and concurrently tracking, with the computing system, at least one of one or more coordinate locations of identified at least one particular portion of at least one second image of the optical view of the first sample, attention duration of the user's focus on a particular region of the optical view, or zoom level of the optical view of the first sample during the user's focus on the particular region of the optical view (block 525).

In some instances, method 500 might further comprise capturing, with an audio sensor, one or more verbal notes from the user, as the user is looking at the optical view of the first sample (optional block 530); and mapping, with the computing system, the captured one or more verbal notes from the user with at least one third image of the optical view of the first sample to match the captured one or more verbal notes with the at least one third image of the optical view of the first sample (optional block 535). Method 500 might continue onto the process at block 540 in FIG. 5C or onto the process at block 545 in FIG. 5D following the circular marker denoted, "A."

At block 540 in FIG. 5C (following the circular marker denoted, "A"), method 500 might comprise collecting attention data based on at least one first image of the at least one eye of the user that is captured by a first camera as the user is looking at the optical view of the first sample through an eyepiece lens of a microscope. In some embodiments, the microscope might include, without limitation, two or more of a plurality of mirrors, a plurality of dichroic mirrors, or a plurality of half-mirrors, and/or the like, that reflect or pass-through at least one of the optical view of the first sample as viewed through the eyepiece lens or an optical view of the at least one eye of the user as viewed through the eyepiece lens and as captured by the first camera as the at least one first image. Method 500 might return to the process at block 505 in FIG. 5A following the circular marker denoted, "B."

Figure 5D:
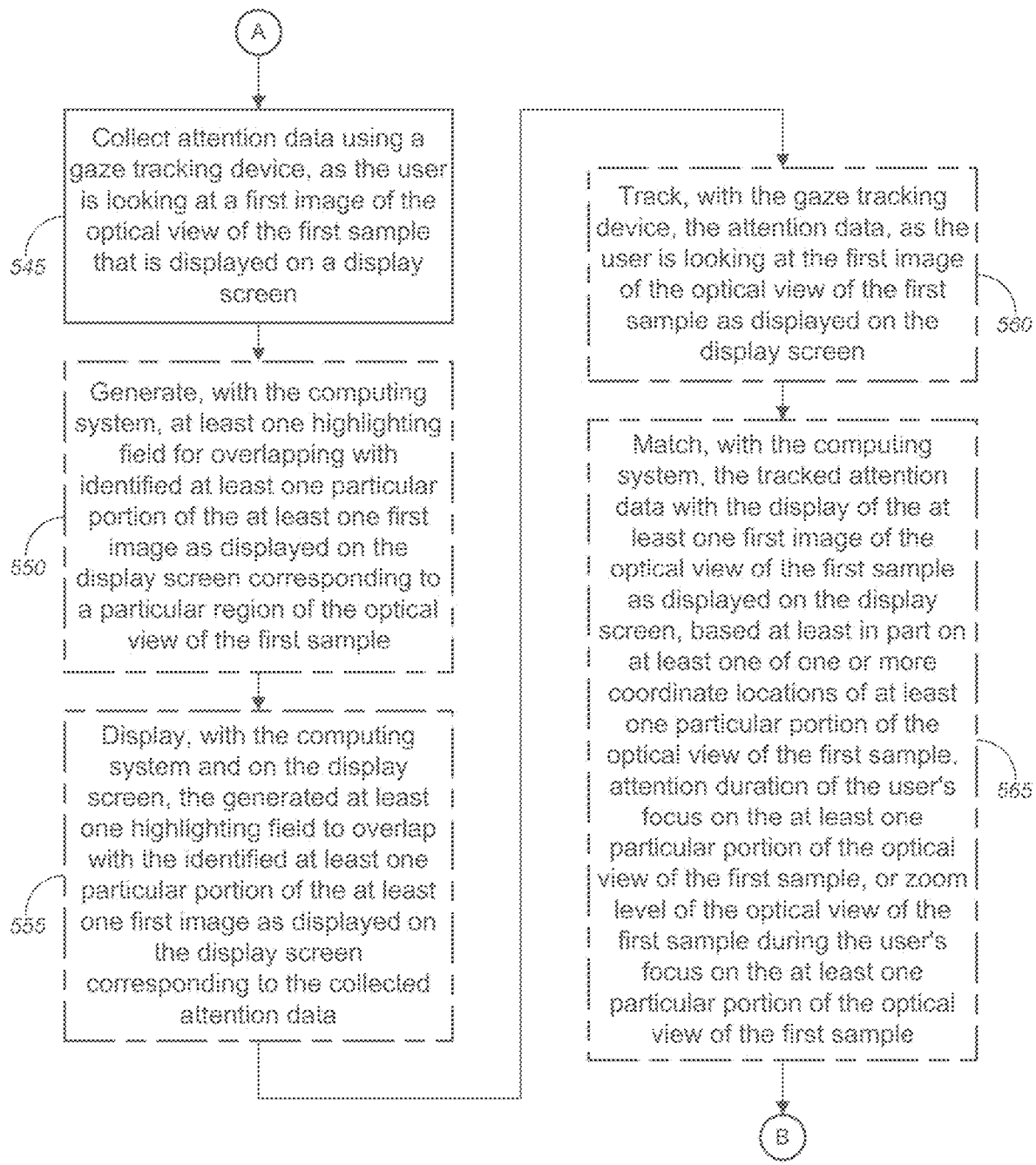

Alternatively, at block 545 in FIG. 5D (following the circular marker denoted, "A"), method 500 might comprise collecting attention data using a gaze tracking device, as the user is looking at a first image of the optical view of the first sample that is displayed on a display screen.

According to some embodiments, collecting the attention data might be performed without interrupting, slowing, or encumbering the user as the user is providing the outcome data either while diagnosing the first sample using the microscope or while diagnosing an image of the first sample as displayed on the display screen. In some embodiments, the collected attention data might include, but is not limited to, at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample, and/or the like.

Merely by way of example, in some cases, method 500 might further comprise generating, with the computing system, at least one highlighting field for overlapping with identified at least one particular portion of the at least one first image as displayed on the display screen corresponding to a particular region of the optical view of the first sample (optional block 550); displaying, with the computing system and on the display screen, the generated at least one highlighting field to overlap with the identified at least one particular portion of the at least one first image as displayed on the display screen corresponding to the collected attention data (optional block 555); tracking, with the gaze tracking device, the attention data, as the user is looking at the first image of the optical view of the first sample as displayed on the display screen (optional block 560); and matching, with the computing system, the tracked attention data with the display of the at least one first image of the optical view of the first sample as displayed on the display screen, based at least in part on at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample (optional block 565). In some instances, the at least one highlighting field might each include, but is not limited to, at least one of a color, a shape, or a highlighting effect, and/or the like. In some cases, the highlighting effect might include, without limitation, at least one of outlining effect, shadowing effect, patterning effect, heat map effect, or jet colormap effect, and/or the like.

Method 500 might return to the process at block 505 in FIG. 5A following the circular marker denoted, "B."

Figure 6:
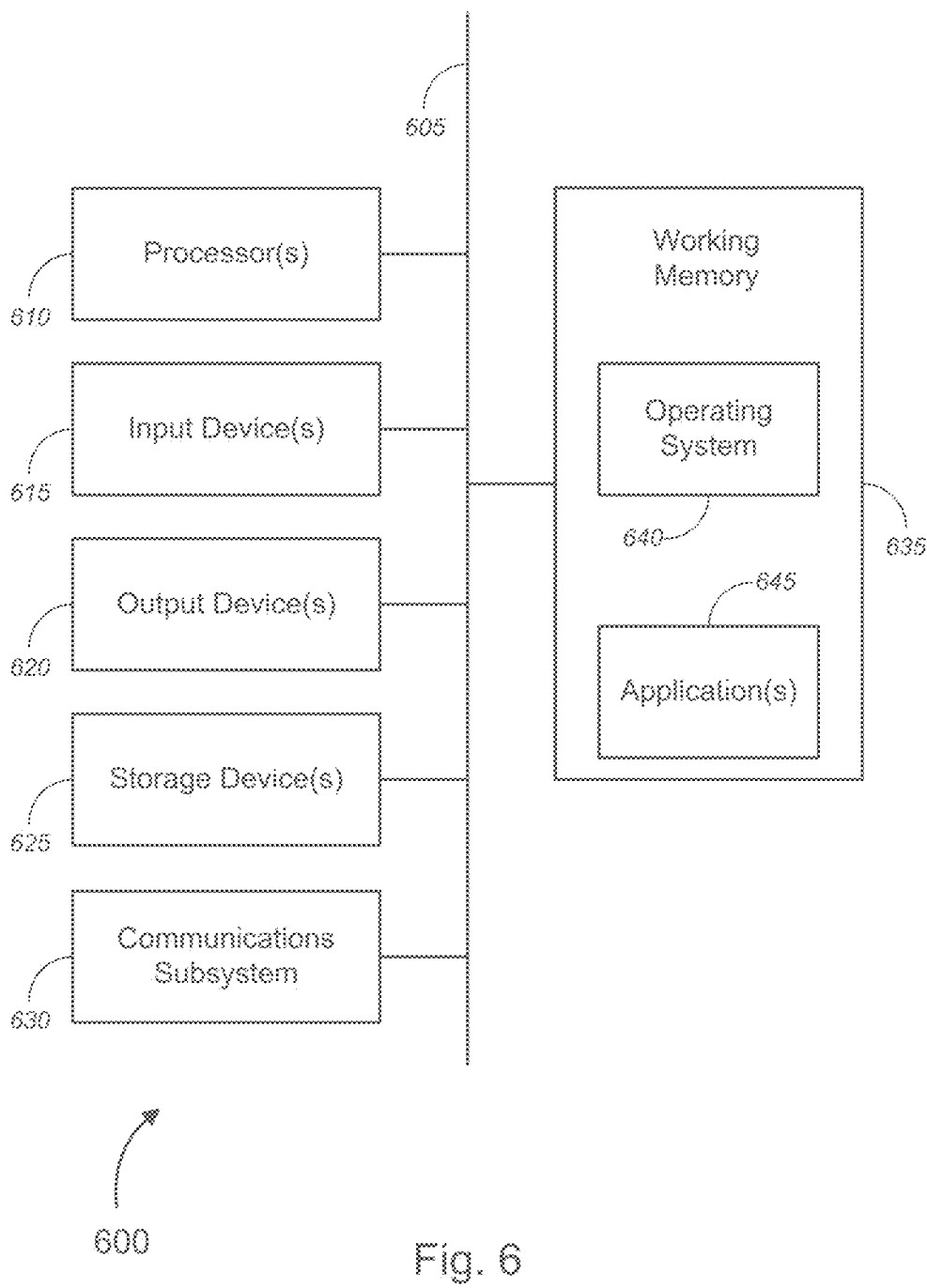
FIG. 6 is a block diagram illustrating an exemplary computer or system hardware architecture, in accordance with various embodiments.

FIG. 6 is a block diagram illustrating an exemplary computer or system hardware architecture, in accordance with various embodiments. FIG. 6 provides a schematic illustration of one embodiment of a computer system 600 of the service provider system hardware that can perform the methods provided by various other embodiments, as described herein, and/or can perform the functions of computer or hardware system (i.e., computing systems 105a, 105b, 205, and 305, microscopes 115, 310, and 310', display devices 120, 210, and 395, and user device(s) 140, etc.), as described above. It should be noted that FIG. 6 is meant only to provide a generalized illustration of various components, of which one or more (or none) of each may be utilized as appropriate. FIG. 6, therefore, broadly illustrates how individual system elements may be implemented in a relatively separated or relatively more integrated manner.

The computer or hardware system 600—which might represent an embodiment of the computer or hardware system (i.e., computing systems 105a, 105b, 205, and 305, microscopes 115, 310, and 310', display devices 120, 210, and 395, and user device(s) 140, etc.), described above with respect to FIGS. 1-5—is shown comprising hardware elements that can be electrically coupled via a bus 605 (or may otherwise be in communication, as appropriate). The hardware elements may include one or more processors 610, including, without limitation, one or more general-purpose processors and/or one or more special-purpose processors (such as microprocessors, digital signal processing chips, graphics acceleration processors, and/or the like); one or more input devices 615, which can include, without limitation, a mouse, a keyboard, and/or the like; and one or more output devices 620, which can include, without limitation, a display device, a printer, and/or the like.

The computer or hardware system 600 may further include (and/or be in communication with) one or more storage devices 625, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 600 might also include a communications subsystem 630, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 630 may permit data to be exchanged with a network (such as the network described below, to name one example), with other computer or hardware systems, and/or with any other devices described herein. In many embodiments, the computer or hardware system 600 will further comprise a working memory 635, which can include a RAM or ROM device, as described above.

The computer or hardware system 600 also may comprise software elements, shown as being currently located within the working memory 635, including an operating system 640, device drivers, executable libraries, and/or other code, such as one or more application programs 645, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 625 described above. In some cases, the storage medium might be incorporated within a computer system, such as the system 600. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 600 and/or might take the form of source and/or installable code, which, upon compilation and/or installation on the computer or hardware system 600 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 600) to perform methods in accordance with various embodiments of the invention. According to a set of embodiments, some or all of the procedures of such methods are performed by the computer or hardware system 600 in response to processor 610 executing one or more sequences of one or more instructions (which might be incorporated into the operating system 640 and/or other code, such as an application program 645) contained in the working memory 635. Such instructions may be read into the working memory 635 from another computer readable medium, such as one or more of the storage device(s) 625. Merely by way of example, execution of the sequences of instructions contained in the working memory 635 might cause the processor(s) 610 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 600, various computer readable media might be involved in providing instructions/code to processor(s) 610 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 625. Volatile media includes, without limitation, dynamic memory, such as the working memory 635. In some alternative embodiments, a computer readable medium may take the form of transmission media, which includes, without limitation, coaxial cables, copper wire, and fiber optics, including the wires that comprise the bus 605, as well as the various components of the communication subsystem 630 (and/or the media by which the communications subsystem 630 provides communication with other devices). In an alternative set of embodiments, transmission media can also take the form of waves (including without limitation radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 610 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 600. These signals, which might be in the form of electromagnetic signals, acoustic signals, optical signals, and/or the like, are all examples of carrier waves on which instructions can be encoded, in accordance with various embodiments of the invention.

The communications subsystem 630 (and/or components thereof) generally will receive the signals, and the bus 605 then might carry the signals (and/or the data, instructions, etc. carried by the signals) to the working memory 635, from which the processor(s) 605 retrieves and executes the instructions. The instructions received by the working memory 635 may optionally be stored on a storage device 625 either before or after execution by the processor(s) 610.

As noted above, a set of embodiments comprises methods and systems for implementing annotation data collection, and, more particularly, to methods, systems, and apparatuses for implementing annotation data collection using gaze-based tracking and/or training of an artificial intelligence ("AI") system (which might include, without limitation, at least one of a neural network, a convolutional neural network ("CNN"), a learning algorithm-based system, or a machine learning system, and/or the like) based on annotation data collected using gaze-based tracking. FIG. 7 illustrates a schematic diagram of a system 700 that can be used in accordance with one set of embodiments. The system 700 can include one or more user computers, user devices, or customer devices 705. A user computer, user device, or customer device 705 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 705 can also have any of a variety of applications, including one or more applications configured to perform methods provided by various embodiments (as described above, for example), as well as one or more office applications, database client and/or server applications, and/or web browser applications. Alternatively, a user computer, user device, or customer device 705 can be any other electronic device, such as a thin-client computer, Internet-enabled mobile telephone, and/or personal digital assistant, capable of communicating via a network (e.g., the network(s) 710 described below) and/or of displaying and navigating web pages or other types of electronic documents. Although the exemplary system 700 is shown with two user computers, user devices, or customer devices 705, any number of user computers, user devices, or customer devices can be supported.

Certain embodiments operate in a networked environment, which can include a network(s) 710. The network(s) 710 can be any type of network familiar to those skilled in the art that can support data communications using any of a variety of commercially-available (and/or free or proprietary) protocols, including, without limitation, TCP/IP, SNA™, IPX™, AppleTalk™, and the like. Merely by way of example, the network(s) 710 (similar to network(s) 150 of FIG. 1, or the like) can each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 715. Each of the server computers 715 may be configured with an operating system, including, without limitation, any of those discussed above, as well as any commercially (or freely) available server operating systems. Each of the servers 715 may also be running one or more applications, which can be configured to provide services to one or more clients 705 and/or other servers 715.

Merely by way of example, one of the servers 715 might be a data server, a web server, a cloud computing device(s), or the like, as described above. The data server might include (or be in communication with) a web server, which can be used, merely by way of example, to process requests for web pages or other electronic documents from user computers 705. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 705 to perform methods of the invention.

The server computers 715, in some embodiments, might include one or more application servers, which can be configured with one or more applications accessible by a client running on one or more of the client computers 705 and/or other servers 715. Merely by way of example, the server(s) 715 can be one or more general purpose computers capable of executing programs or scripts in response to the user computers 705 and/or other servers 715, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™, IBM™, and the like, which can process requests from clients (including, depending on the configuration, dedicated database clients, API clients, web browsers, etc.) running on a user computer, user device, or customer device 705 and/or another server 715. In some embodiments, an application server can perform one or more of the processes for implementing annotation data collection, and, more particularly, to methods, systems, and apparatuses for implementing annotation data collection using gaze-based tracking and/or training of an AI system based on annotation data collected using gaze-based tracking, as described in detail above. Data provided by an application server may be formatted as one or more web pages (comprising HTML, JavaScript, etc., for example) and/or may be forwarded to a user computer 705 via a web server (as described above, for example). Similarly, a web server might receive web page requests and/or input data from a user computer 705 and/or forward the web page requests and/or input data to an application server. In some cases, a web server may be integrated with an application server.

In accordance with further embodiments, one or more servers 715 can function as a file server and/or can include one or more of the files (e.g., application code, data files, etc.) necessary to implement various disclosed methods, incorporated by an application running on a user computer 705 and/or another server 715. Alternatively, as those skilled in the art will appreciate, a file server can include all necessary files, allowing such an application to be invoked remotely by a user computer, user device, or customer device 705 and/or server 715.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 720a-720n (collectively, "databases 720"). The location of each of the databases 720 is discretionary: merely by way of example, a database 720a might reside on a storage medium local to (and/or resident in) a server 715a (and/or a user computer, user device, or customer device 705). Alternatively, a database 720n can be remote from any or all of the computers 705, 715, so long as it can be in communication (e.g., via the network 710) with one or more of these. In a particular set of embodiments, a database 720 can reside in a storage-area network ("SAN") familiar to those skilled in the art. (Likewise, any necessary files for performing the functions attributed to the computers 705, 715 can be stored locally on the respective computer and/or remotely, as appropriate.) In one set of embodiments, the database 720 can be a relational database, such as an Oracle database, that is adapted to store, update, and retrieve data in response to SQL-formatted commands. The database might be controlled and/or maintained by a database server, as described above, for example.

According to some embodiments, system 700 might further comprise a computing system 725 (similar to computing systems 105a, 205, and 305 of FIGS. 1, 2A, and 3A, or the like) and corresponding database(s) 730 (similar to database(s) 110a of FIG. 1, or the like). System 700 might further comprise a microscope 735 (similar to microscopes 115 and 310 of FIGS. 1 and 3, or the like) and a display device 740 (similar to display devices 120 and 210 of FIGS. 1 and 2, or the like) that are used to allow a user 745 to look at an optical view of a first sample (e.g., as shown in FIGS. 2B and 3B, or the like), while a camera 750 might capture images of the user 745 (in some cases, capturing images of at least one eye of the user 745) while the user 745 is within the field of view ("FOV") 750a of camera 750. In some cases, the camera 750 might include, without limitation, one or more eye tracking sensors, one or more motion sensors, or one or more tracking sensors, and/or the like. System 700 might further comprise one or more audio sensors 755 (optional; similar to audio sensor(s) 135 of FIG. 1, or the like; including, but not limited to, one or more microphones, one or more voice recorders, or one or more audio recorders, and/or the like) and one or more user devices 760 (optional; similar to user device(s) 140 of FIG. 1, or the like; including, without limitation, smart phones, mobile phones, tablet computers, laptop computers, desktop computers, or monitors, and/or the like). Alternative, or additional, to computing system 725 and corresponding database(s), system 700 might further comprise remote computing system 770 (similar to remote computing system 105b of FIG. 1, or the like) and corresponding database(s) 775 (similar to database(s) 110b of FIG. 1, or the like). In some embodiments, system 700 might further comprise artificial intelligence ("AI") system 780.

In operation, the microscope 735 might project an optical view of a first sample to eyepiece lens(es) through which at least one eye of user 745 is viewing. The camera 750 (or gaze tracking device) might capture at least one first image of at least one eye of a user 745, as the user 745 is looking at the optical view of the first sample. Computing system 725, user device 705a, user device 705b, user device(s) 760, server 715a or 715b, and/or remote computing system(s) 770 (collectively, "computing system" or the like) might analyze the captured at least one first image of the at least one eye of the user 745 and the captured at least one second image of the optical view of the first sample to determine whether the at least one eye of the user 745 is focused on a particular region of the optical view of the first sample. Based on a determination that the at least one eye of the user 745 is focused on a particular region of the optical view of the first sample, the computing system might identify at least one particular portion of the at least one second image corresponding to the particular region of the optical view of the first sample. The computing system might collect attention data comprising the identified at least one particular portion of the at least one second image, and might store the collected attention data in a database 720a-720n, 730, or 775. According to some embodiments, collecting the attention data might be performed without interrupting, slowing, or encumbering the user as the user is providing the outcome data either while diagnosing the first sample using microscope 735 or while diagnosing an image of the first sample as displayed on a display screen 740. In some instances, the collected attention data might include, but is not limited to, at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample, and/or the like. In some cases, the identified at least one particular portion of the at least one second image corresponding to the particular region of the optical view of the first sample might include, without limitation, at least one of one or more specific cells, one or more specific tissues, one or more specific structures, or one or more molecules, and/or the like.

In some embodiments, the computing system might generate at least one highlighting field in the at least one second image covering the identified at least one particular portion of the at least one second image corresponding to the particular region of the optical view of the first sample. In some cases, the at least one highlighting field might each include, without limitation, at least one of a color, a shape, or a highlighting effect, and/or the like, where the highlighting effect might include, but is not limited to, at least one of outlining effect, shadowing effect, patterning effect, heat map effect, or jet colormap effect, and/or the like.

According to some embodiments, the at least one second image might be displayed on a display screen (e.g., display screen of display device 740, or the like). Capturing the at least one first image of the at least one eye of the user 745 might comprise capturing, with camera 750, the at least one first image of the at least one eye of the user 745, as the user 745 is looking at the image(s) or video(s) of the optical view of the first sample as displayed on the display screen of the display device 740 as the at least one second image. Alternative to camera 750, the gaze tracking device might be used to collect attention data, as the user is looking at the images or videos of the first sample that are displayed on the display screen of the display device 740. Identifying the at least one particular portion of the at least one second image corresponding to the particular region of the optical view of the first sample might comprise identifying, with the computing system, at least one particular portion of the at least one second image as displayed on the display screen corresponding to the particular region of the optical view of the first sample. The computing system might display, on the display screen (e.g., display screen of display device 740, or the like), the at least one second image with the generated at least one highlighting field covering the identified at least one particular portion of the at least one second image corresponding to the particular region of the optical view of the first sample.

In some embodiments, the display of the at least one second image on the display screen may be shifted in response to commands by the user. In some instances, shifting display of the at least one second image might comprise at least one of horizontal shifting, vertical shifting, panning, tilting, zooming in, or zooming out, and/or the like, of the at least one second image on the display screen. The camera 750 might track movement of the at least one eye of the user 745, as the user 745 is looking at the shifting display of the at least one second image on the display screen. The computing system might match the tracked movement of the at least one eye of the user 745 with the shifting display of the at least one second image on the display screen, based at least in part on one or more of the tracked movement of the at least one eye of the user 745, the identified at least one particular portion of the at least one second image corresponding to the particular region of the optical view of the first sample, or the at least one of horizontal shifting, vertical shifting, panning, tilting, zooming in on, or zooming out of the at least one second image on the display screen, and/or the like. Alternative to using camera 750, the gaze tracking device might be used to collect additional attention data, as the user is looking at the shifting display of the at least one second image on the display screen of display device 740.

Alternatively, microscope 735 might project the optical view of the first sample to an eyepiece lens through which the at least one eye of the user 745 is viewing. A second camera might capture the at least one second image of the optical view of the first sample. In some cases, capturing the at least one first image of the at least one eye of the user 745 might comprise capturing, with the first camera, the at least one first image of the at least one eye of the user 745, as the user 745 is looking at the optical view of the first sample through the eyepiece lens. Identifying the at least one particular portion of the at least one second image corresponding to the particular region of the optical view of the first sample might comprise identifying, with the computing system, at least one particular portion of the at least one second image as viewed through the eyepiece lens corresponding to the particular region of the optical view of the first sample. Generating the at least one highlighting field in the at least one second image covering the identified at least one particular portion of the at least one second image corresponding to the particular region of the optical view of the first sample might comprise generating, with the computing system, at least one highlighting field for overlapping with the identified at least one particular portion of the at least one second image as viewed through the eyepiece lens corresponding to the particular region of the optical view of the first sample. The computing system might project, using a projection device, the generated at least one highlighting field to overlap with the identified at least one particular portion of the at least one second image as viewed through the eyepiece lens corresponding to the particular region of the optical view of the first sample. Alternatively, or additionally, the computing system might display, on the display screen (e.g., display screen of display device 740, or the like), the at least one second image with the generated at least one highlighting field covering the identified at least one particular portion of the at least one second image corresponding to the particular region of the optical view of the first sample.

In some instances, the first camera might be one of an infrared ("IR") camera, a back-reflected IR camera, a visible-color camera, a light source, or a location photodiode, and/or the like. In some cases, the microscope might include, without limitation, two or more of a plurality of mirrors, a plurality of dichroic mirrors, or a plurality of half-mirrors that reflect or pass-through at least one of the optical view of the first sample as viewed through the eyepiece lens, an optical view of the at least one eye of the user as viewed through the eyepiece lens and as captured by the first camera as the at least one first image, or projection of the generated at least one highlighting field through the eyepiece lens to the at least one eye of the user, and/or the like.

According to some embodiments, projection of the optical view of the first sample to the eyepiece lens may be shifted, by at least one of adjusting an X-Y stage on which a microscope slide containing the first sample, exchanging objective or zoom lenses, or adjusting focus of the eyepiece lens, and/or the like. The camera 750 might track movement of the at least one eye of the user 745, as the user 745 is looking at the shifting projection of the optical view of the first sample to the eyepiece lens. The computing system might match the tracked movement of the at least one eye of the user 745 with the shifting projection of the optical view of the first sample to the eyepiece lens, based at least in part on one or more of the tracked movement of the at least one eye of the user 745, the identified at least one particular portion of the at least one second image corresponding to the particular region of the optical view of the first sample, or the at least one of adjusting an X-Y stage on which a microscope slide containing the first sample, exchanging objective or zoom lenses, or adjusting focus of the eyepiece lens, and/or the like.

Alternatively, or additionally, the one or more audio sensors 755 might capture one or more verbal notes from the user 745, as the user 745 is looking at the optical view of the first sample. The computing system might map the captured one or more verbal notes from the user 745 with the at least one second image of the optical view of the first sample to match the captured one or more verbal notes with the at least one second image of the optical view of the first sample.

According to some embodiments, the computing system might receive outcome data provided by the user, the outcome data comprising at least one of a diagnosis of the first sample, a pathology score of the first sample, or a set of identification data corresponding to at least portions of the first sample. The computing system might train AI system 780 (which might generally include, without limitation, at least one of a neural network, a convolutional neural network ("CNN"), a learning algorithm-based system, or a machine learning system, and/or the like), based at least in part on at least one of analysis of the captured at least one first image of the at least one eye of the user and the captured at least one second image of the optical view of the first sample or joint analysis of the collected attention data together with the received outcome data, to generate a model that is used to generate a predicted value. In some embodiments, the predicted value might include, but is not limited to, at least one of a predicted clinical outcome or predicted attention data, and/or the like.

These and other functions of the system 700 (and its components) are described in greater detail above with respect to FIGS. 1-4.

Additional exemplary embodiments are now described.

According to an aspect of some embodiments of the present invention there is provided a method, comprising:
projecting, with a microscope, an optical view of a first sample to an eyepiece lens through which at least one eye of a user is viewing, capturing, with a first camera, at least one first image of the at least one eye of the user, as the user is looking at the optical view of the first sample through the eyepiece lens, capturing, with a second camera, at least one second image of the optical view of the first sample, analyzing, with a computing system, the captured at least one first image of the at least one eye of the user and the captured at least one second image of the optical view of the first sample to determine whether the at least one eye of the user is focused on a particular region of the optical view of the first sample, based on a determination that the at least one eye of the user is focused on a particular region of the optical view of the first sample, identifying, with the computing system, at least one particular portion of the at least one second image as viewed through the eyepiece lens corresponding to the particular region of the optical view of the first sample, collecting, with the computing system, attention data comprising the identified at least one particular portion of the at least one second image, and storing, in a database, the collected attention data.

Optionally, the first sample is contained within at least one of a microscope slide, a transparent sample cartridge, a vial, a tube, a capsule, a flask, a vessel, a receptacle, a microarray, or a microfluidic chip.

Optionally, the first camera is one of an infrared ("IR") camera, a back-reflected IR camera, a visible-color camera, a light source, or a location photodiode.

Optionally, the microscope comprises two or more of a plurality of mirrors, a plurality of dichroic mirrors, or a plurality of half-mirrors that reflect or pass-through at least one of the optical view of the first sample as viewed through the eyepiece lens or an optical view of the at least one eye of the user as viewed through the eyepiece lens and as captured by the first camera as the at least one first image.

Optionally, the identified at least one particular portion of the at least one second image corresponding to the particular region of the optical view of the first sample comprises at least one of one or more specific cells, one or more specific tissues, one or more specific structures, or one or more molecules.

Optionally, identifying the at least one particular portion of the at least one second image comprises determining, with the computing system, coordinate locations within the at least one second image of the optical view corresponding to the identified at least one particular portion of the at least one second image.

Optionally, further comprising:
receiving, with the computing system, outcome data provided by the user, the outcome data comprising at least one of a diagnosis of the first sample, a pathology score of the first sample, or a set of identification data corresponding to at least portions of the first sample, and training at least one of a neural network, a convolutional neural network ("CNN"), an artificial intelligence ("AI") system, or a machine learning system, based at least in part on at least one of analysis of the captured at least one first image of the at least one eye of the user and the captured at least one second image of the optical view of the first sample or joint analysis of the collected attention data together with the received outcome data, to generate a model that is used to generate a predicted value.

Optionally, the predicted value comprises at least one of a predicted clinical outcome or predicted attention data.

Optionally, collecting the attention data is performed without interrupting, slowing, or encumbering the user as the user is providing the outcome data while diagnosing the first sample using the microscope.

Optionally, further comprising:
tracking, with the first camera, movement of the at least one eye of the user, and concurrently tracking, with the computing system, at least one of one or more coordinate locations of the identified at least one particular portion of the at least one second image, attention duration of the user's focus on the particular region of the optical view, or zoom level of the optical view of the first sample during the user's focus on the particular region of the optical view.

Optionally, determining whether the at least one eye of the user is focused on a particular region of the optical view of the first sample comprises determining whether the at least one eye of the user is focused on a particular region of the optical view of the first sample, based at least in part on at least one of the one or more coordinate locations of the identified at least one particular portion of the at least one second image, the attention duration of the user's focus on the particular region of the optical view, or the zoom level of the optical view of the first sample during the user's focus on the particular region of the optical view.

Optionally, further comprising:
capturing, with an audio sensor, one or more verbal notes from the user, as the user is looking at the optical view of the first sample, and mapping, with the computing system, the captured one or more verbal notes from the user with the at least one second image of the optical view of the first sample to match the captured one or more verbal notes with the at least one second image of the optical view of the first sample.

According to an aspect of some embodiments of the present invention there is provided a system, comprising:
a microscope configured to project an optical view of a first sample to an eyepiece lens through which at least one eye of a user is viewing, a first camera configured to capture at least one first image of the at least one eye of the user, as the user is looking at the optical view of the first sample through the eyepiece lens, a second camera configured to capture at least one second image of the optical view of the first sample, a computing system, comprising:
at least one first processor, and
a first non-transitory computer readable medium communicatively coupled to the at least one first processor, the first non-transitory computer readable medium having stored thereon computer software comprising a first set of instructions that, when executed by the at least one first processor, causes the computing system to:

analyze the captured at least one first image of the at least one eye of the user and the captured at least one second image of the optical view of the first sample to determine whether the at least one eye of the user is focused on a particular region of the optical view of the first sample, based on a determination that the at least one eye of the user is focused on a particular region of the optical view of the first sample, identify at least one particular portion of the at least one second image as viewed through the eyepiece lens corresponding to the particular region of the optical view of the first sample,
collect attention data comprising the identified at least one particular portion of the at least one second image, and
store, in a database, the collected attention data.

Optionally, the first set of instructions, when executed by the at least one first processor, further causes the computing system to:
receive outcome data provided by the user, the outcome data comprising at least one of a diagnosis of the first sample, a pathology score of the first sample, or a set of identification data corresponding to at least portions of the first sample, and
train at least one of a neural network, a convolutional neural network ("CNN"), an artificial intelligence ("AI") system, or a machine learning system, based at least in part on at least one of analysis of the captured at least one first image of the at least one eye of the user and the captured at least one second image of the optical view of the first sample or joint analysis of the collected attention data together with the received outcome data, to generate a model that is used to generate a predicted value.

Optionally, the predicted value comprises at least one of a predicted clinical outcome or predicted attention data.

Optionally,
the first camera is further configured to track movement of the at least one eye of the user,
the computing system is further configured to concurrently track at least one of one or more coordinate locations, attention duration, or zoom level of the optical view of the first sample, and
determining whether the at least one eye of the user is focused on a particular region of the optical view of the first sample comprises determining whether the at least one eye of the user is focused on a particular region of the optical view of the first sample, based at least in part on one or more of tracking of the one or more coordinate locations of attention gaze, tracking of the at least one of movement and zoom level of the optical view of the first sample, or a determination that the at least one eye of the user is lingering on a portion of the optical view of the first sample.

Optionally, further comprising:
an audio sensor configured to capture one or more verbal notes from the user, as the user is looking at the optical view of the first sample,
wherein the first set of instructions, when executed by the at least one first processor, further causes the computing system to:
map the captured one or more verbal notes from the user with the at least one second image of the optical view of the first sample to match the captured one or more verbal notes with the at least one second image of the optical view of the first sample.

According to an aspect of some embodiments of the present invention there is provided a method, comprising:
receiving at least one first image of at least one eye of a user that is captured by a first camera, as the user is looking at an optical view of a first sample through an eyepiece lens of a microscope,
receiving at least one second image of the optical view of the first sample that is captured by a second camera,
analyzing, with a computing system, the at least one first image and the at least one second image to determine whether the at least one eye of the user is focused on a particular region of the optical view of the first sample,
tracking, with the computing system, attention of the user based on the analysis, and
collecting, with the computing system, attention data based on the tracking.

According to an aspect of some embodiments of the present invention there is provided a method, comprising:
receiving, with a computing system, collected attention data corresponding to a user looking at an optical view of a first sample,
receiving, with the computing system, outcome data provided by the user, the outcome data comprising at least one of a diagnosis of the first sample, a pathology score of the first sample, or a set of identification data corresponding to at least portions of the first sample, and
training at least one of a neural network, a convolutional neural network ("CNN"), an artificial intelligence ("AI") system, or a machine learning system, based at least in part on joint analysis of the collected attention data together with the received outcome data, to generate a model that is used to generate a predicted value.

Optionally, the first sample is contained within at least one of a microscope slide, a transparent sample cartridge, a vial, a tube, a capsule, a flask, a vessel, a receptacle, a microarray, or a microfluidic chip.

Optionally, the predicted value comprises at least one of a predicted clinical outcome or predicted attention data.

Optionally, collecting the attention data is performed without interrupting, slowing, or encumbering the user as the user is providing the outcome data either while diagnosing the first sample using a microscope or while diagnosing an image of the first sample as displayed on a display screen.

Optionally, the collected attention data comprises at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample.

Optionally, the attention data is collected based on at least one first image of the at least one eye of the user that is captured by a first camera as the user is looking at the optical view of the first sample through an eyepiece lens of a microscope.

Optionally, the microscope comprises two or more of a plurality of mirrors, a plurality of dichroic mirrors, or a plurality of half-mirrors that reflect or pass-through at least one of the optical view of the first sample as viewed through the eyepiece lens or an optical view of the at least one eye of the user as viewed through the eyepiece lens and as captured by the first camera as the at least one first image.

Optionally, the attention data is collected using a gaze tracking device, as the user is looking at a first image of the optical view of the first sample that is displayed on a display screen.

Optionally, further comprising:
generating, with the computing system, at least one highlighting field for overlapping with identified at least one particular portion of the at least one first image as displayed on the display screen corresponding to a particular region of the optical view of the first sample.

Optionally, further comprising:
displaying, with the computing system and on the display screen, the generated at least one highlighting field to overlap with the identified at least one particular portion of the at least one first image as displayed on the display screen corresponding to the collected attention data, tracking, with the gaze tracking device, the attention data, as the user is looking at the first image of the optical view of the first sample as displayed on the display screen, and matching, with the computing system, the tracked attention data with the display of the at least one first image of the optical view of the first sample as displayed on the display screen, based at least in part on at least one of one or more coordinate locations of at least one particular portion of the optical view of the first sample, attention duration of the user's focus on the at least one particular portion of the optical view of the first sample, or zoom level of the optical view of the first sample during the user's focus on the at least one particular portion of the optical view of the first sample.

Optionally, the at least one highlighting field each comprises at least one of a color, a shape, or a highlighting effect, wherein the highlighting effect comprises at least one of outlining effect, shadowing effect, patterning effect, heat map effect, or jet colormap effect.

Optionally, further comprising:

tracking, with a gaze tracking device, attention data, and concurrently tracking, with the computing system, at least one of one or more coordinate locations of identified at least one particular portion of at least one second image of the optical view of the first sample, attention duration of the user's focus on a particular region of the optical view, or zoom level of the optical view of the first sample during the user's focus on the particular region of the optical view.

Optionally, further comprising:

capturing, with an audio sensor, one or more verbal notes from the user, as the user is looking at the optical view of the first sample, and mapping, with the computing system, the captured one or more verbal notes from the user with at least one third image of the optical view of the first sample to match the captured one or more verbal notes with the at least one third image of the optical view of the first sample.

According to an aspect of some embodiments of the present invention there is provided an apparatus, comprising:

at least one processor, and a non-transitory computer readable medium communicatively coupled to the at least one processor, the non-transitory computer readable medium having stored thereon computer software comprising a set of instructions that, when executed by the at least one processor, causes the apparatus to:

receive collected attention data corresponding to a user looking at an optical view of a first sample, receive outcome data provided by the user, the outcome data comprising at least one of a diagnosis of the first sample, a pathology score of the first sample, or a set of identification data corresponding to at least portions of the first sample, and train at least one of a neural network, a convolutional neural network ("CNN"), an artificial intelligence ("AI") system, or a machine learning system, based at least in part on joint analysis of the collected attention data together with the received outcome data, to generate a model that is used to generate a predicted value.

According to an aspect of some embodiments of the present invention there is provided a system, comprising:

a first camera configured to capture at least one first image of the at least one eye of the user, as the user is looking at the optical view of the first sample, a second camera configured to capture at least one second image of the optical view of the first sample, a computing system, comprising:

at least one first processor, and a first non-transitory computer readable medium communicatively coupled to the at least one first processor, the first non-transitory computer readable medium having stored thereon computer software comprising a first set of instructions that, when executed by the at least one first processor, causes the computing system to:

receive collected attention data corresponding to a user looking at the optical view of the first sample, receive outcome data provided by the user, the outcome data comprising at least one of a diagnosis of the first sample, a pathology score of the first sample, or a set of identification data corresponding to at least portions of the first sample, and train at least one of a neural network, a convolutional neural network ("CNN"), an artificial intelligence ("AI") system, or a machine learning system, based at least in part on joint analysis of the collected attention data together with the received outcome data, to generate a model that is used to generate a predicted value.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant machine learning models will be developed and the scope of the term machine learning model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method of automatically creating a training dataset comprising the step of:
   (a) generating the training dataset, using a processor, wherein the training set comprises a plurality of records, and at least one a record includes:
   an image of a sample of an object;
   an indication of monitored manipulations by a user of a presentation of the sample; and
   a ground truth indication of a monitored gaze of the user viewing the sample on a display or via an optical device mapped to pixels of the image of the sample, wherein the monitored gaze comprises at least one location of the sample the user has or is viewing and an amount of time spent viewing the at least one location;
   wherein the monitored gaze is represented as a weak annotation, and the at least one record further comprises at least one of the following additional ground truth labels of the image of the sample:
   when the sample comprises a sample of tissue of a subject: a pathology report created by the user viewing the sample, a pathological diagnosis created by the user viewing the sample, a sample score indicating a pathological evaluation for the sample created by the user viewing the sample, at least one clinical parameter of the subject whose sample is depicted in the sample, a history parameter of the subject, and/or an outcome of treatment administered to the subject,
   when the sample comprises a manufactured microarray: a user provided indication of at least one manufacturing defect, an indication of pass/fail quality assurance test, and
   when the sample comprises a live cell culture: a growth rate, a cell density, a homogeneity parameter, and/or a heterogeneity parameter, for the live cell culture.

2. The computer-implemented method of claim 1, wherein the samples of objects are selected from a group consisting of: biological samples, live cell culture in a microwell plate, slide of pathological tissue sample for generating a pathological report, a 3D radiology image, and a manufactured microarray for identification of manufacturing defects therein.

3. The computer-implemented method of claim 1, further comprising (b) training a machine learning model on the training dataset for generating an outcome of a target predicted gaze in response to an input of a target image of a target sample of a target object.

4. The computer-implemented method of claim 1, wherein the ground truth indication of monitored gaze comprises an aggregated amount of time the monitored gaze is mapped to each specific pixel of the image over a viewing time interval.

5. A computer-implemented method of automatically creating a training dataset, comprising the step of:
(a) generating the training dataset, using a processor, wherein the training set comprises a plurality of records and at least one record includes:
an image of a sample of an object;
an indication of monitored manipulations by a user of a presentation of the sample; and
a ground truth indication of a monitored gaze of the user viewing the sample on a display or via an optical device mapped to pixels of the image of the sample, wherein the monitored gaze comprises at least one location of the sample the user has or is viewing and an amount of time spent viewing the at least one location;
wherein the ground truth indication of monitored gaze comprises an aggregated amount of time the monitored gaze is mapped to each specific pixel of the image over a viewing time interval, and comprises at least one of:
(i) a heat map corresponding to the image of the sample, wherein a respective intensity of respective pixels of the heat map correlates with the aggregated amount of time the monitored gaze is mapped to each respective pixel, wherein pixels of the heat map are normalized to pixels indicating different actual sizes of the sample at a plurality of zoom levels defined by the monitored manipulations and/or to pixels located at different portions of the sample that are non-simultaneously visible on a display obtained by panning operations of the monitored manipulations and (ii) an overlay on the image of the sample, wherein features of the overlay corresponding to a spread of the gaze and/or indicate the aggregated amount of time.

6. The computer-implemented method of claim 1, wherein the ground truth indication of the monitored gaze comprises an ordered time sequence that dynamically maps adaptions of the monitored gaze of different fields of view being observed to different specific pixels over a viewing time interval.

7. The computer-implemented method of claim 6, wherein the ground truth indication of monitored gaze is depicted as at least one of: (i) a directed line overlaid on pixels of the image of the sample indicating dynamic adaptation of the monitored gaze, and (ii) presenting the ordered time sequence with an indication of amount of time spent at each field of view.

8. The computer-implemented method of claim 1, wherein the record of the training dataset further comprises ground truth indications of manipulations by the user performed to adjust the field of view of the sample, mapped to the ground truth indications of monitored gaze and to the pixels of the image.

9. The computer-implemented method of claim 1, wherein the sample is viewed as a magnification thereof, wherein the user manipulations being associated with the mapping of the monitored gaze to specific pixels of the image are selected from a group comprising: zoom in, zoom out, pan left, pan right, pan up, pan down, adjustment of light, adjustment of focus, and adjustment of scaling of the image.

10. The computer-implemented method of claim 1, wherein the sample is viewed via a microscope,
wherein monitoring gaze comprises obtaining gaze data from at least one first camera following pupils of the user while the user is viewing the sample under the microscope,
wherein the image of the sample being manipulated is captured by a second camera while the user is viewing the sample under the microscope,
further comprising obtaining a scanned image of the sample; and
registering the scanned image of the sample with the image of the sample captured by the second camera,
wherein mapping comprises mapping the monitored gaze to pixels of the scanned image using the registration to the image captured by the second camera.

11. The computer-implemented method of claim 1, further comprising training a machine learning model on the training dataset for generating an outcome of:
when the sample comprises the sample of tissue of a subject: a target predicted pathology report, pathological diagnosis, and/or sample score, in response to an input of a target image of a target biological sample of pathological tissue of a target individual and a target gaze of a target user,
when the sample comprises the manufactured microarray: a target manufacturing defect and/or indication of pass/fail quality check, in response to an input of a target image of a target manufactured microarray, and
when the sample comprises a live cell culture: a target growth rate, cell density, homogeneity parameter, and/or heterogeneity parameter, for the live cell culture.

12. A computer-implemented method for assisting visual analysis of a sample of an object, comprising:
inputting a target image of the sample of the object into a machine learning model trained on a training dataset comprising a plurality of records, wherein at least one record includes:
an image of a sample of an object;
an indication of monitored manipulations by a user of a presentation of the sample; and
a ground truth indication of a monitored gaze of the user viewing the sample on a display or via an optical device mapped to pixels of the image of the sample, wherein the monitored gaze comprises at least one location of the sample the user has or is viewing and an amount of time spent viewing the at least one location; and
obtaining as an output of the machine learning model, an indication of predicted monitored gaze for pixels of the target image, and a heatmap of a plurality of pixels mapped to pixels of the target image, wherein intensity of pixels of the heatmap correlate to a predicted time for gazing, wherein pixels of the heat map are normalized to pixels indicating different actual sizes of the sample at a plurality of zoom levels defined by the monitored manipulations and/or to pixels located at different portions of the sample that are non-simultaneously visible on a display obtained by panning operations of the monitored manipulations.

13. The computer-implemented method of claim 12, wherein the output comprises a time series indicating dynamic gaze mapped to pixels of the target image over a time interval, and further comprising real-time monitoring of a gaze of a user viewing the target image, comparing a difference between the real-time monitoring and the time series, and generating an alert when the difference is above a threshold.

14. The computer-implemented method of claim 12, wherein the record of the training dataset further comprises ground truth indications of manipulations by the user mapped to the ground truth indications of monitored gaze and to the pixels of the image, and wherein the output comprises a prediction of manipulation to a presentation of the target image.

15. The computer-implemented method of claim 13, further comprising real-time monitoring of manipulations of a presentation of the sample by a user, comparing a difference between the real-time monitoring of manipulation and the prediction of manipulations, and generating an alert when the difference is above a threshold.

16. A component for gaze-tracking for integration with a microscope between an objective lens and an eyepiece, comprising:
an optical arrangement that directs a first set of electromagnetic frequencies back-reflected from each eye of a user viewing a sample under a microscope to a respective first camera that generates an indication of tracked gaze of the user, and simultaneously directs a second set of electromagnetic frequencies from the sample under the microscope to a second camera that captures images depicting a field of view the user is viewing;
wherein the first set of electromagnetic frequencies are infrared (IR) frequencies generated by an IR source, the first camera comprises a near IR camera, the second set of electromagnetic frequencies include the visible light spectrum, the second camera comprises a red-green-blue (RGB) camera, and the optical arrangement includes a beam splitter that directs the first set of electromagnetic frequencies from the IR source to an eyepiece where the eye of the user is located, directs the back-reflected first set from the eye of the user via the eyepiece to the NIR camera, and directs the second set of electromagnetic frequencies from the sample to the second camera and to the eyepiece, wherein the optical arrangement that separates the electromagnetic light waves from a single optical path after reflection from two eyes to two optical paths to two of the first cameras is selected from a group consisting of: polarizers and/or waveplates that direct different polarized light to different paths, and/or using infrared spectral light sources with dichroic mirrors and spectral filters, and/or adding amplitude modulation in different frequencies for each optical path for heterodyne detection.

17. The computer-implemented method of claim 1, wherein the image of the sample comprises a sample of tissue of a subject, and the at least one record comprises at least one label indicative of: a pathology report created by the user viewing the sample, a pathological diagnosis created by the user viewing the sample, a sample score indicating a pathological evaluation for the sample created by the user viewing the sample, at least one clinical parameter of the subject whose sample is depicted in the sample, a history parameter of the subject, and/or an outcome of treatment administered to the subject.

18. The computer-implemented method of claim 1, wherein the image of the sample comprises a live cell culture, and the at least one record comprises at least one label indicative of a growth rate, a cell density, a homogeneity parameter, and/or a heterogeneity parameter, of the live cell culture.

\* \* \* \* \*